United States Patent
Shimizu et al.

(10) Patent No.: US 11,481,946 B2
(45) Date of Patent: Oct. 25, 2022

(54) INFORMATION PROCESSING APPARATUS, INFORMATION PROCESSING METHOD, PROGRAM, AND INFORMATION PROCESSING SYSTEM FOR REINFORCING TARGET BEHAVIOR

(71) Applicant: SONY CORPORATION, Tokyo (JP)

(72) Inventors: Itaru Shimizu, Tokyo (JP); Kazuhito Iwasa, Kanagawa (JP); Takanori Morii, Chiba (JP)

(73) Assignee: SONY CORPORATION, Tokyo (JP)

( * ) Notice: Subject to any disclaimer, the term of this patent is extended or adjusted under 35 U.S.C. 154(b) by 0 days.

(21) Appl. No.: 16/757,627

(22) PCT Filed: Oct. 12, 2018

(86) PCT No.: PCT/JP2018/038043
§ 371 (c)(1),
(2) Date: Apr. 20, 2020

(87) PCT Pub. No.: WO2019/082687
PCT Pub. Date: May 2, 2019

(65) Prior Publication Data
US 2020/0342648 A1     Oct. 29, 2020

(30) Foreign Application Priority Data
Oct. 27, 2017  (JP) .............................. JP2017-207775

(51) Int. Cl.
*G06T 13/40* (2011.01)
*A63F 13/822* (2014.01)
(Continued)

(52) U.S. Cl.
CPC .............. *G06T 13/40* (2013.01); *A61B 5/165* (2013.01); *A63F 13/822* (2014.09); *G06F 3/015* (2013.01); *G06F 2203/011* (2013.01)

(58) Field of Classification Search
CPC ........ G06T 13/40; G06F 3/0481; G06F 3/011; G06F 3/015; G06F 2203/011;
(Continued)

(56) References Cited

U.S. PATENT DOCUMENTS 8,797,331 B2 *   8/2014   Sano ...................... A61B 5/744
                                                             345/474
2010/0267450 A1 *  10/2010  McMain ............... A63F 13/822
                                                             463/43
(Continued)

FOREIGN PATENT DOCUMENTS

EP           1589735 A2 *  10/2005  ............. A63F 13/12

*Primary Examiner* — Jennifer Mehmood
*Assistant Examiner* — Donna J. Ricks
(74) *Attorney, Agent, or Firm* — Paratus Law Group, PLLC

(57) ABSTRACT

There is provided information processing apparatuses, information processing methods, programs, and information processing systems capable of reinforcing the reinforcement target behavior without causing the user's consciousness. A quest is presented for urging a user to execute a reinforcement target behavior, and when the user executes the reinforcement target behavior upon the request, an electroencephalogram is measured, emotion is estimated on the basis of the electroencephalogram, and when the number of times that dominant emotion having the highest emotion score among emotion of the emotion estimation results is detected exceeds a predetermined number of times, an avatar is changed corresponding to the emotion that is detected as the dominant emotion. The present disclosure can be applied to long-term feedback technology.

21 Claims, 32 Drawing Sheets

(51) Int. Cl.
*A61B 5/16* (2006.01)
*G06F 3/01* (2006.01)

(58) Field of Classification Search
CPC .... A63F 13/822; A63F 13/212; A63F 13/422; A63F 13/80; A63F 13/67; A63F 13/65; A61B 5/165; A61B 5/318; A61B 5/0533; A61B 5/026; A61B 5/021; A61B 5/08; A61B 5/024; A61B 5/01; A61B 5/14542; A61B 5/0008; A61B 5/0006; A61B 5/0022; A61B 5/02055; A61B 5/16; A61M 21/02

See application file for complete search history.

(56) References Cited

U.S. PATENT DOCUMENTS

| | | | |
|---|---|---|---|
| 2016/0077547 A1* | 3/2016 | Aimone | A61B 5/0022 345/8 |
| 2020/0133394 A1* | 4/2020 | Hann | A61B 5/4854 |

* cited by examiner

FIG. 5
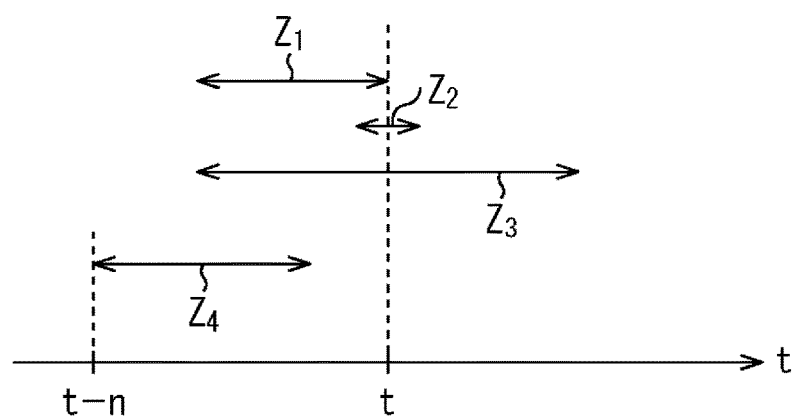
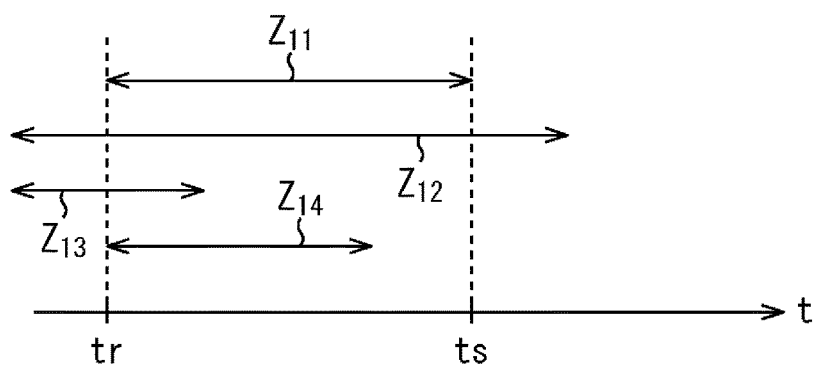

FIG. 7

| Emotion_information |
|---|
| ID |
| Timestamp |
| Config_info |
| User_info |
| Brainwave_raw_1 |
| : |
| Brainwave_raw_n |
| Emo_info_1 |
| Emo_info_2 |

FIG. 8

| Config_info |
|---|
| Eeg_type |
| Eeg_ele_num |
| Sensor_1 |
| : |
| Sensor_n |
| Position |
| Attitude |
| Application_ID |
| Meta_version |

FIG. 10

Emo_info_1

| Emo_type_set |
| Emo_type1_value |
| Emo_type2_value |
| : |
| Emo_typen_value |

Emo_info_2

| Strongest_type |
| Strongest_type_value |
| Weekest_type |
| Weekest_type_value |
| Mind_type |

FIG. 12

| AVATAR | EMOTION | SCORE |
|---|---|---|
| root | m1 | 10 |
|  | m2 | 60 |
|  | m3 | 30 |

FIG. 13

| AVATAR | EMOTION | NUMBER OF TIMES |
|---|---|---|
| root | m1 | 2 |
|  | m2 | 4 |
|  | m3 | 3 |

| AVATAR | EMOTION | NUMBER OF TIMES |
|---|---|---|
| root | m1 | 2 |
|  | m2 | 5 |
|  | m3 | 3 |

FIG. 14

| AVATAR | EMOTION | NUMBER OF TIMES |
|---|---|---|
| A-2 | m1 | 0 |
| | m2 | 0 |
| | m3 | 0 |

FIG. 16

| EXCITED | 10 | × 10 | HP | 100 |
| MYSTERIOUS | 50 | × 2 | MP | 100 |
| IMPRESSED | 15 | × 5 | RECOVERY POWER | 75 |
| I FOUND IT | 20 | × 5 | QUICKNESS | 100 |
| GREAT | 5 | × 5 | DEFENSE POWER | 25 |

FIG. 31
| CURRICULA | AVATAR | PARAMETER |
|---|---|---|
| NATIONAL LANGUAGE |  | LV4 |
| ARITHMETIC |  | LV20 |
| SCIENCE |  | LV12 |
| ⋮ | ⋮ | ⋮ |

INFORMATION PROCESSING APPARATUS, INFORMATION PROCESSING METHOD, PROGRAM, AND INFORMATION PROCESSING SYSTEM FOR REINFORCING TARGET BEHAVIOR

CROSS REFERENCE TO PRIOR APPLICATION

This application is a National Stage Patent Application of PCT International Patent Application No. PCT/JP2018/038043 (filed on Oct. 12, 2018) under 35 U.S.C. § 371, which claims priority to Japanese Patent Application No. 2017-207775 (filed on Oct. 27, 2017), which are all hereby incorporated by reference in their entirety.

TECHNICAL FIELD

The present disclosure relates to information processing apparatuses, information processing methods, programs, and information processing systems. In particular, the present disclosure relates to an information processing apparatus, information processing method, program, and information processing system, allowing repetitive long-term measurement of biometric information and accordingly, long-term feedback to be performed so that the user is urged to reinforce a particular action without causing the user's consciousness.

BACKGROUND ART

A technique of detecting biometric information of a user and estimating a user's emotion on the basis of the detected result is disclosed.

In one example, a technique of estimating emotions on the basis of Russell's circumplex model in which emotions can be mapped to two axes of pleasant-unpleasant and activation-deactivation is disclosed (see Non-Patent Document 1).

In addition, there is disclosed a technique of detecting emotions and sensibility by setting the "emotion" as being defined in Russell's circumplex model and the "sensibility" as being defined by adding temporal axis information to Russell's circumplex model in a case where exteroceptive sensory information (somatic nervous system) and interoceptive sensory information (autonomic nervous system) are integrated and affect responses that occur by comparing them with past experiences or memories are classified into three layers of affect, emotion, and sensibility from low-order to high-order. In this document, the emotion of pleasant-unpleasant uses a-waves in the two axes of the circumplex model (see Patent Document 1).

Furthermore, a technique of performing frequency analysis using a simple monopolar electroencephalograph and estimating preference information is also disclosed (see Patent Document 2).

In addition, a technique of performing mapping of information including biometric information other than electroencephalograms and estimating individual characteristics by applying Russell's circumplex model is also disclosed (see Patent Document 3).

Furthermore, a technique of using emotions obtained by applying the techniques mentioned above is disclosed.

In one example, a technique of measuring electroencephalograms using an electroencephalograph equipped with a head-mounted display and performing zone guidance to achieve neurofeedback is disclosed (see Patent Document 4).

In addition, a technique of changing the state of a displayed character on the basis of biometric information including electroencephalograms or other various information and expressing a situation such as a person's motion state, health state, and emotions is disclosed (see Patent Document 5).

Furthermore, a technique of changing the display state of a character on the basis of the user's action history is disclosed (see Patent Document 6).

Further, a technique of estimating a type and a degree of intensity of the emotion on the basis of electroencephalograms and recording it in association with a camera-captured image, and so specifying the user's emotion with respect to an imaging target and using it in marketing or the like by is disclosed (see Patent Document 7).

Furthermore, a technique of controlling playback of content such as voice depending on biometric information including electroencephalograms is disclosed (see Patent Document 8).

CITATION LIST

Non-Patent Document

Non-Patent Document 1: A Circumplex Model of Affect (Russell 1980)

Patent Document

Patent Document 1: Japanese Patent Application Laid-Open No. 2017-074356
Patent Document 2: Japanese Patent Application Laid-Open No. 2010-131328
Patent Document 3: Japanese Patent Application Laid-Open No. 2013-046691
Patent Document 4: Japanese Patent Application Laid-Open No. 2014-217704
Patent Document 5: Japanese Patent No. 4506795
Patent Document 6: Japanese Patent No. 6102939
Patent Document 7: Japanese Patent Application Laid-Open No. 2015-229040
Patent Document 8: Japanese Patent Application Laid-Open No. 2005-056205

SUMMARY OF THE INVENTION

Problems to be Solved by the Invention

However, the above-mentioned techniques of urging the user to reinforce a particular action (neurofeedback) necessarily cause the user consciously to select to use a system for urging reinforcement of the particular action, so it is possible to urge the user to reinforce the particular action only if the user is voluntarily conscious of being necessary to reinforce the particular action.

Further, the technique of presenting a character performs only the presentation of the character, so it is necessary to urge the user to perform measurement of biometric information such as electroencephalograms, which causes the user to measure the biometric information and so the burden is on the user.

Furthermore, in detecting the biometric information described above, in one example, in a case where electroencephalograms are measured as biometric information, the user is difficult in practice to be placed in a situation where the user wants to perform electroencephalogram measurement naturally or in a particular situation or emotional state during electroencephalogram measurement.

In addition, the above-mentioned techniques may be capable of providing short-term feedback on emotion measurement results, but long-term feedback using results obtained by repetitive long-term emotion measurement is not taught.

The present disclosure is made in view of such a situation, and in particular, it is intended to urge the user to reinforce a particular action by the repetitive long-term measurement of biometric information and by the long-term feedback accordingly without causing the user's consciousness.

Solutions to Problems

According to an aspect of the present disclosure, there is provided an information processing apparatus including an information processing unit configured to change characteristics of an avatar determined by a previous emotion estimation result to other characteristics on the basis of an emotion estimation result estimated on the basis of an electroencephalogram detected in response to reinforcement target behavior and present the characteristics.

The information processing unit may present information used to urge the reinforcement target behavior, and the information processing apparatus may further include an electroencephalogram detection unit configured to detect the electroencephalogram at a predetermined timing based on a timing of executing the reinforcement target behavior.

The electroencephalogram detection unit detects the electroencephalogram at the timing of executing the reinforcement target behavior, during a period from timing before a predetermined time of the timing of executing the reinforcement target behavior to timing after a predetermined time of the timing of executing the reinforcement target behavior, or during a predetermined period from a timing of a predetermined time before the timing of executing the reinforcement target behavior.

The avatar may be a form of representation for causing a user to recognize the emotion estimation result.

The characteristics may be an appearance of the avatar, displayed contents of a text format, voice, vibration, smell, a sense of touch, a sense of taste, and a movement or an attitude in a case of using a robot.

The reinforcement target behavior may be photographing.

An imaging control unit configured to control imaging of a photograph captured in the photographing and a display control unit configured to cause the photograph and the avatar to be displayed may further be included.

The information processing unit may present the information used to urge the reinforcement target behavior as a task.

An emotion estimation unit configured to analyze the detected electroencephalogram, determine a score indicating a degree of intensity or a ratio for each of a plurality of elemental emotions, and output the score as the emotion estimation result may further be included.

The information processing unit may specify a predetermined emotion on the basis of the score for each of the plurality of elemental emotions every time the emotion estimation result is output and stores a number of times of specification of the predetermined emotion in a long-term change table for each of the plurality of elemental emotions.

The information processing unit may change and present a form of the avatar on the basis of the number of times of specification of the predetermined emotion for each of the emotions, the number of times being stored in the long-term change table.

The predetermined emotion may be a dominant emotion having a highest intensity or ratio in the plurality of elemental emotions, and the information processing unit may change and present the characteristics of the avatar depending on an emotion having a number of times of specification of the dominant emotion larger than a predetermined number of times, the number of times being stored in the long-term change table.

The reinforcement target behavior may be photographing, and the information processing unit may store an image captured by the photographing as a history in association with information regarding the characteristics of the avatar.

The information processing unit may further record information relating to an emotion based on the emotion estimation result in association with the image captured by the photographing.

The information processing unit may cause a display unit to display a history image indicating a history of a change in the characteristics of the avatar.

The information processing unit may cause a display unit to display a predictive image used to predict a change in the characteristics of the avatar on the basis of the emotion estimation results obtained a plurality of times.

According to an aspect of the present disclosure, there is provided an information processing method including information processing of changing characteristics of an avatar determined by a previous emotion estimation result to other characteristics on the basis of an emotion estimation result estimated on the basis of an electroencephalogram detected in response to reinforcement target behavior and presenting the characteristics.

According to an aspect of the present disclosure, there is provided a program causing a computer to function as an information processing unit configured to change characteristics of an avatar determined by a previous emotion estimation result to other characteristics on the basis of an emotion estimation result estimated on the basis of an electroencephalogram detected in response to reinforcement target behavior and present the characteristics.

According to an aspect of the present disclosure, there is provided an information processing system including an electroencephalograph, and an information processing apparatus, in which the electroencephalograph includes an electroencephalogram detection unit configured to detect an electroencephalogram in response to reinforcement target behavior by a user, and the information processing apparatus includes an information processing unit configured to change characteristics of an avatar determined by a previous emotion estimation result to other characteristics on the basis of an emotion estimation result estimated on the basis of the detected electroencephalogram and present the characteristics.

In an aspect of the present disclosure, characteristics of an avatar determined by a previous emotion estimation result is changed to other characteristics on the basis of an emotion estimation result estimated on the basis of an electroencephalogram detected in response to reinforcement target behavior and presented.

Effects of the Invention

According to an embodiment of the present disclosure, it is possible to urge the user to reinforce a particular action and perform a sequence of processing without causing the user's consciousness on the basis of a measurement result of biometric information in a user's particular situation or emotional state repeatedly measured in the long term.

BRIEF DESCRIPTION OF DRAWINGS

FIG. 5 is a diagram illustrated to describe the timing of detecting an electroencephalogram.

FIG. 7 is a diagram illustrated to describe a data configuration of Emotion_information used to store an electroencephalogram detection result and an emotion estimation result.

FIG. 8 is a diagram illustrated to describe a data configuration of Config_info.

FIG. 10 is a diagram illustrated to describe a data configuration of Emo_info_1 and Emo_info_2.

FIG. 12 is a diagram illustrated to describe a short-term change table.

FIG. 13 is a diagram illustrated to describe a long-term change table.

FIG. 14 is a diagram illustrated to describe a long-term change table.

FIG. 16 is a diagram illustrated to describe a setting example of an avatar parameter.

FIG. 31 is a diagram illustrated to describe a seventh modification.

MODE FOR CARRYING OUT THE INVENTION

Figure 1:
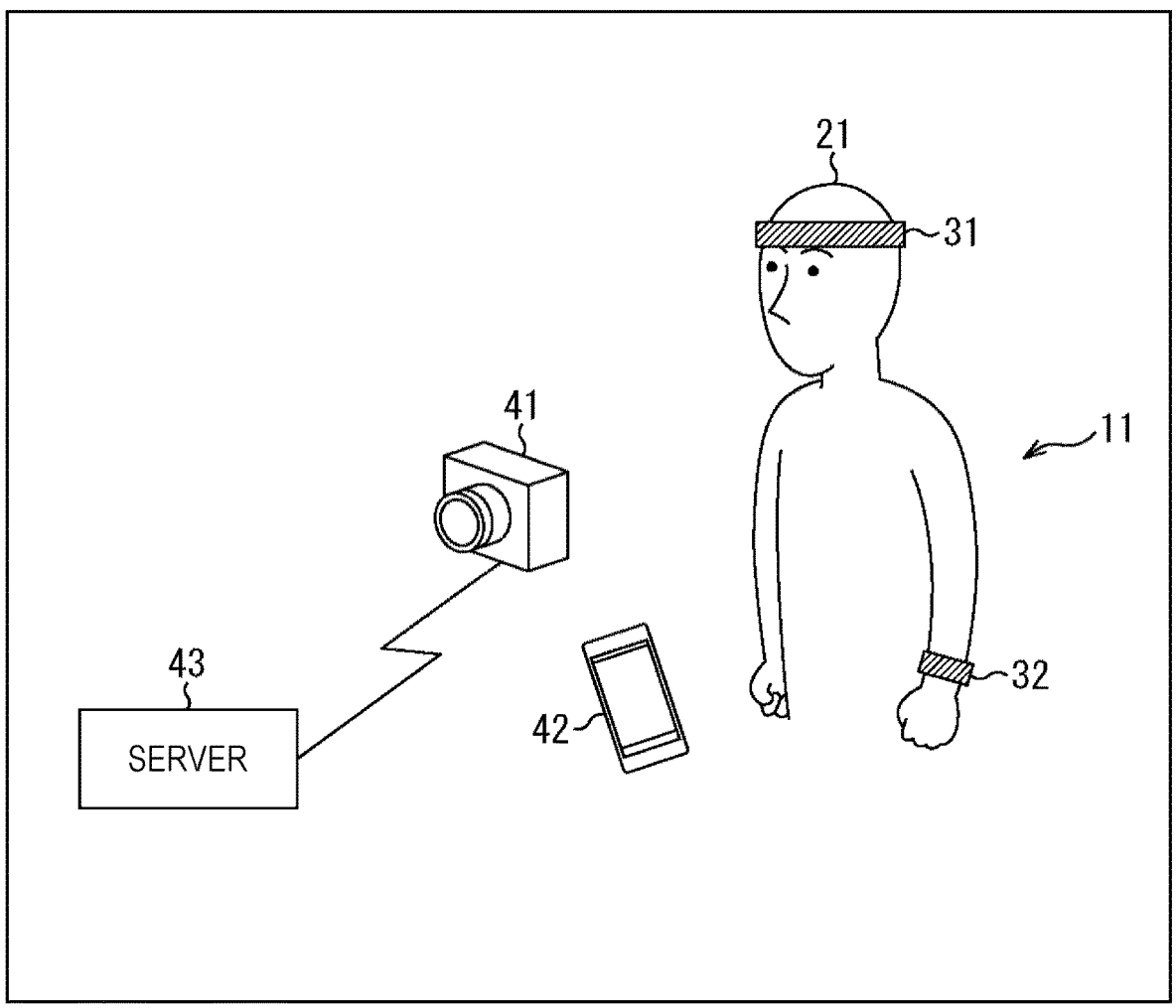
FIG. 1 is a diagram illustrating an appearance configuration example of an information processing system of the present disclosure.

Hereinafter, a preferred embodiment of the present disclosure will be described in detail with reference to the appended drawings. Note that, in this specification and the appended drawings, components that have substantially the same function and configuration are denoted with the same reference numerals, and repeated explanation of these structural elements is omitted.

Moreover, the description will be given in the following order.

1. Overview of information processing system of present disclosure
2. Exemplary configuration of information processing system of present disclosure
3. First modification
4. Second modification
5. Third modification
6. Fourth modification
7. Fifth modification
8. Sixth modification
9. Seventh modification
10. Eighth modification
11. Ninth modification
12. Tenth modification
13. Example executed by software <<1. Overview of Information Processing System of Present Disclosure>>

An overview of an information processing system of the present disclosure is described and then the information processing system is described.

An information processing apparatus according to the present disclosure is intended to allow repetitive long-term measurement of biometric information in a user's particular situation or emotional state in the long term to be performed, allow the user to be urged in the long term to reinforce a particular action on the basis of a measurement result, and allow a sequence of processing to be achieved without causing the user's consciousness.

More specifically, the information processing apparatus according to the present disclosure measures biometric information, particularly, electroencephalogram upon particular behavior, presents, as a representation of an avatar, a form corresponding to user behavior or biometric information obtained by analyzing a measurement result, and gives an incentive to a change in the presented avatars, thereby urging the user to reinforce the action (neurofeedback).

In other words, the information processing apparatus according to the present disclosure does not directly feedback a detection result of electroencephalogram or other biometric information upon particular behavior, but expresses a form corresponding to an estimation result of user's emotion obtained by analyzing the measurement result as an avatar and gives repetitive long-term presentation of the avatar being changed, thereby achieving long-term feedback.

The avatar is a character, which causes a user to objectively recognize an emotion estimation result based on the user's biometric information and is displayed on, in one example, a display apparatus such as a display. In other words, the user is able to recognize the user's emotion estimation result by looking at the avatar. However, the avatar can be other things than a character that changes its appearance as long as the user's state corresponding to the emotion estimation result can be expressed to be recognizable by the user. Examples thereof include a displayable text format, voice, vibration, smell, sense of touch, sense of taste, and a tangible robot or like that changes its movement and attitude depending on the emotion estimation result.

Further, the avatar changes the appearance characteristics, in one example, by making the outer shape round or square on the basis of the emotion estimation result. In addition, the avatar is also able to change its characteristics other than the appearance, such as the contents of dialogue (e.g., dialogue algorithm) with a user that utters violent or friendly wording, on the basis of the emotion estimation result.

Thus, the avatar's characteristics include appearance (outer shape) of the avatar, display contents in a text format expressing the avatar, voice, vibration, smell, sense of touch, sense of taste, movement and attitude upon using a robot, or the like. In other words, the avatar is able to change not only the appearance characteristics but also other characteristics than the appearance on the basis of the emotion estimation result.

In other words, the avatar is a form of expression for allowing the user to recognize the emotion estimation result and for allowing the user to recognize by oneself the user's emotion estimation result by changing its appearance and/or those other than the appearance on the basis of the emotion estimation result.

Such a configuration allows the intention for the user to be replaced from "reinforcement of particular behavior" to "change of an avatar", and urges the user to reinforce the particular behavior without causing the user's consciousness of "reinforcement of the particular behavior".

Consequently, it is possible to achieve the reinforcement of the user's behavior without causing the user's consciousness of "reinforcement of the particular behavior". Specifically, it is possible to achieve the reinforcement of behavior associated with sensibility, such as the photographing, as not only the short-term reinforcement of behavior but also the long-term reinforcement of behavior.

In this description, "to reinforce behavior" or "behavior reinforcement" means to give the user a motivation such as wanting to perform particular behavior or change in appearances to a particular state.

More specifically, in a case where particular behavior is "to study", the behavior for the user to want to study, that is, to increase the user's willingness to study is the behavior reinforcement, that is, to reinforce the behavior.

Further, the particular behavior includes, in one example, changing the appearance to a particular state such as "becoming a hero". Thus, in a case where changing the appearance to a particular state means "becoming a hero", the increase of willingness to become a hero is the behavior reinforcement, i.e., to reinforce the behavior.

Furthermore, not only positive behavior as described above but also negative behavior can be a target to be reinforced, and examples thereof include the behavior of "do not oversleep" or the behavior of "do not eat too much".

Moreover, the particular behavior that is to be a target for behavior reinforcement is also hereinafter referred to as reinforcement target behavior. in other words, in the above-mentioned example, the particular behavior of "to study" or "becoming a hero" is behavior that can be a target to be reinforced, and in a case where it is targeted, any of them can be the reinforcement target behavior.

Further, the information processing apparatus according to the present disclosure makes it possible to urge a specific method of electroencephalographic measurement on the user by instructing the user to perform predetermined behavior through gamification that is an activity using a game without causing the user's consciousness.

More specifically, the information processing apparatus according to the present disclosure urges, in one example, "walking state" on the user by presenting a "task associated with walking action" such as "please walk toward A" and then measures the electroencephalogram, thereby acquiring the electroencephalogram of the user in the "walking state" without causing the user's consciousness. In other words, although the user is able to conscious that the walking state is urged, the user is not conscious of measuring the electroencephalogram in the walking state, and thus it is possible to achieve the electroencephalogram measurement in the walking state without causing the user's consciousness.

In addition, the information processing apparatus according to the present disclosure presents "to photograph a surprising thing" such as "please photograph a surprising thing" and urges the "surprised state" on the user, and then measuring the electroencephalogram, thereby acquiring the electroencephalogram in which the user is in "surprised state". In other words, although the user is able to conscious that "to photograph a surprising thing" is urged, the user is not conscious of measuring the electroencephalogram in the surprised state, and thus it is possible to achieve the electroencephalogram measurement in the surprised state without causing the user's consciousness. Furthermore, the information processing apparatus according to the present disclosure is also capable of preventing noise from occurring in measuring the biometric information by, in one example, providing the presentation of urging "action to correct attitude" such as "please stretch your back".

Furthermore, the information processing apparatus according to the present disclosure is capable of objectifying and quantifying the expression of an avatar by performing "change in states of avatar" on the basis of electroencephalogram (biometric information).

Further, the avatar changes on the basis of biometric information that is incapable of being changed consciously by the user, so it is possible to achieve an avatar that is incapable of being changed willfully by the user's intention.

Furthermore, the avatar changes on the basis of the electroencephalogram (biometric information), and so in one example, in a case where the user's state is presented and expressed as the avatar, the avatar presented on the basis of the objective measurement result based on the biological information is capable of presenting a highly accurate state with respect to the user's state using an avatar to the user, as compared with an avatar that is presented on the basis of information subjectively written by the user, such as questionnaires. In addition, it is possible to present the avatar using information, such as biometric information, which is incapable of being controlled by the user while changing it quantitatively, and so the sense of satisfaction can be given to the user. Consequently, it is possible to achieve an avatar that is less bored with the user.

In addition, the avatar changes on the basis of the detection result of the electroencephalogram in which the user characteristics are reflected, and so it is possible to achieve an artificial intelligence (AI) conversation algorithm that reflects the user characteristics.

Furthermore, the avatar is capable of expressing the user's "particular emotion", so the use of the avatar makes it possible to visualize the user's mental state, particularly temporal, geographical, and social graphic change to the user.

In addition, the avatar is based on an objective measurement value rather than a subjective measurement value expressed by the user, so it is possible to achieve indirect communication using "unconscious" information that is not noticed by the user or using the information or expression close to "real intention".

Furthermore, the presentation using an avatar allows feelings with the present self, the past self, and others to be shared. In addition, this makes it possible to reinforce and induce the user's reinforcement target behavior by performing positive feedback on the "particular emotion". Moreover, a single user can have a plurality of avatars, and in one example, the user can use them appropriately in accordance with TPO.

<<2. Exemplary Configuration of Information Processing System of Present Disclosure>>

An exemplary configuration of the information processing system according to the present disclosure is now described with reference to FIG. 1.

The information processing system in FIG. 1 gives various tasks on the user by presenting a quest to the user like a game such as roll playing game (RPG), acquires electroencephalograms and other types of biometric information obtained upon completing the task for the quest, analyzes them, changes the avatar depending on the analyzed result, and presents it, in which these processing steps are performed in the long term.

The information processing system of FIG. 1 causes the user to unconsciously reinforce the reinforcement target behavior on the basis of the long-term biometric information by repeating the presentation of the task for urging such reinforcement target behavior and the presentation of the avatar that changes depending on the biometric information upon completing the task.

Moreover, in this description, the quest is a task given to the user, and in a case where the reinforcement target behavior is photographing, in one example, a task of "please photograph an excited image" or "please photograph while walking" is given.

More specifically, the information processing system gives various quests to the user, acquires the user's electroencephalogram and biometric information upon performing the quest by the user, analyzes the acquired electroencephalogram and biometric information, and changes and presents the avatar associated with the user so that the analyzed result is reflected.

In this event, the avatar is changed and presented on the basis of the analysis result of the biometric information upon the user's photographing operation by performing the task presented as the quest.

Consequently, the behavior of photographing as the reinforcement target behavior is reinforced by stimulating the user's willingness to change the avatar while viewing the change of the avatar being presented without causing the user's consciousness.

More specifically, an information processing system 11 includes an electroencephalograph 31, a biometric sensor 32, a physical sensor 33, an information processing apparatus 41, a display apparatus (e.g., smartphone) 42, and a server 43.

The information processing apparatus 41 is an apparatus of processing information, which is equipped with what is called imaging function, and generates a quest that urges the reinforcement target behavior and displays the quest on the display apparatus 42 for presentation.

In this event, the information processing apparatus 41 controls the electroencephalograph 31 and the biometric sensor 32 and acquires electroencephalograms and other biometric information of a user 21 upon photographing while performing the task when the user 21 executes the task presented by the quest. In addition, the information processing apparatus 41 supplies the acquired electroencephalogram and other biometric information to the server 43 for analysis and acquires the analysis result. Then, the information processing apparatus 41 causes the display apparatus 42 to present the avatar while changing it on the basis of the analysis result. The information processing apparatus 41 repeats this series of processing in the long term.

The display apparatus 42 is, in one example, a smartphone. The display apparatus 42, which is controlled by the information processing apparatus 41, displays an avatar associated with the user 21 while changing it on the basis of the analysis result of biometric information in presenting a supplied quest or executing a task presented as a quest.

The server 43 is, in one example, a cloud server that exists on a network. The server 43 analyzes the user 21, estimates an emotion on the basis of the user's electroencephalogram and other biometric information supplied from the information processing apparatus 41, and supplies an emotion estimation result as an analysis result to the information processing apparatus 41.

The emotion estimation result is obtained by, in one example, scoring each of a plurality of emotions that can be estimated, by analyzing the electroencephalograms or biometric information.

The electroencephalograph 31 is wound around, in one example, the head of the user 21 as illustrated in FIG. 1. The electroencephalograph 31 measures the potential of the scalp of several parts in the head by using electrodes 31a to 31c (FIG. 2) provided on the main body, detects the electroencephalogram on the basis of the measurement result, and transmits the detected electroencephalogram to the information processing apparatus 41 via a communication unit 74 (FIG. 3).

The biometric sensor 32 is wound around, in one example, the arm of the user 21 in FIG. 1, measures biometric information other than electroencephalogram, includes a body temperature sensor, a sweat rate sensor, a heart rate sensor, a blood flow sensor, or the like, and transmits the measured biometric information to the information processing apparatus 41.

Moreover, the emotion can be estimated using biometric information other than electroencephalograms. Thus, the biometric sensor 32 measures biometric information other than electroencephalograms and transmits the results to the information processing apparatus 41 as necessary. In addition, the emotion estimation can be achieved in principle by using electroencephalograms, and so biometric information other than the electroencephalogram may not be necessary.

Thus, the biometric sensor 32 that measures biometric information other than electroencephalograms may not be a component necessary for estimating emotions.

The physical sensor 33 includes an accelerometer that measures a user's motion and a global positioning system (GPS) sensor that measures the geographic location, and transmits the acceleration and position information that are measured physical information to the information processing apparatus 41.

<Exemplary Configuration of Electroencephalograph>

An exemplary configuration of the electroencephalograph 31 is now described in detail with reference to FIG. 2.

Figure 2:
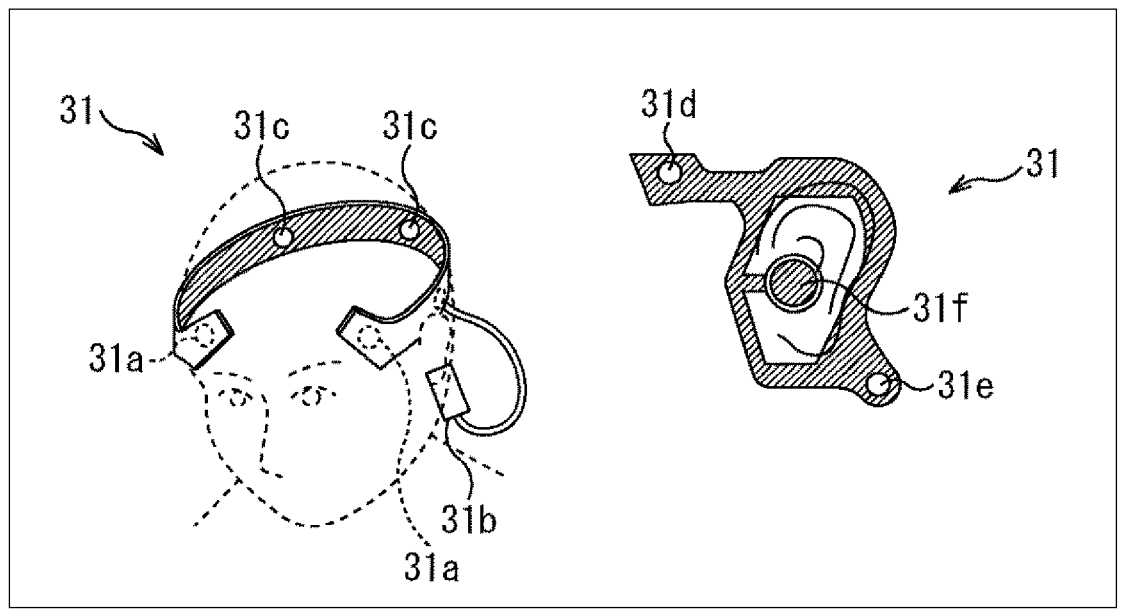
FIG. 2 is a diagram illustrating an appearance configuration example of an electroencephalograph in FIG. 1.
Figure 3:
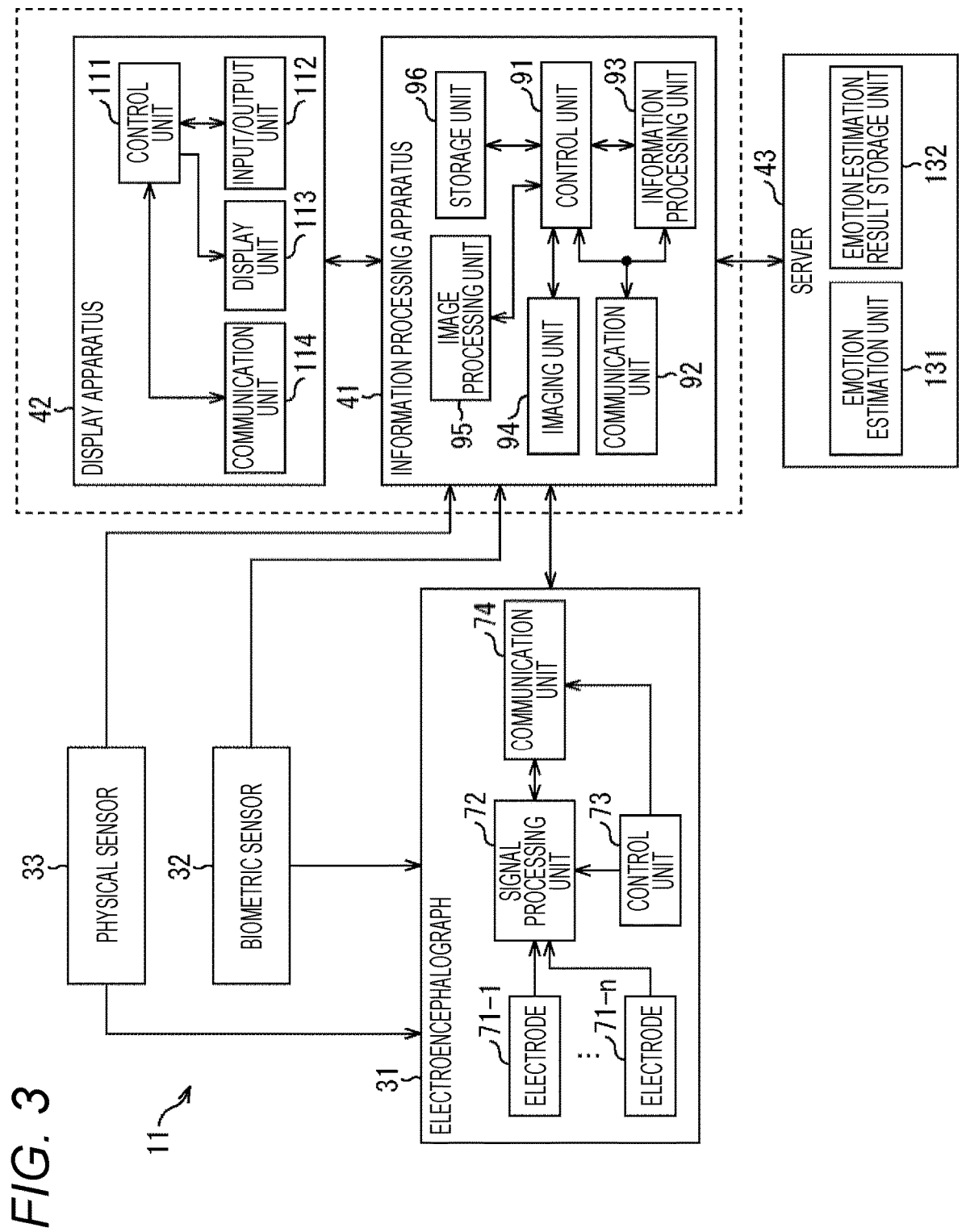
FIG. 3 is a diagram illustrating an exemplary configuration for achieving a function of the information processing system in FIG. 1.

The electroencephalograph 31 shown on the left side of FIG. 2 is a type worn on the head 21a of the user 21, and is provided with electrodes 31a to 31c that is in contact with the scalp. Each of the electrodes 31a to 31c measures the potential in the scalp and, on the basis of the measurement result, measures electroencephalogram (brain waves). The electrode 31a among the electrodes is in contact with the scalp near the temples and measures the potential near the temples. In addition, the electrode 31b is a clip-like electrode that is in contact with the earlobe while fitting in it and measures the potential of the earlobe as a reference potential. The electrode 31c is in contact with the occipital scalp and measures the potential of the occipital scalp.

In other words, the electroencephalograph 31 shown on the left side of FIG. 2 measures the potential difference between the potential at the electrodes 31a and 31c and the potential at the electrode 31b, which is the reference potential, and detects electroencephalogram using the measurement result. Moreover, as a reference electrode, the electrode 31b with a clip shape shown on the left side of FIG. 2 is used for the measurement because the influence on the brain potential is small and the earlobe suitable for taking the reference potential can be used for it. However, an electrode that grips the earlobe with a clip-like electrode involves pain, and so it is difficult to withstand the long-time use. Thus, the mastoid on the backside of the ear (mastoid process) or its vicinity is also less affected on the brain potential and are suitable as a reference electrode, so the electrode for the measurement can be provided on the mastoid on the backside of the ear (mastoid process) or in the vicinity thereof.

Further, the electroencephalograph shown on the right side of FIG. 2 is a type that is hung on the ear of the user 21 and is provided with electrodes 31d to 31f that measure the potential of the skin around the ear of the scalp.

The electrode 31d is in contact with the scalp near the temples and measures the potential near the temples. In addition, the electrode 31e is in contact with the smatoid (mastoid process) near the backside of the ear and measures the potential of the smatoid near the backside of the ear as a reference potential. The electrode 31f also has a function as an earphone and measures the potential in the ear.

In other words, the electroencephalograph 31 shown on the right side of FIG. 2 measures the potential difference between the potential at the electrodes 31d and 31f and the potential at the electrode 31e as a reference potential, and detects the electroencephalogram using the measurement result. Note that as long as the potential difference is obtained, other portions than earlobe or mastoid can be measured as the reference potential.

<Exemplary Configuration of Achieving Functions of Information Processing System>

An exemplary configuration for achieving functions of the information processing system 11 is now described with reference to FIG. 3.

The information processing apparatus 41 includes a control unit 91, a communication unit 92, an information processing unit 93, an imaging unit 94, an image processing unit 95, and a storage unit 96.

The control unit 91 controls the overall operation of the information processing apparatus 41 and is constituted as, in one example, a microcomputer. The control unit 91 includes a memory unit that stores necessary data and programs, a processor that executes predetermined processing, or the like.

The communication unit 92, which is controlled by the control unit 91, receives and transmits necessary data from and to the electroencephalograph 31, the biometric sensor 32, and the physical sensor 33, and the display apparatus 42 through near field communication such as wireless local area networks (LANs) using Wi-Fi or Bluetooth (registered trademark) by communication with them.

The information processing unit 93, which is controlled by the control unit 91, causes the image processing unit 95 to generate an image that presents a quest for urging the reinforcement target behavior and supplies an image that presents the acquired quest to the display apparatus 42 for displaying it via the communication unit 92. In addition, the information processing unit 93 controls the communication unit 92 so that the communication unit 92 transmits the electroencephalogram detection result and the biometric information supplied from the electroencephalograph 31 and the biometric sensor 32 to the server 43. The information processing unit 93 causes the server 43 to analyze the electroencephalogram and the biometric information and to estimate emotions, and then acquires an emotion estimation result that is an analysis result. Then, the information processing unit 93 controls the image processing unit 95 so that the image processing unit 95 changes the avatar on the basis of the emotion estimation result to generate an image that presents an avatar changed on the basis of the emotion estimation result. The information processing unit 93 acquires the image that presents the changed avatar and causes the display apparatus 42 to display it. Furthermore, the information processing unit 93 stores the emotion estimation result in the storage unit 96 in association with an image captured by the imaging unit 94.

Moreover, although the present disclosure describes an example in which the information processing unit 93 is equipped with the function of changing an avatar on the basis of an emotion estimation result and generating an image that presents the avatar changed on the basis of the emotion estimation result, this function can be equipped by the server 43.

The imaging unit 94 is configured to achieve a camera function in the information processing apparatus 41. More specifically, the imaging unit 94 is provided with an image sensor implemented with a complementary-metal-oxide semiconductor (CMOS), a charge-coupled device (CCD), or the like and an optical block. The imaging unit 94, which is controlled by the control unit 91, captures an image and outputs the captured image to the image processing unit 95.

The image processing unit 95, which is controlled by the information processing unit 93, generates an image that presents a quest for urging the reinforcement target behavior and supplies the image to the information processing unit 93. The information processing unit 93 acquires the image that presents the quest generated by the image processing unit 95 and supplies the image to the display apparatus 42 for displaying it via the communication unit 92. In addition, the image processing unit 95, which is controlled by the control unit 91, performs noise reduction or compression processing on the image captured by the imaging unit 94 and, at the same time, stores the electroencephalogram and biometric information at the time of imaging and the emotion estimation result that is the analysis result of the electroencephalogram and biometric information in the storage unit 96 in association with the image.

The display apparatus 42 is, in one example, a smartphone. The display apparatus 42 generates and displays an image that presents a quest given in instruction by the information processing apparatus 41, an image that presents an avatar, and a history image of an avatar or a predictive image of a change in avatars for displaying it.

Moreover, the display apparatus 42 can be other than a smartphone and it can be any other device as long as it has a display function and a communication function, such as a tablet mobile terminal or a smartwatch.

More specifically, the display apparatus 42 includes a control unit 111, an input/output unit 112, a display unit 113, and a communication unit 114.

The control unit 111 is constituted as a microcomputer or the like that controls the overall operation of the display apparatus 42.

The input/output unit 112 functions as an interface for signals input and output to and from the display apparatus 42 that functions as a smartphone.

The display unit 113 is constituted as a liquid crystal display (LCD), an organic electro luminescence (EL), or the like, and displays an image that presents the quest that is output from the information processing apparatus 41, an image that presents the avatar, and a history image of an avatar or a predictive image of a change in avatars.

Moreover, the display of an avatar is expressed not only by an image displayed on the display unit 113 but also as feedback in the form of text format, voice, vibration, smell, sense of touch, sense of taste, and motion of a robot or the like (e.g., in the case of a dog-shaped robot, how to dance, how to swing a tail, facial expression, etc.) to express its change.

Further, the display unit 113 functions as a touchscreen panel, and so receives an operation of a remote camera shutter for the imaging unit 94 of the information processing apparatus 41 or an operation input of various types of information by a user and outputs it to the control unit 111.

The communication unit 114, which is controlled by the control unit 111, receives and transmits necessary data from and to the information processing apparatus 41 through near field communication such as wireless local area networks (LANs) using Wi-Fi or Bluetooth by communication with it. More specifically, the communication unit 114 receives, in one example, an image that presents a quest output from the information processing apparatus 41, an image that presents an avatar, and a history image of an avatar or a predictive image of a change in avatars.

Moreover, the functions of both the information processing apparatus 41 and the display apparatus 42 can be achieved by a smartphone alone. In this case, the configuration having both functions of the information processing apparatus 41 and the display apparatus 42 that are surrounded by a dotted line in the figure is achieved by the smartphone.

The electroencephalograph 31 includes electrodes 71-1 to 71-$n$, a signal processing unit 72, a control unit 73, and a communication unit 74.

The control unit 73 is constituted as a microcomputer or the like that controls the overall operation of the electroencephalograph 31.

The electrodes 71-1 to 71-$n$ have a configuration corresponding to, in one example, the electrodes 31$a$ to 31$c$ or the electrodes 31$d$ to 31$f$ in FIG. 2. The electrodes 71-1 to 71-$n$ measure the potential necessary for measuring the brain waves of the user 21 and output the measured potential signal to the signal processing unit 72.

The signal processing unit 72, which is controlled by the control unit 73, generates an electroencephalogram waveform on the basis of the potential signal supplied from the electrodes 71-1 to 71-$n$ and outputs it to the communication unit 74.

The communication unit 74, which is controlled by the control unit 73, receives and transmits necessary data from and to the information processing apparatus 41 through near field communication such as wireless local area networks (LANs) using Wi-Fi or Bluetooth by communication with it. More specifically, the communication unit 74 outputs the electroencephalogram waveform supplied from the signal processing unit 72 to the information processing apparatus 41.

The biometric sensor 32 is a general term for sensors that detect biometric information other than an electroencephalogram and includes, in one example, a body temperature sensor, a sweat rate sensor, a heart rate sensor, a blood flow sensor, or the like. The biometric sensor 32 transmits the measured biometric information to the information processing apparatus 41. In addition, the physical sensor 33 includes an accelerometer that measures the user's motion and a global positioning system (GPS) sensor that measures the geographic location, and transmits physical information including the measured acceleration and position information to the information processing apparatus 41.

The server 43 includes an emotion estimation unit 131 and an emotion estimation result storage unit 132. The emotion estimation unit 131 estimates a user's emotion on the basis of the electroencephalogram detection result and biometric information supplied from the information processing apparatus 41. More specifically, the emotion estimation unit 131 calculates a proportion of m particular emotions that are set in advance from the electroencephalogram detection result and the biometric information and obtains the calculated result as a score for each emotion. Moreover, the emotion estimation unit 131 can estimate an emotion on the basis of other things than the electroencephalogram detection result and biometric information or can obtain the emotion, in one example, using information obtained from the reinforcement target behavior. In other words, in the case where the reinforcement target behavior is, in one example, photographing, the emotion estimation unit 131 can estimate the emotion on the basis of the composition or type of the subject in the photograph taken by performing the reinforcement target behavior or can estimate the emotion using shooting intervals or the like as an index such as whether continuous shooting or long-time shooting is performed.

The emotion estimation result storage unit 132 stores the emotion estimation result estimated by the emotion estimation unit 131. The emotion estimation unit 131 can estimate emotions using a past emotion estimation result stored in the emotion estimation result storage unit 132 as necessary as well as using the electroencephalogram and biometric information.

Moreover, the emotion estimation unit 131 and the emotion estimation result storage unit 132 can be provided in the information processing apparatus 41.

Further, the emotion in the present disclosure refers to an evaluation reaction of a user to other persons, things, events, external environments, or the like.

Further, the emotion includes a reaction involving physiological arousal (also referred to as affect) in which the start and end with respect to the event are obvious.

Examples of a physiological reaction among emotions include excitement, sleepiness, comfort-discomfort, and concentration. These can be identified on the basis of the frequency of electroencephalogram, extraction of event-related potential, and biological reaction such as heartbeat and sweating.

In addition, the emotion includes those estimated by applying the physiological response mentioned above to a specific model. In one example, in Russell's model (see the literature in the related art), other types of emotions are estimated on the basis of two evaluation axes of sleepiness-arousal and comfort-discomfort, and such various models can be used.

Furthermore, the emotion includes those estimated using other information than biometric information, such as environmental information, in addition to the physiological responses mentioned above or emotions estimated from physiological responses.

In one example, information, such as the event attended by users, a situation whether commuting or taking a walk, or a communication partner, is capable of being obtained from external information such as lifelog or location information, camera photographing information, SNS conversation history.

The emotion is also influenced by the context or environment, and the estimation of the situation where the user is placed on the basis of such external information makes it possible to perform more advanced emotion estimation by taking this result into account.

In particular, the emotion, which can be influenced by culture or society, such as four emotions (joy, anger, sorrow, and pleasure), jealousy, guilt, sympathy, and morals among emotions, can be estimated with higher accuracy by using external information in addition to biometric sensing.

The type of emotion that is necessary to be obtained is set depending on the reinforcement target behavior, and in a case where the reinforcement target behavior is behavior such as photographing, and examples thereof include "emotion relating interests and curiosity", "emotion of doubts (wondering) or disharmony", "discovery", "surprise", "desire for acquisition", "expectation", "admiration", "excited", "mysterious", "impressed", "I found it", "great", and so on.

In addition, examples of the type of emotion in a case where the reinforcement target behavior is behavior such as learning include "motivation to learn", "concentration", "bored", "sleepiness", "relaxation", and "sense of accomplishment for learning", and so on.

Furthermore, examples of the types of emotion in a case where the reinforcement target behavior is behavior such as communication include "interest", "like-dislike", "sympathy", "boredom", "four emotions (joy, anger, sorrow, and pleasure)", and "surprise".

In addition, the emotion to be estimated can be estimated by a combination of basic emotions. In one example, the emotion of "discovery" can necessitate a combination of the emotion of "surprise" and the emotion of "interest".

Furthermore, in estimating the emotion, the respective scores of the positive and negative emotions for the particular emotion are obtained and the difference between them can be used as an emotion score.

In addition, a combination of a plurality of emotions, which is set for particular reinforcement target behavior, is hereinafter also referred to as an emotion set. The emotion set is a set of elemental emotions, which are emotions relating to the reinforcement target behavior and are a plurality of emotions that are considered to be suitable for urging to reinforce the reinforcement target behavior. In other words, in the case where the reinforcement target behavior is photographing, if the emotions necessary for the emotion estimation unit 131 are five types of emotions of "excited", "mysterious", "impressed", "I found it", and "great", the set of five types of emotions including "excited", "mysterious", "impressed", "I found it", and "great is also referred to as the emotion set in the case where the reinforcement target behavior is photographing. In this case, the emotion estimation unit 131 determines a proportion in setting the total of five types of emotions including "excited", "mysterious", "impressed", "I found it", and "great" to a hundred on the basis of the electroencephalogram detection result and the biometric information, and outputs a score corresponding to each proportion as the emotion estimation result.

Moreover, the description below is given on the assumption that the emotion estimation unit 131 outputs, as the emotion estimation result, a result obtained by scoring the respective proportions (intensities) with respect to the emotion set having five types of elemental emotions including "excited", "mysterious", "impressed", "I found it", and "great" among the emotions on the basis of the electroencephalogram detection result and the biometric information.

<Display Example of Image Presenting Quest>

A display example of an image used to present a quest that causes the user to execute the reinforcement target behavior in the information processing system of FIG. 1 is now described with reference to FIG. 4. In this example, the reinforcement target behavior is photographing, so the description is given of an example of displaying an image used to present a quest in taking a photograph using the information processing apparatus 41 that functions as a camera.

Figure 4:
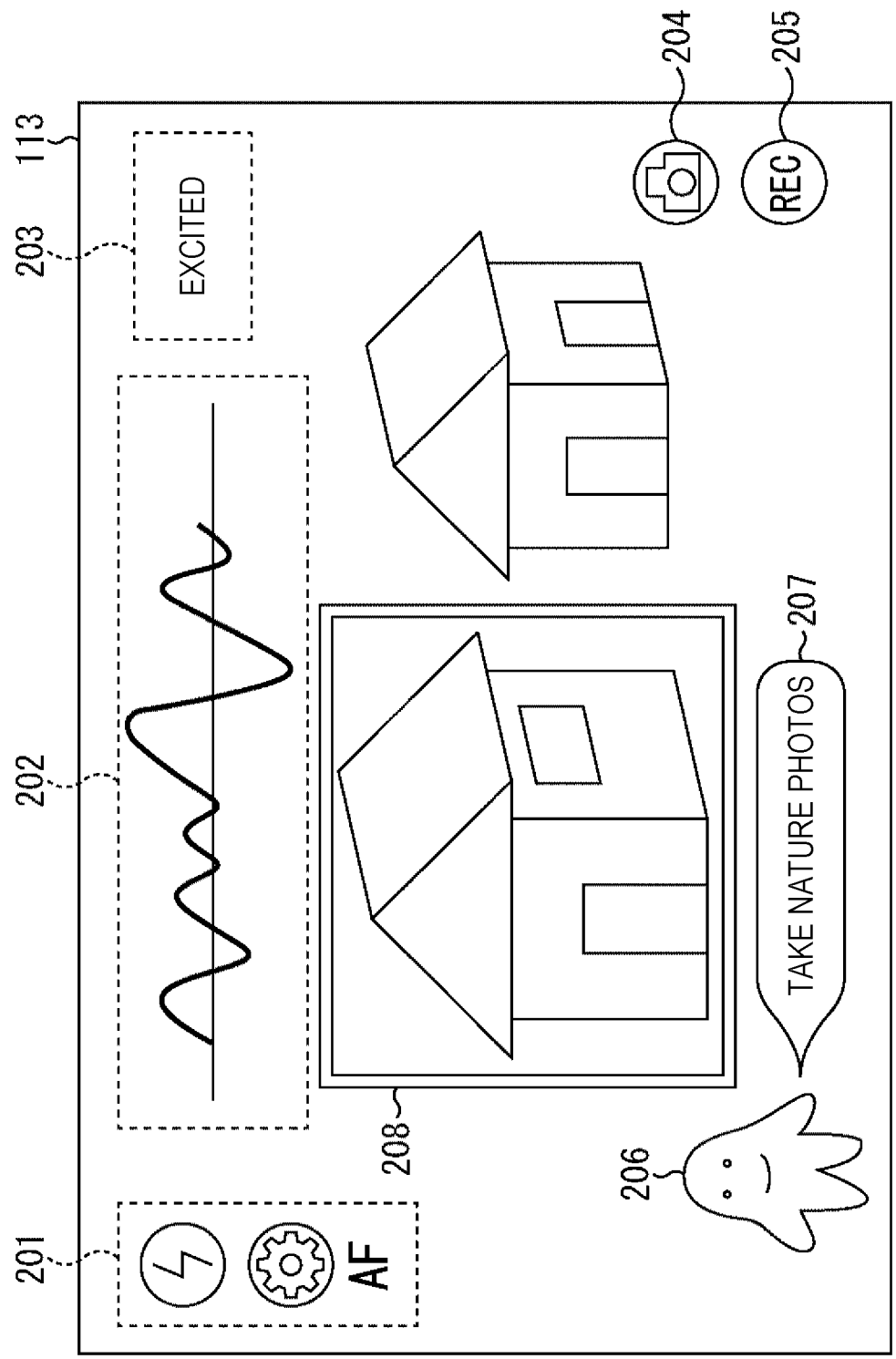
FIG. 4 is a diagram illustrating a display example of presenting a quest.

FIG. 4 illustrates a display example in a case where an image used to present a quest is displayed on the display unit 113 of the display apparatus 42.

In the center of the display unit 113, an image in which two houses are built is displayed as a preview image captured by the imaging unit 94. Thus, the preview image changes in various ways by the user who changes the imaging direction of the imaging unit 94 of the information processing apparatus 41 functioning as a camera.

In the display example of FIG. 4, an operation icon display portion 201, an electroencephalogram display portion 202, a dominant emotion display portion 203, a shooting button 204, a video record button 205, an avatar 206, a quest display portion 207, and a focus frame 208 are displayed on the preview image displayed on the whole display unit 113 in a superimposed manner.

In the operation icon display portion 201, operation buttons necessary for the shooting operation are displayed. In the operation icon display portion 201 of FIG. 4, three operation buttons are displayed from the top and provided with a strobe operation mode switching button for strobe shooting displayed in the upper part, a setting operation screen for switching to a setting operation screen displayed in the middle part, and an autofocus (AF) button for switching on/off of autofocus displayed in the lower part. The operation buttons displayed in the operation icon display portion 201 can be any button as long as they are necessary for the shooting operation, and examples thereof can include buttons for typical camera settings such as switching of the number of times of continuous shooting or settings of special shooting.

The electroencephalogram display portion 202 displays a real-time electroencephalogram waveform supplied from the electroencephalograph 31. The displayed waveform can be a waveform, which indicates the results after frequency analysis in time series or the magnitudes of the emotion estimation result in addition to the amplitudes of the illustrated electroencephalogram in time series. In a case where the waveform being displayed shows a multi-electrode electroencephalograph or a plurality of emotion estimation results, a plurality of waveforms can be displayed simultaneously. The presentation of such real-time biometric information and emotions makes it possible to achieve a presentation that does not make the user more bored.

The dominant emotion display portion 203 displays the type of dominant emotion having the highest emotion score among emotion information that is the emotion estimation results obtained on the basis of the electroencephalogram supplied from the electroencephalograph 31 and the biometric information supplied from the biometric sensor 32 in the server 43, and displays the emotion of "excited" in FIG. 4, which indicates that the "excited" emotion is the dominant emotion.

The shooting button 204 is a button that is operated by the user who photographs a still image. In a case where the shooting button 204 is operated, the imaging unit 94 controls an optical system (not shown) so that the subject in the focus frame 208 is focused and captures an image constituted as a still image.

The video record button 205 is a button operated by the user who records a moving image. In a case where the video record button 205 is operated, the imaging unit 94 records a moving image and the video record button 205 changes the color to a predetermined color, for example, red indicating that recording is in progress, and then the video record button 205 changes the color to the original color by the operation upon ending the recording.

The avatar 206 is an avatar, which corresponds to a user and is generated on the basis of emotion information as a result of analyzing electroencephalograms and biometric information by the information processing unit 93. In other words, the avatar 206 can be displayed to match the emotion so that the user can recognize, in one example, the state in emitting an aura, being irradiated while sweating, getting angry, or the like.

The quest display portion 207 presents information, which is a task for the user, to cause the user to achieve the reinforcement target behavior. In the quest display portion 207 of FIG. 4, "take a nature photo" is displayed. In this way, it is possible to give the user a sense of trust and familiarity with the instruction of the quest by showing the quest display portion 207 as the word of the avatar.

In other words, the user takes a photo to execute the task of "take a nature photo" displayed in the quest display portion 207.

The various tasks given to the user using the quest make it possible to control the situation or timing for measuring the electroencephalogram as necessary. In one example, the photograph is taken in a situation where the user is surprised by displaying a quest such as "take a photo of surprising situation", so the electroencephalograms and biometric information in the vicinity of the captured timing can be acquired as electroencephalograms or biometric information in a state where the user feels surprised.

In addition, the setting of the quest to a task to submit an image photographed by one shooting, the user concentrates on the shooting of one image, so more prominent electroencephalograms can be detected.

Furthermore, in such a case where the reinforcement target behavior is communication, the contents of the quest can be changed depending on an opponent or group to communicate with.

In one example, in the case of the quest such as "take a photo of surprising situation", the electroencephalogram measurement of the surprising situation is capable of being performed simply by causing the user to execute the task given as the presented quest, that is, by simply causing to perform the reinforcement target action, it is possible to detect the electroencephalogram in a surprising situation without being conscious of it.

In addition, in a case where it is desired to detect an electroencephalogram that is used for discrimination of a particular event-related potential, it is necessary for the quest to present the corresponding task.

In other words, the event-related potential is a typological electrophysiological response to internal and external stimuli and is a typical electroencephalogram waveform that occurs with a particular thought or cognition. The time necessary for particular thought or cognition is determined to some extent, so even in the electroencephalogram, the time from when an object is found to when it reaches the peak of the waveform is determined to some extent according to each condition. In one example, N170 for face cognition, N200 for the cognition of known images, P300 for the cognition of known objects, unnatural things, low attention, or the like, N400 for semantic discomfort, ERN for the recognition of errors, and so on are known.

Thus, in the case where it is desired to detect an electroencephalogram that is used as such an event-related potential, it is preferable to present a quest that is a task according to the discrimination contents of the event-related potential.

In addition, execution of the reinforcement target behavior by urging the reinforcement target behavior to which the specified condition is added by the quest makes it possible to detect the electroencephalogram in the specified condition. In one example, by urging the photographing in a certain mood or situation, it is possible to detect the electroencephalogram in such a mood or situation.

Moreover, the presentation of the quest can be performed not only by an image but also by a message such as a narration, and the quest can be presented by any method as long as the task can be urged by various ways such as light, vibration, sound, and fragrance. Thus, the device that presents the quest is not limited to the display unit 113 but can be various devices including a headphone that outputs a message such as narration, a lighting that emits light, a vibrator that generates vibration, a loudspeaker that produces sound, and a fragrance generator that emits scent.

In addition, the contents of the quest can be controlled by the user's charging, or the delivery of a quest in a particular event that increases the number of times can be received.

In other words, it is possible to urge the detection of the electroencephalogram of the desired condition by devising the quest. Consequently, the electroencephalogram of the user can be detected under various conditions, so it is possible to reflect the personality of the user on the avatar from multiple sides and accurately without causing the user's consciousness.

Although the above description is given of the example in which a quest is set to induce an emotion to measure an electroencephalogram or biometric information in a predetermined emotion, the quest capable of inducing the timing can be set to measure an electroencephalogram or biometric information in a predetermined timing. In other words, in the case of photographing, the quest can be an instruction for photographing timing (immediate, time-limited, specific date). In addition, the task can be such that one of the pictures photographed within a predetermined specified period is selected and submitted. In this case, the user takes a photograph at the desired timing within the specified period and submits a satisfactory image among photographed pictures, so it is possible to use the emotion estimation result when the user takes a photograph of the user's satisfactory image.

Furthermore, the contents presented by the quest can be changed depending on the situation where the user is placed. In one example, it is possible to estimate whether it is traveling, participating in an event, getting together what kind of friend from location information or action log, and to give a photographing instruction with timing and contents according to this estimation. In this event, the presentation can be changed by replacing the contents of the quest that previously presented with another. Alternatively, a plurality of quests can be presented simultaneously depending on the situation.

In addition, it is possible to control the timing of the reinforcement target behavior by devising the quest. In one example, in the case where the reinforcement target behavior is photographing, it is unnatural to continuously release the shutter for the purpose of the game as compared with a normal photographing habit, and so the effect of reinforcement of the reinforcement target behavior is difficult to achieve. Thus, a condition to limit the number of times of photographing in a similar way as usual one can be set using the quest, thereby appropriately reinforcing the reinforcement target behavior.

Further, the quest can be a guide for photographing a particular subject (photographic target), and in one example, a quest can be made to submit an image obtained by photographing a particular product such as a particular place, person, or car. This makes it possible to acquire naturally the emotion or reaction that the user has with respect to the particular photographic target without causing the user's consciousness.

In addition, the quest can be a task for specifying a photographing method, camera settings, and composition for a particular subject (photographic target), and in this way, it can be utilized as a promotion for a photographic target.

Furthermore, the quest can be a lecture (learning) on the reinforcement target behavior itself.

In other words, in the case where the reinforcement specifying behavior is camera photographing, it is possible to create and increase the user's photography experience or photographing opportunity by presenting a quest for urging the user who does not normally perform macro photographing to perform the macro photographing. The experience or opportunity of the macro photographing that is not normally performed makes it possible for the user to enjoy the execution of the reinforcement target behavior itself.

Moreover, although the above description is given of the example in which the avatar changes depending on the emotion estimation result on the basis of the sensing result of the biometric sensor 32, the change of the avatar can take into account not only the emotion estimation result based on the sensing result by the biometric sensor 32 but also the analysis result of the photographed subject.

In one example, if a subject in an image photographed by a user has many friends of the same generation or persons appearing in the user's social graph, it can be estimated that the subject is extrovert. In addition, in this event, the subject in the vicinity of the focus frame 208 can be analyzed by regarding the subject in the vicinity of the focus frame 208 as the user's attention subject rather than the entire image.

Further, the photograph (image) taken by the user is associated with the emotion at that time, so it can be utilized for marketing as user preference information for the subject of the photograph. In one example, information regarding whether it is positive, negative, known, or familiar is useful. In this event, the subject in the vicinity of the focus frame 208 can be analyzed by regarding the subject in the vicinity of the focus frame 208 as the subject of interest of the user rather than the entire photograph.

<Electroencephalogram Detection Timing>

The detection timing of the electroencephalogram is now described with reference to FIG. 5.

As described above, the behavior performed by the user for executing the task presented as the quest makes it possible to create the user's situation necessary for measuring the electroencephalogram.

The specific detection timing of the electroencephalogram is sufficient in the setting of the timing of executing the reinforcement target behavior as a reference, so in one example, the moment when the photographing that is the reinforcement target behavior is taken, that is, the timing of the shooting button 204 or the video record button 205 is operated can be used as a reference. In this case, the user is looking at the subject around the vicinity of the timing at which the photographing is taken, so there is a possibility of producing emotions regarding the subject.

In one example, as shown in the upper part of FIG. 5, in a case where the timing of operating the shooting button 204 or the video record button 205 is time t, the timing at which an electroencephalogram is necessary to be detected can be a period Z1 from the timing a predetermined time before time t to the time t as shown in the uppermost row of the upper part of FIG. 5.

Further, in one example, in the case where the timing of operating the shooting button 204 or the video record button 205 is time t, the timing at which an electroencephalogram is necessary to be detected can be periods Z2 and Z3 including predetermined both times before and after the time t as shown in the second and third rows from the top in FIG. 5.

Furthermore, in one example, in the case where the timing of operating the shooting button 204 or the video record button 205 is the time t, the timing at which the electroencephalogram is necessary to be detected can be a period Z4 including a predetermined time from time t-n which is n seconds before time ts as shown at the bottom from the top in FIG. 5.

Further, the specific detection timing of the electroencephalogram can be set on the basis of the timing at which the photographing that is the reinforcement target behavior is executed and the timing at which the imaging unit 94 of the information processing apparatus 41 is prepared. In this case, it takes time from when the subject is found to when the imaging unit 94 is prepared and the photographing is performed, so it is possible to detect the emotion at the time of finding it by calculating backward from the timing upon the photographing. Moreover, particularly in this case, not only the calculation backward from the timing at which the photographing is performed but also the setting of the timing at which the imaging unit 94 as a trigger can increase the accuracy. However, in this case, it is necessary to accurately detect the timing at which the imaging unit 94 is prepared by acceleration or the like.

In one example, as shown in the lower part of FIG. 5, in a case where the timing at which the imaging unit 94 of the information processing apparatus 41 is prepared is time tr and the timing at which the shooting button 204 or the video record button 205 is operated is time ts, the timing at which the electroencephalogram is necessary to be detected can be a period Z11 from time tr to time ts, as shown in the uppermost row of the lower part of FIG. 5.

Further, in one example, in the case where the timing at which the imaging unit 94 of the information processing apparatus 41 is prepared is time tr and the timing at which the shooting button 204 or the video record button 205 is operated is time ts, the timing at which the electroencephalogram is necessary to be detected is can be a period Z12 in which a predetermined time has elapsed from the time ts from the timing a predetermined time before the time tr as shown in the second row from the top in the lower part of FIG. 5.

Furthermore, in one example, in the case where the timing at which the imaging unit 94 of the information processing apparatus 41 is prepared is time tr and the timing at which the shooting button 204 or the video record button 205 is operated is time ts, the timing at which the electroencephalogram is necessary to be detected is can be a period Z13 including a predetermined time before and after the time tr, as shown in the third row from the top in the lower part of FIG. 5.

Further, in one example, in the case where the timing at which the imaging unit 94 of the information processing apparatus 41 is prepared is time tr and the timing at which the shooting button 204 or the video record button 205 is operated is time ts, the timing at which the electroencephalogram is necessary to be detected can be a period Z14 that has continued for a predetermined time from time tr, as shown in the bottom of the lower part of FIG. 5.

In other words, the electroencephalogram can be detected in a predetermined period using, as a reference, at least one of time tr, which is the timing at which the imaging unit 94 of the information processing apparatus 41 is held, or time ts, which is the timing at which the shooting button 204 or the video record button 205 is operated.

Furthermore, it is also preferable to use the electroencephalogram of a plurality of periods by using the information obtained at the time of the previous photographing.

Further, in addition to the above description, the electroencephalogram can be detected using the time tr as a timing based on an operation such as the attitude or gesture of the information processing apparatus 41 including the imaging unit 94 measured by the accelerometer, or the electroencephalogram can be detected at a timing other than the time tr that is set on the basis of the time tr. In addition, the electroencephalogram can be detected at the timing of looking through the viewfinder as the time tr, or the electroencephalogram can be detected at a timing other than the time tr with respect to the time tr. Furthermore, the timing after n seconds or n seconds before a particular behavior (photographing or the like) or the timing when the user has moved spatially can be used as a reference.

This makes it possible to obtain the emotion estimation result by regarding as the same attitude and measurement environment. Alternatively, an electroencephalogram in a predetermined period using, as a reference, a predetermined action is detected and a representative value or an average value in that period can be used.

Furthermore, a timing that varies depending on the subject to be photographed can be employed as the detection timing. This can be estimated by a quest or image analysis of the subject.

Moreover, the biometric information other than the electroencephalogram, which is detected by the biometric sensor 32 can be detected in a predetermined period on the basis of at least one of at the time tr that is the timing when the imaging unit 94 of the information processing apparatus 41 is prepared or the time ts that is the timing when the shooting button 204 or the video record button 205 is operated, which is similar to the electroencephalogram, and the detection of the biometric information may not be necessary to coincide with the timing at which the electroencephalogram is detected.

In addition, although the above description is given of the period during which the electroencephalogram is detected, the measurement of the electroencephalogram by the electroencephalograph 31 is normally performed, and the electroencephalogram measurement result continues to be supplied from the electroencephalograph 31 to the information processing apparatus 41. The detection timing of electroencephalogram described above is used to describe which period of the electroencephalogram signal that is normally measured is used by the information processing unit 93, and is not the measurement timing itself.

However, the measurement timing can be a normal measurement to avoid failing to notice as described above, or can be only a period longer than the period including the periods shown as the arrow in FIG. 5. This makes it possible to save power.

Furthermore, the quest can be displayed in a case where the detected emotion changes, the emotion does not change for a predetermined period or longer, and the like at the electroencephalogram detection timing. In other words, in one example, in a case where the emotion changes from "glad" to "sad", the quest of "falling into a sadness now" can be displayed, or in a case where the emotion remains "sad" for a certain period of time, the quest of "keep on feeling sad" can be displayed.

<Exif Format of Storing Electroencephalogram and Biometric Information in Association with Reinforcement Target Behavior>

An Exif format of storing the electroencephalogram detection result, biometric information, and emotion estimation result in association with the reinforcement target behavior is now described with reference to FIG. 6.

The electroencephalogram detection result, the biometric information, and the emotion estimation result are recorded in association with the reinforcement target behavior. In this example, the reinforcement target behavior is photographing, so the electroencephalogram detection result, the biometric information, and the emotion estimation result are recorded in association with an image captured by performing the photographing that is the reinforcement target behavior.

Thus, in the present disclosure, a format in which information at the time of photographing an image is stored in association with the captured image is used, and so the electroencephalogram detection result, the biometric information, and the emotion estimation result upon the photographing that is the reinforcement target behavior are stored.

More specifically, the information processing apparatus 41 equipped with a camera function used for photographing by the user records the electroencephalogram detection result, the biometric information, and the emotion estimation result obtained by performing the photographing that is the reinforcement target behavior in an exchangeable image file format (Exif) format.

However, the use of the Exif format in recording the electroencephalogram detection result, the biometric information, and the emotion estimation result obtained when the photographing that is the reinforcement target behavior is performed is only an example, but other formats than the Exif format are also used in the recording. In addition, the electroencephalogram detection result, the biometric information, and the emotion estimation result when the photographing that is the reinforcement target behavior is performed can be recorded in a separate file or recorded in a recording unit (DB, etc.) on the server.

The Exif format is a format compliant with the JPEG file format or the TIFF file format, and an area called an application marker segment is defined and stored in an area called application marker segment 1 (APP1). APP1 includes a plurality of directories called image file directory (IFD) holding data blocks that are a group of a plurality of tags compliant with the JPEG file format or the TIFF file format.

Figure 6:
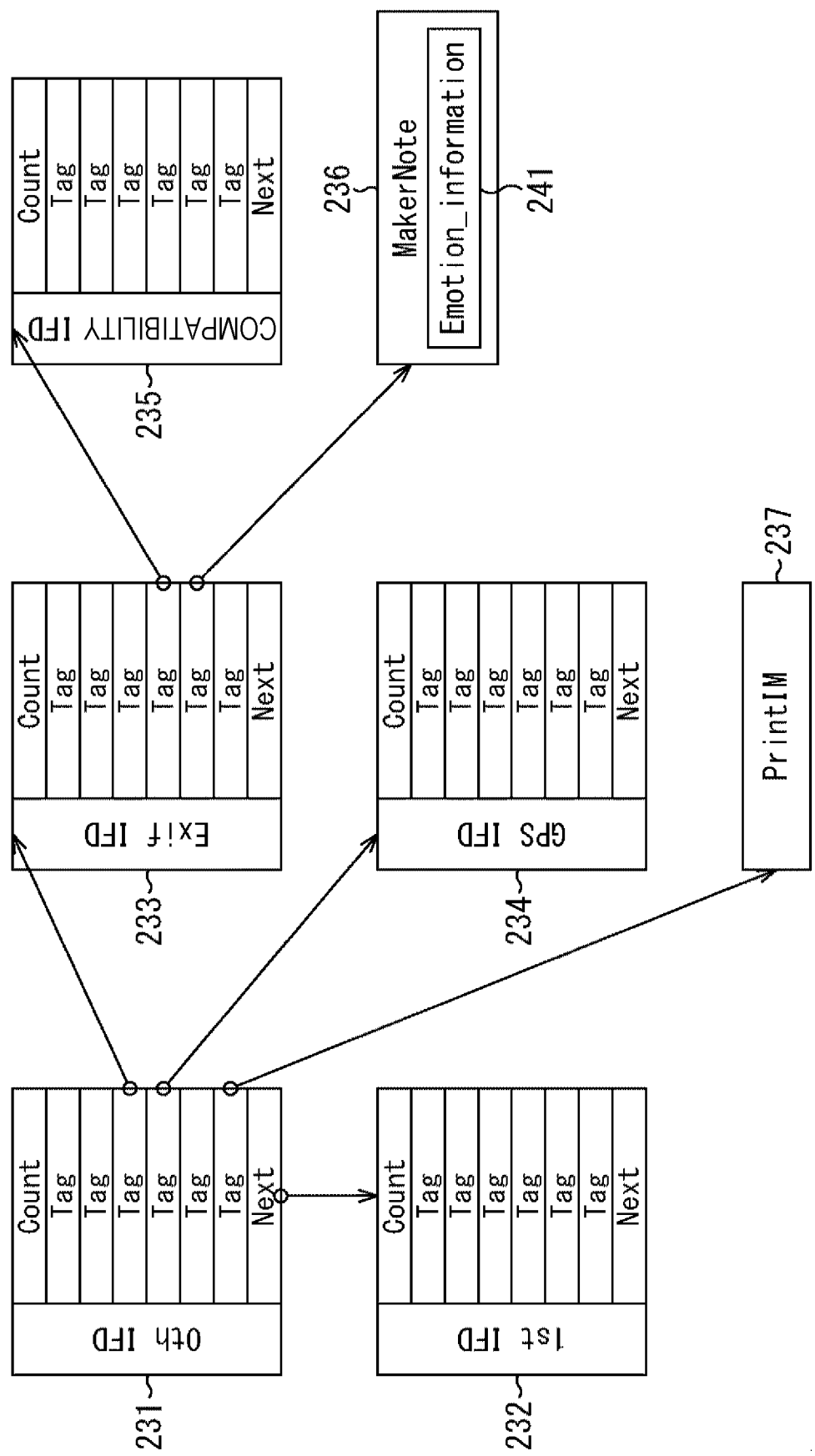
FIG. 6 is a diagram illustrated to describe an Exif format.

FIG. 6 shows the structure of APP1. APP1 includes 0th_IFD 231, 1st_IFD 232, Exif_IFD 233, GPS_IFD 234, compatibility_IFD 235, MakerNote 236, and PrintIM 237.

0th_IFD 231 is an IFD that stores information relating to the main image being captured.

1st_IFD 232 is an IFD that stores information relating to a thumbnail image.

Exif_IFD 233 is an IFD that stores information relating to an image at the timing upon capturing the image.

GPS_IFD 234 is an IFD that stores position information acquired by global positioning system (GPS) at the timing of capturing an image.

Compatibility_IFD 235 is an IFD that stores the compatibility information in the Exif format.

MakerNote 236 is an area that stores maker-specific information.

PrintIM 237 is not IFD, and stores information for delivering image information to be printed on a printer.

Among them, 0th_IFD 231, 1st_IFD 232, Exif_IFD 233, GPS_IFD 234, and compatibility_IFD 235 all store Count information, Tag information, and Nest information from the top. The Count information stores information indicating the number of Tag information stored in the IFD. The tag information stores tag data indicating various commands. In FIG. 6, six pieces of Tag information are stored for each IFD. The Next information stores a pointer that specifies the next IFD in a case where a tag is subsequently stored.

In addition, the third Tag information from the top of 0th_IFD 231 stores pointer information that specifies Exif_IFD 233, and the fourth Tag information from the top stores pointer information that specifies GPS_IFD 234. The sixth Tag information stores pointer information that specifies PrintIM 237, stores pointer information that specifies the next IFD indicated as Next, which specifies the address of 1st_IFD 232.

Furthermore, the fourth Tag information from the top of Exif_IFD 233 stores pointer information that specifies compatibility_IFD 235, and the fifth Tag information from the top stores pointer information that specifies MakerNote 236. The sixth Tag information from the top stores pointer information that specifies PrintIM 237.

In this description, MakerNote 236 stores the user's electroencephalogram detection result and biometric information, and stores Emotion_information 241 that is the emotion estimation result as Emotion_IFD.

Moreover, Emotion_information 241 used to store the user's electroencephalogram and biometric information can store the data itself as Emotion_IFD in MakerNote, or Emotion_information used to store the user's electroencephalogram detection result, biometric information, and emotion estimation result can be stored as a file separate from MakerNote, and MakerNote can store an ID or tag specifying this file and read out it. It is possible to handle the emotion estimation result in another place even if the single picture is distributed by embedding Emotion_information 241 in Exif. In addition, an avatar can be reconstructed by embedding Emotion_information 241 in Exif.

<Data Structure of Emotion_Information>

The data structure of Emotion_information 241 in FIG. 6 is now described with reference to FIG. 7.

Emotion_information 241 includes ID, Timestamp, Config_info, User_info, Brainwave_raw_1 to Brainwave_raw_n, Emo_info_1, and Emo_info_2 from the top of FIG. 7.

Emotion_information used to store the electroencephalogram detection result, the biometric information, and the emotion estimation result is recorded in association with the reinforcement behavior target, and in principle, in one example, it is attached for each photograph obtained by performing the photographing that is the reinforcement target behavior.

However, in a case where there is a plurality of photographs taken for the same quest, Emotion_information can be recorded for a group of a plurality of photographs taken for one quest. In this case, one piece of Emotion_information can be recorded in association with one quest, or the same Emotion_information can be recorded for each of a plurality of photographs taken for the same quest. In addition, in a case where a plurality of photographs is taken for one quest, in one example, a case where five photographs are taken during a certain event, each of emotion information of Exif (or another file) for each of the five photographs can be associated with one quest. In other words, plurality pieces of Emotion information can be generated for one quest.

In ID, information that individually identifies Emotion_information is recorded.

In Timestamp, time information relating to Emotion_information is recorded, and specifically, the start time of the electroencephalogram detection, the end time of the detection, and the time when the emotion estimation is performed are recorded.

In Config_info, information relating to the electroencephalograph 31 or the biometric sensor 32 is recorded. Moreover, the data structure of Config_info will be described later in detail with reference to FIG. 8.

In User_info, user information, in one example, information regarding gender, age (or age generation), nationality, and race is stored. Moreover, User_info can be information acquired through application software or can be managed on the side of the application software.

ID, Timestamp, Config_info, and User_info each include information capable of improving the accuracy of electroencephalogram detection and emotion estimation.

In Brainwave_raw_1 to Brainwave_raw_n, a plurality of raw data of the electroencephalogram detection result is recorded. The raw data is, in one example, the measurement results or the like of the electrodes 71-1 to 71-$n$ provided in the electroencephalograph 31. Specifically, it is data in which the amplitude indicating the potential difference is associated with the time information. Alternatively, it can be data in which the result obtained by performing frequency analysis, rather than the amplitude information, is associated with time information for each frequency. The recording of the raw data makes it is possible to perform electroencephalogram detection and emotion estimation again afterward. Moreover, in a case where Emo_info is recorded as the capacity increases, raw data may not be necessarily recorded. Moreover, the data structure of Brainwave_raw_n will be described in detail later with reference to FIG. 9.

In Emo_info_1 and Emo_info_2, information regarding the emotion estimation result is recorded. Only the emotion estimation result is recorded as metadata in Emo_info_1 and Emo_info_2, so it is possible to reduce the amount of information.

In addition, Emo_info_1 and Emo_info_2 can have different functions. In other words, Emo_info_1 can be recorded multiple times, or information of a plurality of emotion sets (plurality pieces of Emo_info_1) can be recorded in it depending on each application program. Furthermore, higher-order information obtained from the emotion set information (Emo_info_1) can be recorded in Emo_info_2.

In this description, the high-order information is the emotion set information depending on information directly used in the application program, such as dominant emotion and personality types. In a case where Emo_info_1 stores normal emotion set information and Emo_info_2 stores information obtained from Emo_info_1, it is possible to further reduce the amount of information when only Emo_info_1 is stored. Details of the data structures of Emo_info_1 and Emo_info_2 will be described later with reference to FIG. 10.

<Data Structure of Config_Info>

The data structure of Config_info in which information of the electroencephalograph 31 or the biometric sensor 32 is stored is now described with reference to FIG. 8.

Config_info includes Eeg_Type, Eeg_ele_num, Sensor_1 to Sensor_n, Position, Attitude, Application_ID, and Meta_version.

In Eeg_Type, information of model number or version indicating the type of the electroencephalograph 31 is stored.

In Eeg_ele_num, the number of electrodes 71 of the electroencephalograph 31 is stored.

In Sensor_1 to Sensor_n, in a case where there is the biometric sensor 32 used in conjunction with the electroencephalograph 31, information regarding the biometric sensor 32 is stored.

In Position, position information by, in one example, GPS or the like upon detection of the electroencephalogram is stored.

In Attitude, information indicating the user's attitude is stored. In one example, in a case where the biometric sensor 32 is provided with an accelerometer or the like, information obtained by using the result detected by the accelerometer is used as the user's attitude.

In Application_ID, an ID used to identify the application program used upon execution of the electroencephalogram detection is stored.

In Meta_version, version information of metadata is stored.

<Data Structure of Brainwave_Raw_n>

Figure 9:
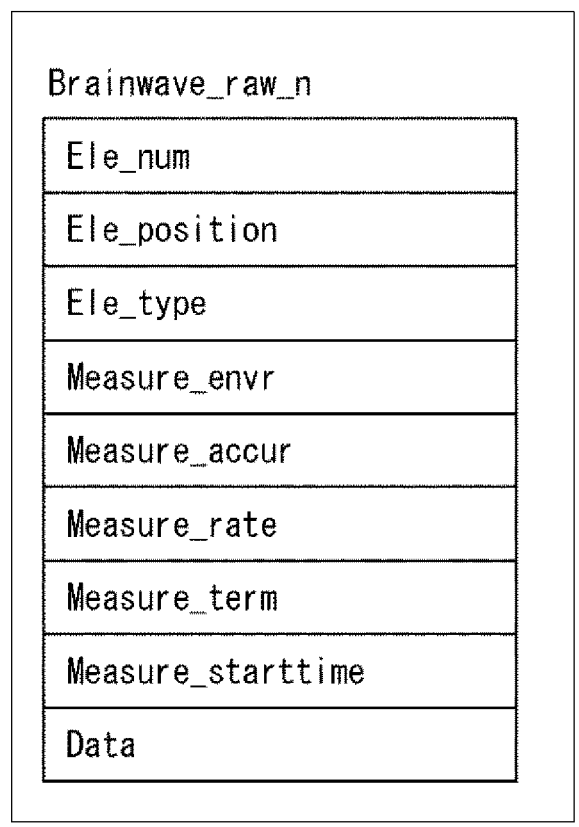
FIG. 9 is a diagram illustrated to describe a data configuration of Brainwave_raw_n.

The data structure of Brainwave_raw_n that stores the raw data of the electroencephalogram detected by the electrode 71-n is now described with reference to FIG. 9.

Brainwave_raw_n includes Ele_num, Ele_position, Ele_type, Measure_envr, Measure_accur, Measure_rate, Measure_term, Measure_starttime, and Data.

In Ele_num, the number that identifies the electrodes 71-1 to 71-n is stored.

In Ele_position, information regarding the position of the electrode is stored. The information regarding the position of the electrode is, in one example, information regarding the position of the electrode in the international 10-20 system, which is the global standard.

In Ele_type, information regarding the type of electrodes is stored. The type of electrodes is, in one example, information such as whether wet or dry electrode.

In Measure_envr, information relating to the measurement environment is stored. The information relating to the measurement environment is, in one example, information such as environmental temperature, body temperature, and the presence or absence of sweating.

In Measure_accur, information regarding the measurement accuracy is stored. The information regarding the measurement accuracy is, in one example, an absolute value estimated from a signal to noise (S/N) ratio of the electrode 71-n or information regarding enable or disable state.

In Measure_rate, information regarding a measurement cycle is stored. The information regarding the measurement cycle information is, in one example, a frame rate (fps).

In Measure_term, information regarding the measurement time or the number of measurement points (msec) is stored.

In Measure_starttime, information regarding the measurement start time is stored.

In Data, information regarding an absolute value of the potential for each measurement cycle is stored. In other words, in one example, upon measurement at 60 fps for 1 second, the potentials at the time of measurement such as 5 mV, 8 mV, −3 mV, and so on are recorded in Data as a continuous data string.

<Data Structure of Emotion_info_1 and Emotion_info_2>

The data structure of Emotion_info_1 that stores the emotion estimation result as metadata and the data structure of Emotion_info_2 that stores higher-order information further estimated from the emotion estimation result are now described with reference to FIG. 10.

The data structure of Emotion_info_1 shown in the upper part of FIG. 10 is now described.

Emotion_info_1 includes Emo_type_set and Emo_type1_value to Emo_typen_value.

In Emo_type_set, information used to identify the emotion set is stored.

In Emo_type1_value to Emo_typen_value, information used to identify the emotion set being estimated is stored. The emotion set is different for each application program. In a case where the reinforcement target behavior is photographing, in one example, five types of emotions of "excited", "mysterious", "impressed", "surprise", and "discovery" relating to the photographing are estimated, and the score including estimated values of the emotions is stored in each of Emo_type1_value to Emo_typen_value. The emotion estimation result is stored, for example, by regarding each strength (0-100) or a proportion (proportion in assuming that total is 100) as a score (estimated value) for each estimated emotion type.

The data structure of Emotion_info_2 shown in the lower part of FIG. 10 is now described.

Emotion_info_2 includes Strongest_type, Strongest_type_value, Weekest_type, Weekest_type_value, and Mind_type.

In Strongest_type, information used to specify the type of the most dominant emotion (emotion with the highest estimated value) among Emo_type1 to Emo_typen is stored.

In Strongest_type_value, a score (estimated value) of the dominant emotion is stored.

In Weekest_type, information used to specify the type of the emotion having the lowest score (estimated value) among Emo_type1 to Emo_typen is stored.

In Weekest_type_value, the estimated value of the emotion having the lowest score (estimated value) is stored.

In Mind_type, information regarding the personality analyzed from the emotion distribution of each emotion set is stored.

<Emotion Estimation Result and Change in Avatars>

Examples of the emotion estimation result and change in avatars are now described.

The avatar 206 shown in the display example of FIG. 4 is changed and displayed on the basis of the electroencephalogram detection information and biometric information, which are detected in the long term.

In this example, the avatar 206 grows while changing its form on the basis of the electroencephalogram detection information and the biometric information upon the repetitive shooting, for example, while the processing of taking the photograph by the user is repeated depending on the repetitive quest.

Figure 11:
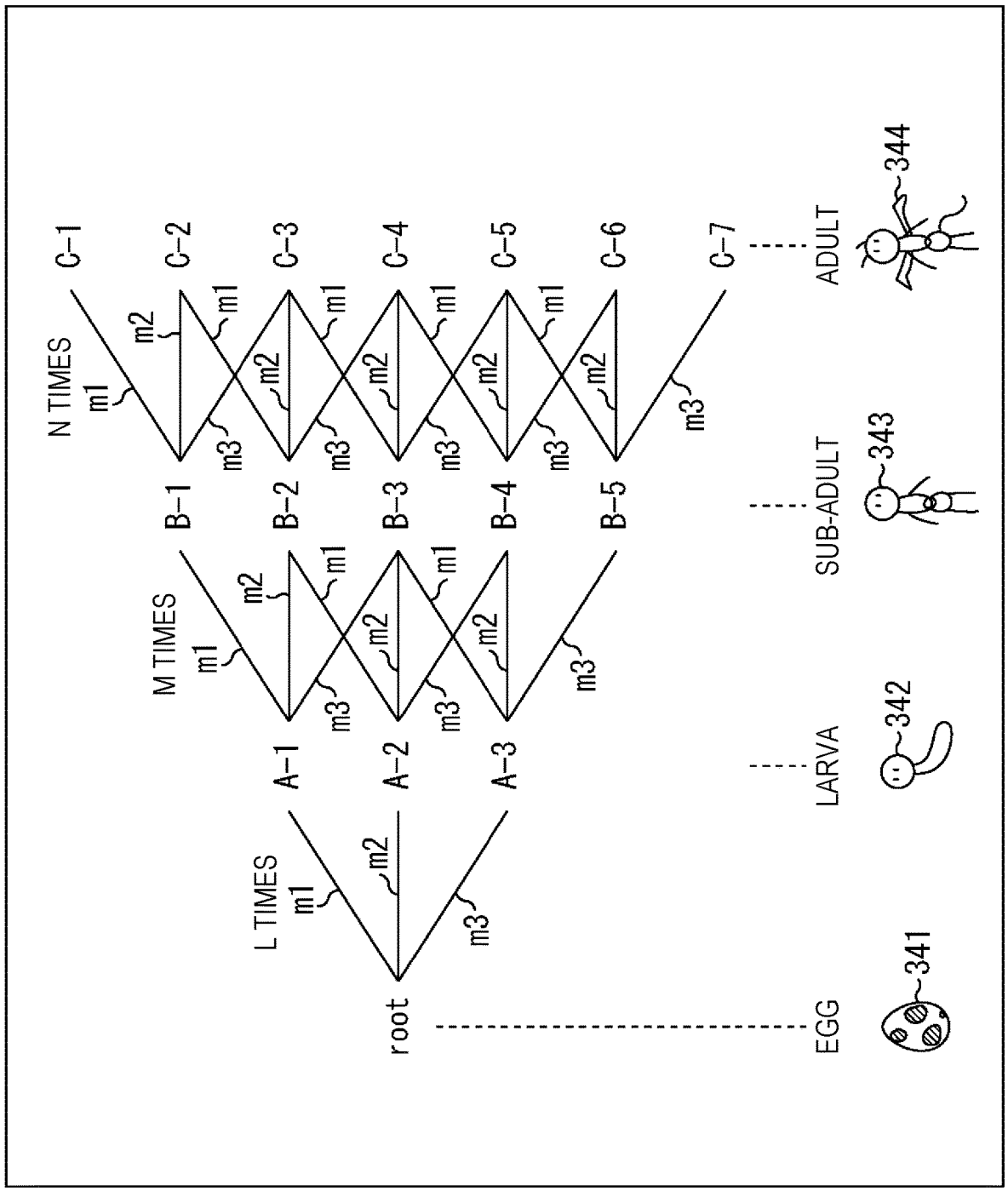
FIG. 11 is a diagram illustrated to describe a change in avatars changed in the form of a dendrogram.

In one example, as shown in the lowermost part of FIG. 11, in a case where the photographing that is the reinforcement target behavior is repeatedly performed and the emotion estimation result satisfies a predetermined condition, the avatar 206 changes from an egg (root) 341 to a larva 342, from the larva 342 to a sub-adult 343, from the sub-adult 343 to an adult 344, and then changes to various forms as an adult 344 after changing to the adult 344.

In other words, in the lowermost stage of FIG. 11, in one example, the avatar 206 is started from the egg (root) 341, and when a predetermined emotion is repeated L times, it changes to the larva 342, and then when the predetermined emotion is repeated M times, it changes to the sub-adult 343, and further when the predetermined emotion is repeated N times, it changes to the adult 344.

Further, the larva 342 has different forms depending on the type of the emotion repeated L times, and similarly, the sub-adult 343 also has different forms depending on the type of the emotion repeated M times. The adult 344 also has different forms depending on the type of the emotion repeated N times.

In other words, there are three types of dominant emotions of emotions m1 to m3, and the avatar 206 changes while growing in the form of a dendrogram, in one example, shown in the upper part of FIG. 11 depending on the types of emotions that are repeated a predetermined number of times. Moreover, A-1 to A-3 in FIG. 11 represent the types of the larva 342 of the avatar 206, B-1 to B-5 in FIG. 11 represent the types of the sub-adult 343 of the avatar 206, and C-1 to C-9 in FIG. 11 represent the types of the adult 344 of the avatar 206.

More specifically, as shown in the upper part of FIG. 11, in the case where the emotion m1 is repeated L times as the dominant emotion in the state of the egg (root) 341, the avatar 206 changes to the type A-1 of the larva 342. In addition, in the case where the emotion m2 is repeated L times as the dominant emotion in the state of the egg (root) 341, the avatar 206 changes to the type A-2 of the larva 342. Furthermore, in the case where the emotion m3 is repeated L times as the dominant emotion in the state of the egg (root) 341, the avatar 206 changes to the type A-3 of the larva 342.

Further, in the case where the emotion m1 is repeated M times as the dominant emotion in the state of type A-1 of the larva 342, the avatar 206 changes to the type B-1 of the sub-adult 343. Furthermore, in the case where the emotion m2 is repeated M times as the dominant emotion in the state of the type A-1 of the larva 342, the avatar 206 changes to the type B-2 of the sub-adult 343. In addition, in the case where the emotion m3 is repeated M times as the dominant emotion in the state of type A-1 of the larva 342, the avatar 206 changes to the type B-1 of the sub-adult 343.

Furthermore, in the case where the emotion m1 is repeated M times as the dominant emotion in the state of type A-2 of the larva 342, the avatar 206 changes to the type B-2 of the sub-adult 343. Furthermore, in the case where the emotion m2 is repeated M times as the dominant emotion in the state of the type A-2 of the larva 342, the avatar 206 changes to the type B-3 of the sub-adult 343. In addition, in the case where the emotion m3 is repeated M times as the dominant emotion in the state of type A-2 of the larva 342, the avatar 206 changes to the type B-4 of the sub-adult 343.

In addition, in the case where the emotion m1 is repeated M times as the dominant emotion in the state of type A-3 of the larva 342, the avatar 206 changes to the type B-3 of the sub-adult 343. Furthermore, in the case where the emotion m2 is repeated M times as the dominant emotion in the state of the type A-3 of the larva 342, the avatar 206 changes to the type B-4 of the sub-adult 343. In addition, in the case where the emotion m3 is repeated M times as the dominant emotion in the state of type A-3 of the larva 342, the avatar 206 changes to the type B-5 of the sub-adult 343.

Still further, in the case where the emotion m1 is repeated N times as the dominant emotion in the state of type B-1 of sub-adult 343, the avatar 206 changes to the type C-1 of the adult 344. Furthermore, in the case where the emotion m2 is repeated N times as the dominant emotion in the state of the type B-1 of sub-adult 343, the avatar 206 changes to the type C-2 of the adult 344. In addition, in the case where the emotion m3 is repeated N times as the dominant emotion in the state of type B-1 of sub-adult 343, the avatar 206 changes to the type C-3 of the adult 344.

Similarly, in the case where the emotions m1, m2, and m3 are repeated N times as the dominant emotions in the state of the type B-2 of the sub-adult 343, the avatar 206 changes to types C-2, C-3, and C-4, respectively, of the adult 344.

In addition, in the case where the emotions m1, m2, and m3 are repeated N times as the dominant emotions in the state of the type B-3 of the sub-adult 343, the avatar 206 changes to types C-3, C-4, and C-5, respectively, of the adult 344.

Further, in the case where the emotions m1, m2, and m3 are repeated N times as the dominant emotions in the state of the type B-4 of the sub-adult 343, the avatar 206 changes to types C-4, C-5, and C-6, respectively, of the adult 344.

In addition, in the case where the emotions m1, m2, and m3 are repeated N times as the dominant emotions in the state of the type B-5 of the sub-adult 343, the avatar 206 changes to types C-5, C-6, and C-7, respectively, of the adult 344.

In other words, in the state of the egg (root) 341, the emotion estimation is performed by performing a forced target behavior depending on the quest, and the processing of obtaining the emotion estimation result is repeated, and so the number of times of each of the emotions m1 to m3 of the dominant emotion, which is the emotion estimation result, is counted. Then, in the case where the counted number of times is repeated L times, M times, or N times, which is a predetermined number of times, the avatar 206 changes its form.

<Exemplary Configuration of Short-Term Change Table Used to Store Emotion Estimation Result>

A short-term change table used to store the emotion estimation result is now described with reference to FIG. 12.

The short-term change table is a table managed by the information processing unit 93 of the information processing apparatus 41 and is a table managed on the basis of the emotion estimation result obtained by being supplied to the server 43 on the basis of the electroencephalogram detection result and biometric information supplied from the electroencephalograph 31 and the biometric sensor 32. Moreover, in the present disclosure, the description is made assuming that the short-term change table is a table managed by the information processing unit 93, but it can be managed by the server 43.

In one example, as illustrated in FIG. 12, the short-term management table includes an avatar type column, an emotion column, and a score column from the left in the figure.

In the avatar type column, information indicating the type of the current avatar 206 is stored, and FIG. 12 illustrates the egg (root) 341 of FIG. 11.

Further, in the emotion column, the types of emotions that are capable of being acquired as the emotion estimation result are listed from the top. In FIG. 12, the types of emotions are listed in the order of emotions m1, m2, and m3 from the top.

In the score column, scores associated with the types of emotions of the emotion estimation result are recorded, and in this case, 10, 60, and 30 are recorded from the top.

Thus, FIG. 12 shows that the emotion m1 is detected as a score of 10, the emotion m2 is detected as a score of 60, and the emotion m3 is detected as a score of 30 on the basis of the electroencephalogram detection result and the biometric information at the timing when the photographing that is the reinforcement target behavior is performed in the case where the avatar 206 is in the state of the egg (root) 341. In other words, the short-term change table of FIG. 12 shows that the emotion m2 having the highest score, which is the score of 60, is the dominant emotion. Moreover, the short-term change table is substantially information obtained by adding the avatar type information to the information of Emo_info_1 described with reference to FIG. 10.

<Exemplary Configuration of Long-Term Change Table Used to Store Emotion Estimation Result>

An exemplary configuration of a long-term change table is now described with reference to FIG. 13.

The long-term change table is a table managed by the information processing unit 93 of the information processing apparatus 41, and accumulates the results of the short-term change table.

The long-term management table is provided with an avatar type column, an emotion column, and a number-of-times column from the left in the figure as shown in both upper and lower parts of FIG. 13.

In the avatar type column, information indicating the type of the current avatar 206 is stored, and it shows that there is the egg (root) 341 in both upper and lower parts of FIG. 13.

Further, in the emotion column, the types of emotions that are capable of being acquired as the emotion estimation result are listed from the top. In FIG. 13, the types of emotions are listed in the order of emotions m1, m2, and m3 from the top.

In the number-of-times column, the number of times of emotions as the current dominant emotion obtained on the basis of the information of the short-term change table, which is generated every time the photographing as the reinforcement target behavior is taken, is recorded.

In other words, in one example, as shown in the upper part of FIG. 13, in a case where the number of times that the emotion m1 is the dominant emotion is two times, the number of times that the emotion m2 is the dominant emotion is four times, and the number of times that the emotion m3 is the dominant emotion is three times, when the short-term change table of FIG. 12 described above is supplied, the information processing unit 93 regards the emotion m2 as the dominant emotion on the basis of the information regarding the short-term change table of FIG. 12. Then, as shown in the lower part of FIG. 13, the information processing unit 93 sets the count of the emotion m2 regarded as the dominant emotion to five by incrementing it by one.

Furthermore, the information processing unit 93 determines whether or not it is time to change the avatar 206 on the basis of the number of times in the long-term change table every time the short-term emotion table is supplied. If the predetermined number of times is exceeded, the information processing unit 93 changes the type of avatar 206 and updates the long-term change table.

In one example, in a case where the number of times L in FIG. 11 is five times and the number of times of the emotion m2 is five times as shown in the lower part of FIG. 13, the state of the avatar 206 is changed and the long-term change table is updated.

In other words, in a case where the emotion m2 is repeated L times when the avatar 206 is in the state of the egg (root) 341, the avatar 206 changes to the type A-2 of the larva 342, when it changes as shown in FIG. 11. Thus, as illustrated in FIG. 14, the information processing unit 93 changes the avatar type column to the type A-2, resets the number of times the emotions m1, m2, and m3 are the dominant emotions to zero, and then, every time a new short-term change table is supplied, the long-term change table is updated and changed as described above.

In this way, the information processing unit 93 controls the change of the avatar 206 by managing the short-term change table and the long-term change table. Moreover, in the case where the avatar 206 changes to the adult 344, the information processing unit 93 can return to the type B-1 in a case where the type of the avatar 206 in the long-term change table changes to C-1 and C-2, can return to the type B-2 in a case where the type of the avatar 206 changes to C-3, can return to the type B-3 in a case where the type of the avatar 206 returns to C-4, can return to the type B-4 in a case where the type of the avatar 206 changes to C-5, and can return to the type B-1 in a case where the type of avatar 206 changes to C-6 or C-7. In other words, the type of the avatar 206 changes to the state of the adult 344, but in the long-term change table, returns to the state of the sub-adult 343 close to the current adult 344, the avatar 206 to be presented can be changed by keeping the state in which the avatar 206 remains the state of the adult 344 by maintaining the state in which the avatar 206 can change from the sub-adult 343 to the adult 344 depending on the number of times of the dominant emotion.

The processing of changing the avatar 206 using the above-described long-term change table is referred to as long-term emotion feedback processing.

<Display Example of Image Presenting Avatar>

A display example of an avatar for urging the reinforcement target behavior depending on the long-term change table is now described with reference to FIG. 15.

As described above, in the information processing system of the present disclosure, the reinforcement target behavior is urged by repeatedly presenting a quest, and the short-term change table is repetitively created on the basis of the electroencephalogram detection result and biometric information at the timing when the reinforcement target behavior is performed. Then, every time the short-term change table is created, the long-term change table is updated, and the avatar 206 changes on the basis of the long-term change table.

The user repeats the reinforcement target behavior for the purpose of changing the avatar 206. Thus, every time the reinforcement target behavior is performed, that is, the short-term change table is created, and it is necessary to repeatedly present the avatar 206 associated with the state of the long-term change table being changed.

Figure 15:
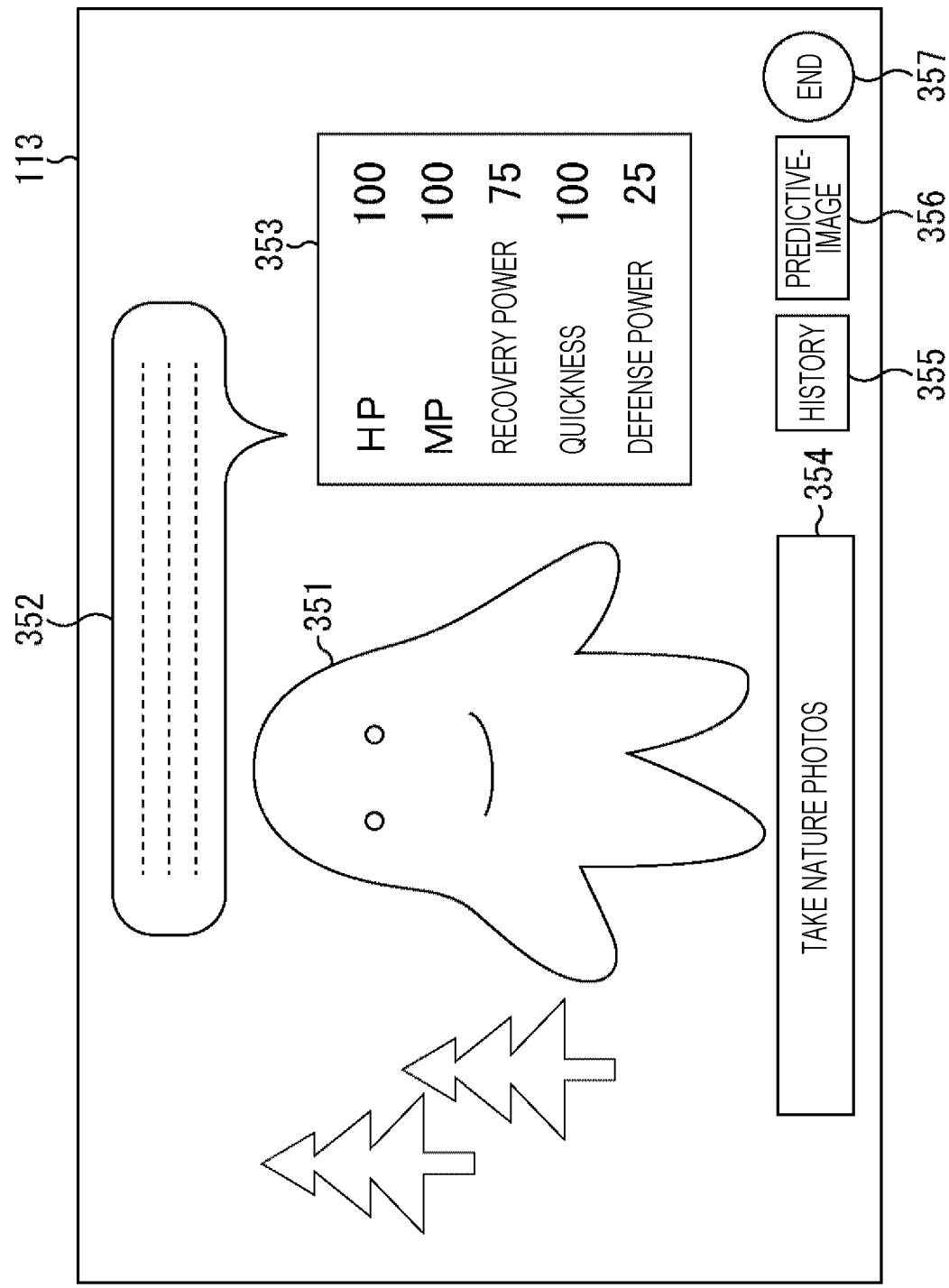
FIG. 15 is a diagram illustrated to describe a display example of presenting an avatar.

In other words, FIG. 15 is a display example of presenting the avatar 206 associated with the current long-term change table every time the reinforcement target behavior is performed.

As shown in the center of FIG. 15, an avatar 351 associated with the current long-term change table is displayed at the center of the display unit 113. In addition, a comment portion 352 provided for the user as the avatar 351 is placed above the avatar 351 and a comment such as advice for urging the reinforcement target behavior can be displayed. In addition, on the right side of the avatar 351, a state display portion 353 of the avatar 351 is provided, and in FIG. 15, HP (hit point) of 100 points and MP (magic power) of 100 points, recovery power of 75 points, quickness of 100 points, and defense power of 25 points are displayed from the top.

Moreover, HP, MP, recovery power, quickness, and defense power displayed in the state display portion 353 can be, in one example, a value obtained by multiplying the score of the emotion estimation result by a predetermined coefficient as illustrated in FIG. 16.

In other words, in the case where the emotion estimation results are a set of five types of emotions of "excited", "mysterious", "impressed", "I found it", and "great", the respective values of 10 times, 2 times, 5 times, 5 times, and 5 times for the scores of the five types of emotions can be used as the respective points of HP, MP, recovery power, quickness, and defense power.

More specifically, as shown in the left part of FIG. 16, in a case where the scores of "excited", "mysterious", "impressed", "I found it", and "great" are 10, 50, 15, 20, and 5, respectively, the points of HP, MP, recovery power, quickness, and defense power are 100 (=10×10), 100 (=50× 2), 75 (=15×5), 100 (=20×5), and 25 (=5×5), respectively.

Further, in FIG. 15, a quest display portion 354 is provided below the avatar 351, and a quest of "take a nature photo" is displayed.

In addition, on the right side of the quest display portion 354, a history image display button 355, a predictive-image display button 356, and an end button 357 are displayed from the left.

The history image display button 355 is operated when a history image representing the past history of the avatar 351 is displayed. Moreover, the history image will be described later with reference to FIGS. 17 and 18.

The predictive-image display button 356 is operated when a predictive image representing a predictive future change from the past history of the avatar 351 is displayed. Moreover, the predictive image will be described later with reference to FIGS. 19 and 20.

The end button 357 is a button that is operated when the display of the image presenting the avatar of FIG. 15 terminates and returns to the image of displaying the quest of FIG. 4.

As illustrated in FIG. 15, it is possible to check the change in the avatar 351 associated with the long-term change table, which is displayed every time the reinforcement target behavior is performed. If there is no change, it is possible to stimulate the desire to make a change, and if there is a change, it is possible for the joy of the change to cause to be felt.

Further, the change in avatars can be one reflecting the reinforcement target behavior executed by the user, so the presentation of the change in avatars that the user empathizes with increases the willingness to change the avatar, resulting in reinforcing the reinforcement target behavior.

<First Display Example of History Image>

A first display example of the history image is now described with reference to FIG. 17.

Figure 17:
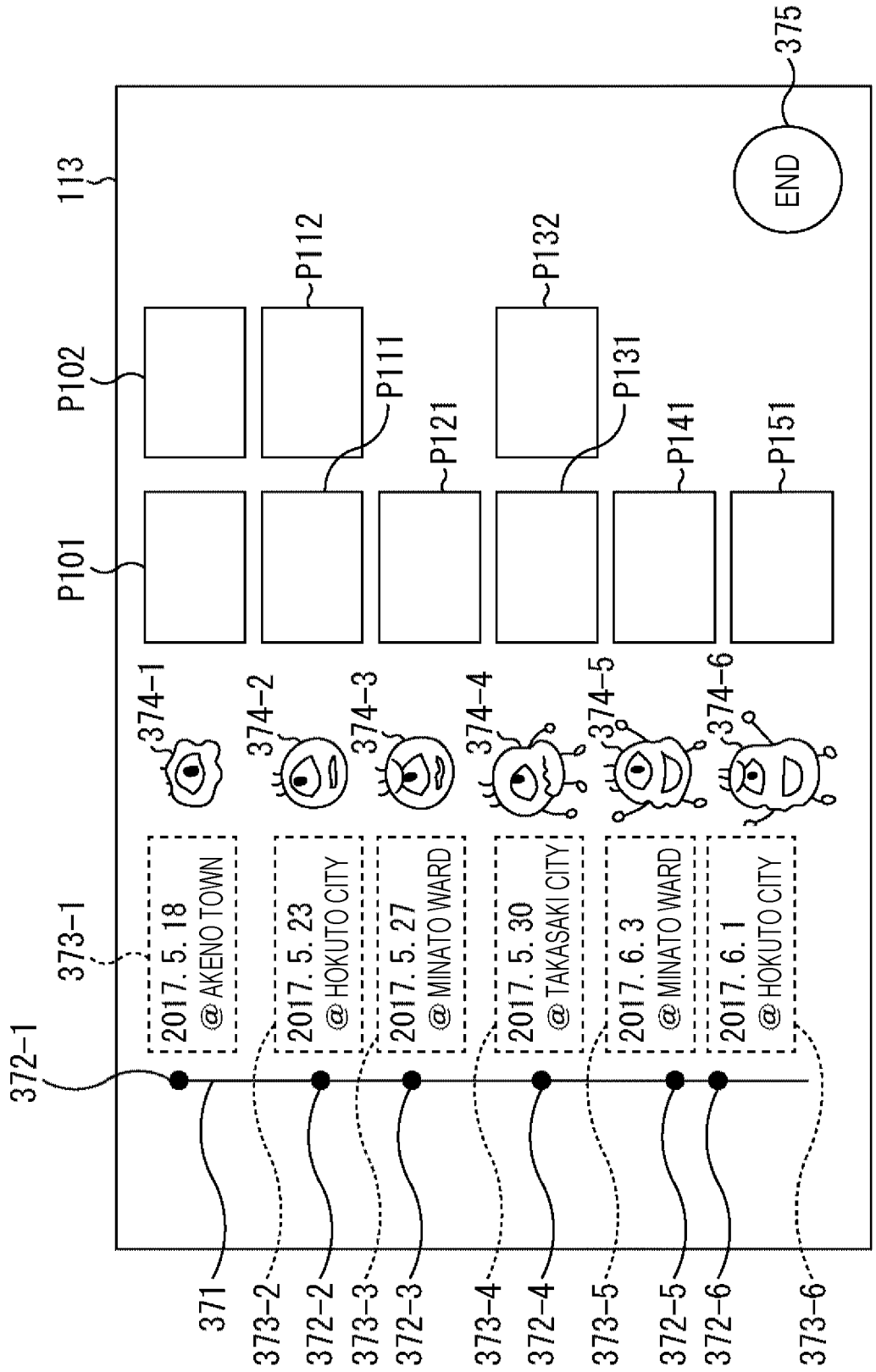
FIG. 17 is a diagram illustrated to describe a display example of a history image.

The history image as shown in FIG. 17 is displayed, in one example, when the history image display button 355 in FIG. 15 is operated.

In the history image of FIG. 17, on the left side of the display image, the date when the photographing that is the reinforcement target behavior is displayed in time series from the top as points 372-1 to 372-6 on a time series bar 371. Date display portions 373-1 to 373-6 corresponding to the points 372-1 to 372-6 are displayed, respectively. In addition, on the right side of the date display portions 373-1 to 373-6, avatars 374-1 to 374-6 at the dates are displayed, respectively. Furthermore, on the right side of avatars 374-1 to 374-6, images captured by the photographing that is the reinforcement target behavior at the corresponding dates are displayed.

In other words, in FIG. 17, it shows that the avatar 374-1 is represented in a case where images P101 and P102 are photographed in Akeno town at the date, May 18, 2017, indicated by the point 372-1 on the time series bar 371.

Further, it shows that the avatar 374-2 is represented in a case where images P111 and P112 are photographed in Hokuto city at the date, May 23, 2017, indicated by the point 372-2 on the time series bar 371.

Furthermore, it shows that the avatar 374-3 is represented in a case where images P121 is photographed in Minato ward at the date, May 27, 2017, indicated by the point 372-3 on the time series bar 371.

Further, it shows that the avatar 374-4 is represented in a case where images P131 and P132 are photographed in Takasaki city at the date, May 30, 2017, indicated by the point 372-4 on the time series bar 371.

Furthermore, it shows that the avatar 374-5 is represented in a case where images P141 is photographed in Minato ward at the date, Jun. 3, 2017, indicated by the point 372-5 on the time series bar 371.

Furthermore, it shows that the avatar 374-6 is represented in a case where images P151 is photographed in Hokuto city at the date, Jun. 7, 2017, indicated by the point 372-6 on the time series bar 371.

Furthermore, the end button 375 is provided at the lower right of the history image. The end button 375 is operated when the display of the history image terminates and returns to the display image of the presentation that urges the reinforcement target behavior depending on the long-term change table of FIG. 15.

In other words, the display of the history image shown in FIG. 17 makes it possible for the user to check in a time series how the avatar 374 has changed by the reinforcement target behavior that has been performed so far. In addition, in this event, it is possible to check how the image has changed when a certain image is photographed at a certain date and place.

<Second Display Example of History Image>

A second display example of the history image is now described with reference to FIG. 18.

Figure 18:
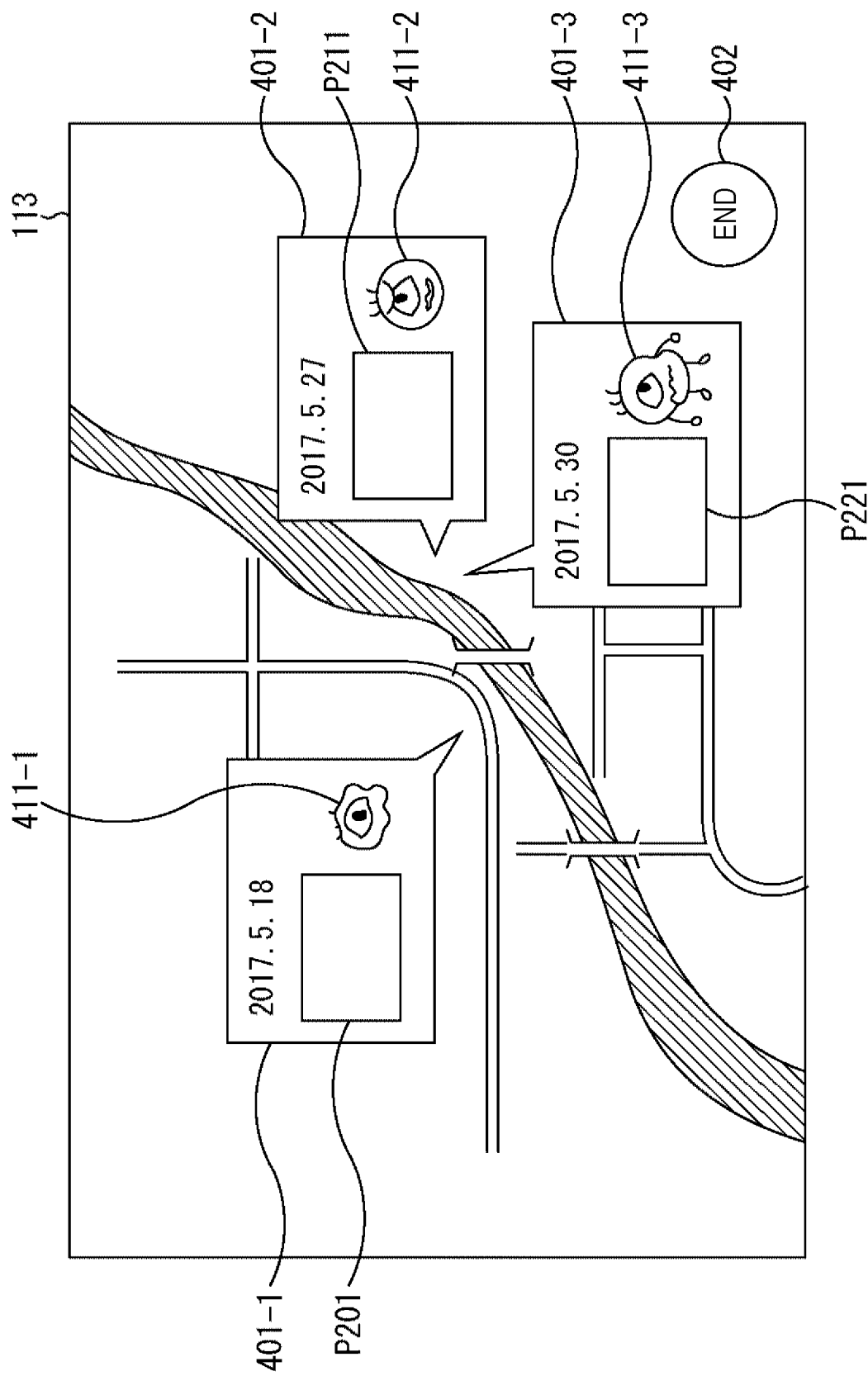
FIG. 18 is a diagram illustrated to describe a display example of a history image.

The history image as shown in FIG. 18 may be displayed, in one example, when the history image display button 355 in FIG. 15 is operated.

In the history image of FIG. 18, a map is displayed on the entire display image, and history display portions 401-1 to 401-3 are displayed in association with the positions where the reinforcement target behavior is performed on the map.

The history display portion 401-1 indicates a position near the center-left side on the map in the figure. In addition, the upper part of the history display portion 401-1 indicates that the date of this history is May 18, 2017. Furthermore, the lower part of the history display portion 401-1 indicates that an image P201 is captured when the history is recorded, and an avatar 411-1 at that time is shown on the right side of the image P201.

The history display portion 401-2 indicates a position near the center-right upper part on the map in the figure. In addition, the upper part of the history display portion 401-2 indicates that the date of this history is May 27, 2017. Furthermore, the lower part of the history display portion 401-2 indicates that an image P211 is captured when the history is recorded, and an avatar 411-2 at that time is shown on the right side of the image P211.

The history display portion 401-3 indicates a position near the center-right lower part on the map in the figure. In addition, the upper part of the history display portion 401-3 indicates that the date of this history is May 30, 2017. Furthermore, the lower part of the history display portion 401-3 indicates that an image P221 is captured when the history is recorded, and an avatar 411-3 at that time is shown on the right side of the image P221.

Furthermore, an end button 402 is provided at the lower right of the history image in FIG. 18. The end button 402 is operated when the display of the history image terminates and returns to the image that presents the avatar of FIG. 15.

In other words, the display of the history image shown in FIG. 18 makes it possible for the user to check in a time series how the avatar 411 has changed by the reinforcement target behavior that has been performed so far. In addition, in this event, it is possible to check how the image has changed when a certain image is photographed at a certain date and place. Furthermore, in the case of FIG. 18, the display on the map makes it possible to intuitively recognize the relationship between the position where the photographing that is the reinforcement target behavior is performed and the change in the avatars.

Moreover, in a case where the plurality of avatars 411 exists in the same place, the plurality of avatars can be displayed in time series in the same place. By doing in this way, the change in the avatars 411 is capable of being recognized at the same place and in time series.

<First Display Example of Predictive Image>

A first display example of a predictive image is now described with reference to FIG. 19.

Figure 19:
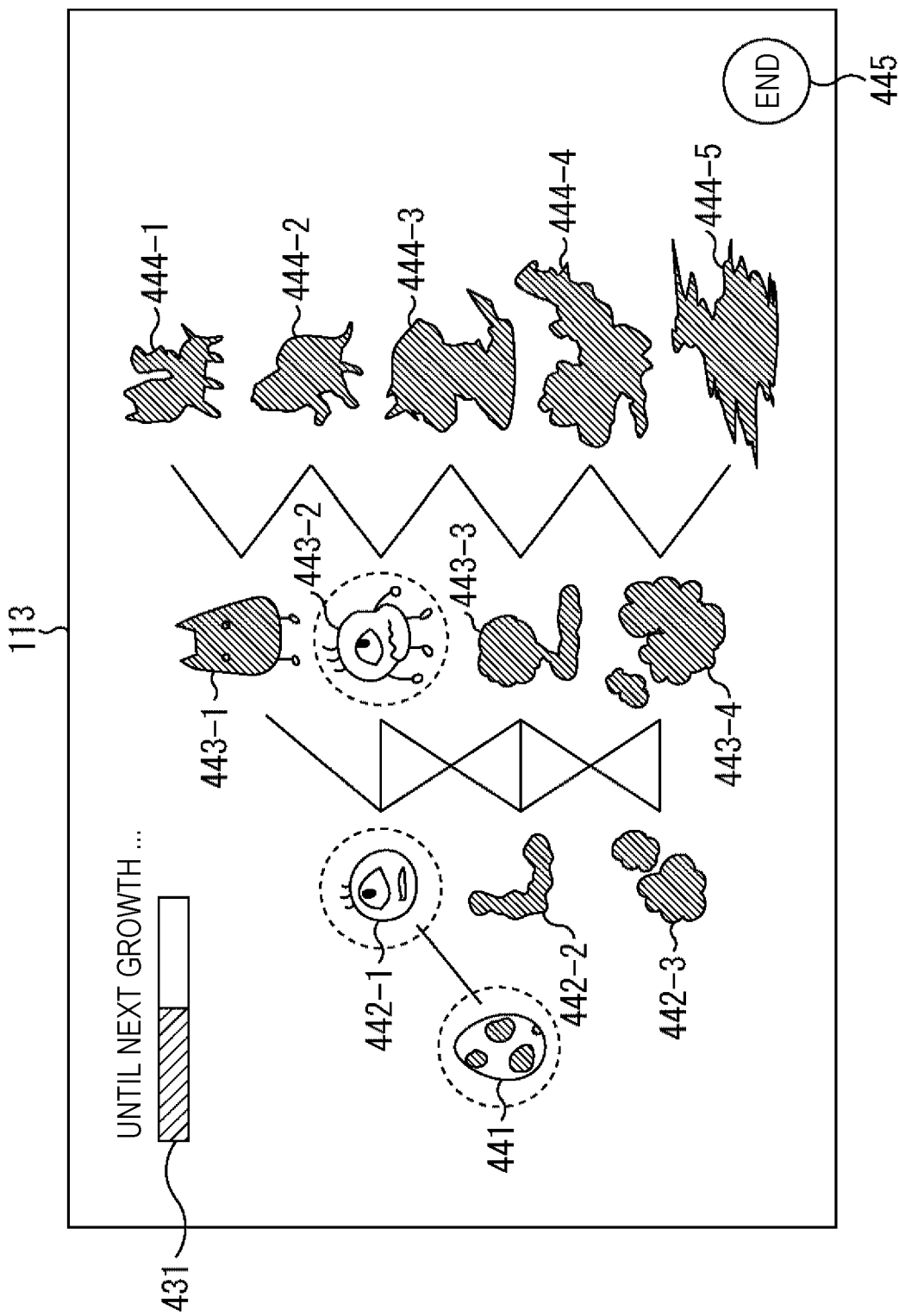
FIG. 19 is a diagram illustrated to describe a display example of a predictive image.

In the case where the predictive-image display button 356 of FIG. 15 is operated, in one example, a predictive image as illustrated in FIG. 19 is displayed.

The predictive image in FIG. 19 is an image in which the change in avatars is expressed in the form of a dendrogram as described with reference to FIG. 11. In other words, egg (root), larva, sub-adult, and adult are displayed in this order from the left in the figure.

More specifically, an avatar 441 on the leftmost in the figure represents an egg (root) and indicates the starting point of the change in avatars.

In addition, avatars 442-1 to 442-3 as a larva are displayed on the right side thereof.

Furthermore, avatars 443-1 to 443-4 as a sub-adult are displayed on the further right side thereof.

In addition, avatars 444-1 to 444-5 as an adult are displayed on the even further right side thereof.

The end button 445 is provided at the lower right of the predictive image in FIG. 19. The end button 445 is operated when the display of the predictive image terminates and returns to the display image of the presentation that urges the reinforcement target behavior depending on the long-term change table of FIG. 15.

In this example, among the avatars 441, 442-1 to 442-3, 443-1 to 443-4, and 444-1 to 444-5, the avatars that have changed so far are displayed as the state to be visually recognized while being marked with a dotted circle, but other avatars are displayed as silhouettes.

Further, in the upper left part of the figure, an indicator 431 is shown, and an indication until the next change in avatars is shown. In other words, in the number of times counted as the dominant emotion for each emotion in the long-term change table, the proportion of the current number of times to the number of times that is the threshold value until the avatar having the highest value changes is displayed on the indicator 431 as an indication until the next change in the avatars.

The display as described above makes it possible for the user to check that the current state of the change in avatars corresponds to which position in the dendrogram. Thus, it is possible to predict an avatar to be changed to some extent by performing what kind of reinforcement target behavior in the future.

<Second Display Example of Predictive Image>

A second display example of a predictive image is now described with reference to FIG. 20.

Figure 20:
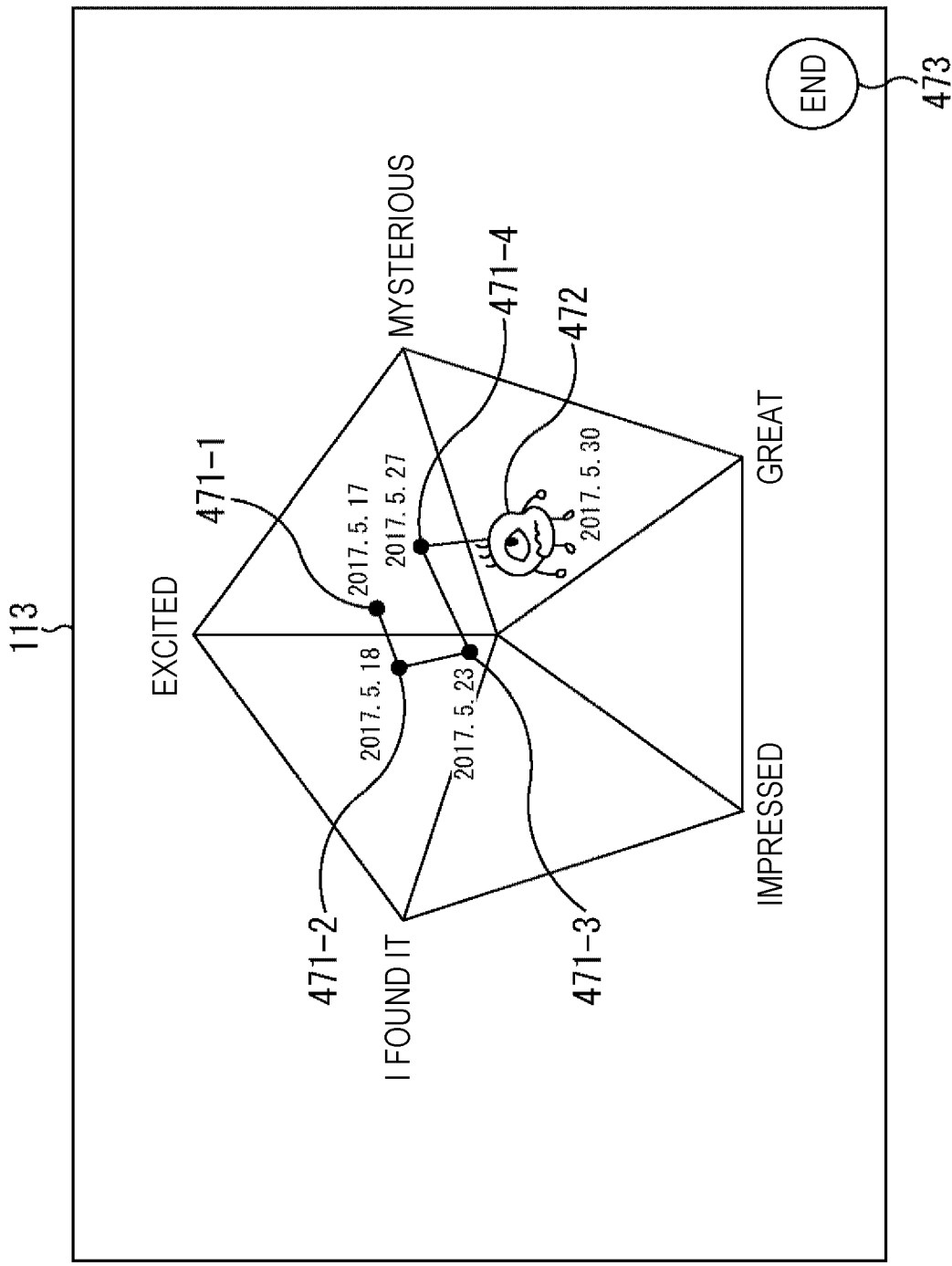
FIG. 20 is a diagram illustrated to describe a display example of a predictive image.

The predictive image as shown in FIG. 20 may be displayed, in one example, when the predictive-image display button 356 in FIG. 15 is operated.

The predictive image in FIG. 20 shows a change on a radar chart for each emotion of the emotion estimation result.

In other words, a case is considered where the emotion estimation results are, in one example, a set of five types of emotions of "excited", "mysterious", "impressed", "I found it", and "great". FIG. 20 is an image obtained by plotting the center of gravity of a figure formed when connecting points when expressed by a radar chart on the basis of the scores of five types of emotions as emotion estimation results. The date is added to each plot and the plots are chronologically connected by lines.

In other words, FIG. 20 shows that the center of gravity 471-1 indicates the center of gravity of the figure on the radar chart formed by the scores of five types of emotions when the photographing that is the reinforcement specifying behavior on May 17, 2017, is performed.

In addition, FIG. 20 shows that the center of gravity 471-2 indicates the center of gravity of the figure on the radar chart formed by the scores of five types of emotions when the photographing that is the reinforcement specifying behavior on May 18, 2017, is performed.

Further, FIG. 20 shows that the center of gravity 471-3 indicates the center of gravity of the figure on the radar chart formed by the scores of five types of emotions when the photographing that is the reinforcement specifying behavior on May 23, 2017, is performed.

In other words, FIG. 20 shows that the center of gravity 471-4 indicates the center of gravity of the figure on the radar chart formed by the scores of five types of emotions when the photographing that is the reinforcement specifying behavior on May 27, 2017, is performed.

Furthermore, an avatar 472 indicates the current avatar shown in the center of gravity of the figure on the radar chart formed by the scores of five types of emotions when the photographing that is the reinforcement specifying behavior on May 30, 2017, is performed.

Further, the end button 473 is provided at the lower right of the predictive image in FIG. 20. The end button 473 is operated when the display of the predictive image terminates and returns to the display image of the presentation that urges the reinforcement target behavior depending on the long-term change table of FIG. 15.

The display as described above makes it possible for the user to recognize the change in avatars up to the current state, so the emotion estimation result and the change in avatars can be visually recognized. Thus, it is possible to predict an avatar to be changed by repeating the reinforcement target behavior to some extent.

Moreover, although the example which shows the change in avatars is described in FIGS. 19 and 20, not only the change in avatars, in one example, but also the change for each part of the avatar can be indicated.

<Reinforcement Target Behavior Reinforcing Processing>

Figure 21:
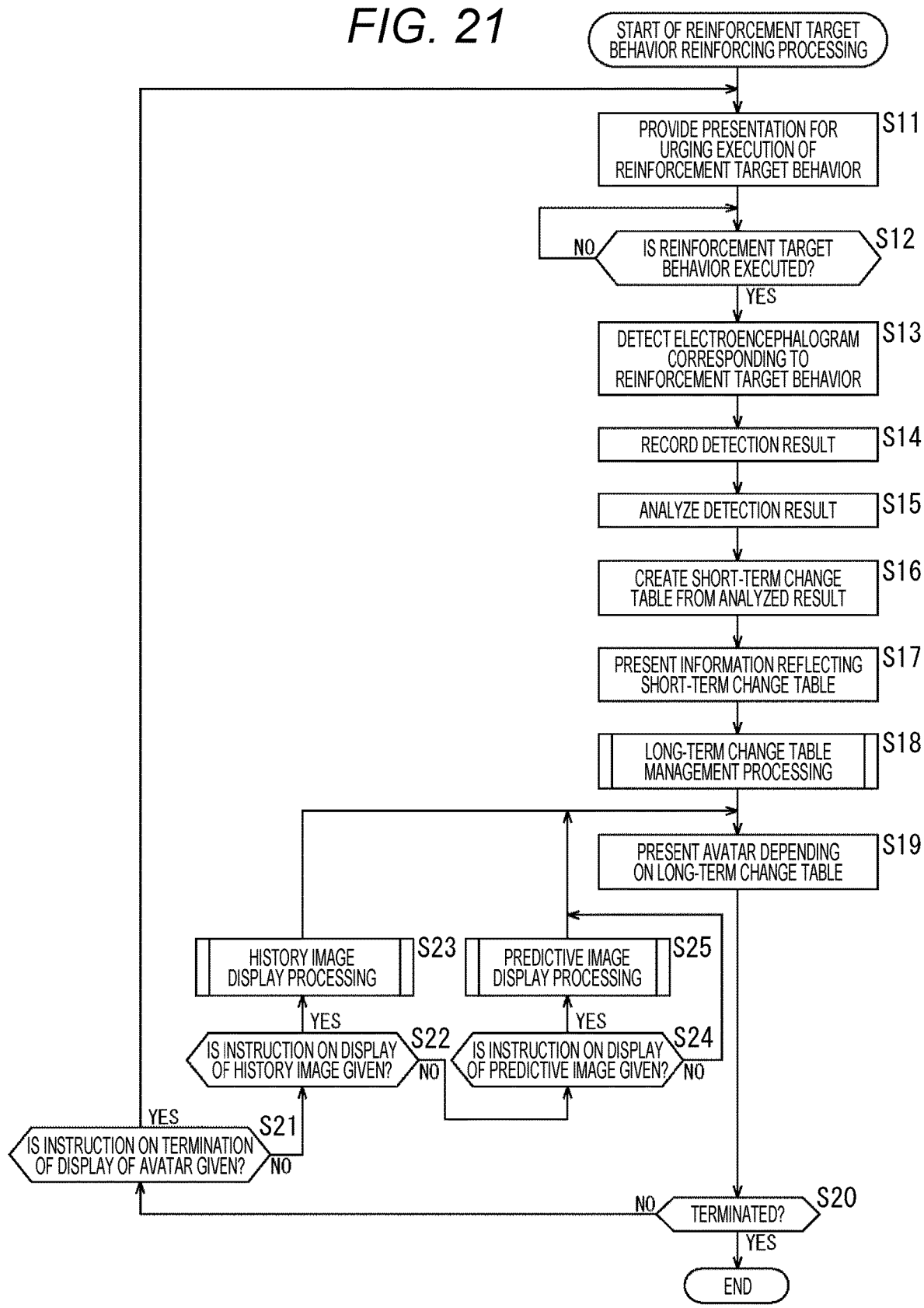
FIG. 21 is a flowchart illustrated to describe reinforcement target behavior reinforcing processing.

With reference to the flowchart of FIG. 21, reinforcement target behavior reinforcing processing performed by the information processing system of FIG. 3 is now described.

In step S11, the image processing unit 95 generates an image that presents a quest for urging the execution of the reinforcement target behavior described with reference to FIG. 4, controls the communication unit 92 so that the communication unit 92 outputs the image to the display apparatus 42. The display apparatus 42 controls the communication unit 114 so that the communication unit 114 receives the image and the display apparatus 42 causes the display unit 113 to display it.

This processing causes, in one example, a quest of "take a nature photo" to be displayed in the quest display portion 207 as described with reference to FIG. 4, causes a preview image in the current photographing direction to be displayed, and causes the photographing as the reinforcement target behavior to be urged for the user depending on the quest.

In step S12, the information processing apparatus 41 determines whether, in one example, the shooting button 204 on the display unit 113 of the display apparatus 42 shown in FIG. 4 is operated and the photographing as the reinforcement target behavior is performed or not via the communication unit 92. In step S12, the information processing apparatus 41 repeats the similar processing until the photographing is considered to be performed.

In step S12, in a case where the user selects the composition for the photographing, the shooting button 204 is operated, the photographing as the reinforcement target behavior is performed, the processing proceeds to step S13.

In step S13, the information processing unit 93 controls the imaging unit 94 upon the operation of the shooting button 204 so that the imaging unit 94 captures an image, controls the image processing unit 95 so that the image processing unit 95 performs predetermined image processing on it, and then cause data of the image to be stored in the storage unit 96.

Furthermore, the information processing unit 93 controls the communication unit 92 to acquire the electroencephalogram detection result and the biometric information supplied from the electroencephalograph 31 and the biometric sensor 32, respectively and records them. In particular, the information processing unit 93 causes the storage unit 96 to store them in association with Exif in an image captured by photographing as the reinforcement target behavior.

Moreover, in the typical processing procedure, if the reinforcement target behavior is urged by the processing of step S11 and the execution of the reinforcement target behavior is detected by the processing of step S12, the processing of step S13 and subsequent processing are performed. However, in the present embodiment, the reinforcement target behavior is specifically photographing, so the processing of step S13 records an image is performed as processing accompanying the execution of the reinforcement target behavior. In addition, there is a various pieces of reinforcement target behavior depending on the quest. In one example, in the case of a quest in which the user is caused to take five photographs and the user selects one of them, in step S12, if the behavior of selecting one of the five photographs is performed, the reinforcement target behavior can be considered to be performed. However, in this case, the emotion estimation necessitates the use of use the electroencephalogram or biometric information at the timing when one selected photograph is taken for the emotion estimation.

In step S14, the information processing unit 93 controls the communication unit 92 so that the communication unit 92 transmits the electroencephalogram detection result and the biometric information to the server 43.

In step S15, the emotion estimation unit 131 of the server 43 estimates the emotion on the basis of the electroencephalogram detection result and the biometric information and transmits the emotion estimation result to the information processing apparatus 41. The information processing unit 93 of the information processing apparatus 41 controls the communication unit 92 so that the communication unit 92 receives the emotion estimation result transmitted from the server 43.

In step S16, the information processing unit 93 creates a short-term change table on the basis of the emotion estimation result. In this description, the short-term change table to be created is, in one example, the short-term change table as illustrated in FIG. 12. In this event, the information processing unit 93 causes the storage unit 96 to store the emotion estimation result in association with Exif in an image captured by the photographing as the reinforcement target behavior. Moreover, although the description is given of the example in which Exif is stored in association with an image, Exif is not necessarily stored in association with an image, in one example, it can be recorded independently of an image.

In step S17, the information processing unit 93 controls the image processing unit 95 so that the image processing unit 95 generates a display image that reflects the information regarding the short-term change table, and causes the generated display image to be displayed on the display unit 113 of the display apparatus 42. More specifically, the information processing unit 93 causes the display contents of the dominant emotion display portion 203 illustrated in FIG. 4 to be switched into the information regarding the dominant emotion that is the emotion having the highest score in the short-term change table.

In other words, the avatar does not change even when the photographing is performed in an apathetic state, so the user attempts to find a situation in which the emotion is likely to be changed to change the avatar. In this event, the dominant emotion is presented immediately after the photographing, so it is possible to immediately recognize which type of emotion is exerting the greatest effect. Thus, the user is able to try to restrain apathetic photographing, resulting in reinforcing the reinforcement target behavior.

Moreover, although the above description is given of, as an example of a display image that reflects the information regarding the short-term change table, the example in which the display contents of the dominant emotion display portion 203 is switched into the information regarding the dominant emotion that is the emotion with the highest score in the short-term change table and displayed, the information regarding the short-term change table can be recognized by the user employing other ways. In one example, depending on the emotion estimation result, the presentation can be achieved by changing the color, by giving a voice, by changing the size or shape of display contents, or by changing the avatar's motion. In other words, various aspects can be achieved as long as the electroencephalogram measurement and the emotion estimation results in one time of the photographing are fed back to the user.

In step S18, the information processing unit 93 executes long-term change table management processing and reflects the information regarding the short-term change table for its updating. The long-term change table management processing will be described in detail later with reference to the flowchart of FIG. 22.

In step S19, the information processing unit 93 controls the image processing unit 95 so that the image processing unit 95 generates a display image that presents the avatar, in one example, described with reference to FIG. 15 on the basis of the long-term change table and causes the generated display image to be displayed on the display unit 113 of the display apparatus 42.

In other words, the image described with reference to FIG. 15 allows the user to check the current avatar changed by repeating the photographing that is the reinforcement target behavior depending on the previous quest.

In step S20, the information processing unit 93 determines whether or not the display unit 113 that functions as a touch panel is operated and an instruction for terminating the reinforcement target behavior reinforcing processing is given. If the instruction of the termination thereof is given, the processing ends. While, in step S20, if the instruction of the termination thereof is not given, the processing proceeds to step S21.

Moreover, in determining the termination of the reinforcement target behavior reinforcing processing, any one of a case where the instruction of the termination of the processing is directly given, a case where a predetermined time has elapsed (time limit method), or a case where the number of times of photographing reaches a predetermined number of times (number-of-times limit method) can be considered as the instruction of the termination of the processing.

Further, the instruction of the termination can be set depending on the contents of the quest or, in one example, in the case where the time is limited by the quest, the timing at which the time set in the quest has elapsed may be considered as the instruction of the termination.

Furthermore, the instruction of the termination can be considered to be given in a case where a particular composition or attitude is detected. Alternatively, the instruction of the termination can be considered to be given in a case of detecting that the camera is closed, a case of turning off the power, a case of reading a predetermined QR code (registered trademark), or a case where a particular subject is photographed or detected in the viewfinder.

Further, the instruction of the termination can be considered to be given at the timing when the change in the avatars reaches a predetermined state.

In step S21, the information processing unit 93 determines whether or not, in one example, the end button 357 on the display image illustrated in FIG. 15 is operated and an instruction for displaying the image in FIG. 4 presenting a quest that gives an instruction for the image photographing as the next reinforcement target behavior is given. In step S21, in one example, in the case where the end button 357 is determined not to be operated, the processing proceeds to step S22.

In step S22, the information processing unit 93 determines whether or not, in one example, the history image display button 355 on the display image illustrated in FIG. 15 is operated and an instruction for displaying the history image of the avatar is given. If it is determined in step S22 that the history image display button 355 is operated, the processing proceeds to step S23.

In step S23, the information processing unit 93 executes the history image display processing, generates the history image, in one example, described with reference to FIG. 17 or 18, causes it to be displayed on the display unit 113 of the display apparatus 42, and then the processing returns to step S19. Moreover, the history image display processing will be described in detail later with reference to the flowchart of FIG. 23.

On the other hand, if it is determined in step S22 that the history image display button 355 is not operated, the processing proceeds to step S24.

In step S24, the information processing unit 93 determines whether or not, in one example, the predictive-image display button 356 on the display image illustrated in FIG. 15 is operated and an instruction for displaying the predictive image of the avatar is given. If it is determined in step S24 that the predictive-image display button 356 is operated, the processing proceeds to step S25.

In step S25, the information processing unit 93 executes the predictive image display processing, generates the history image, in one example, described with reference to FIG. 19 or 20, causes it to be displayed on the display unit 113 of the display apparatus 42, and then the processing returns to step S19. Moreover, the predictive image display processing will be described in detail later with reference to the flowchart of FIG. 24.

On the other hand, if it is determined in step S21 that the end button 357 is operated, the processing returns to step S11 and the subsequent processing is repeated.

Moreover, in step S24, if the instruction for displaying the predictive image is not given, the processing in step S25 is skipped and the processing returns to step S19.

In other words, in a case of displaying a quest, of urging the user to perform the photographing that is the reinforcement target behavior, and of performing the photographing that is the reinforcement target behavior by the user, the electroencephalogram at that timing is detected and the corresponding biometric information is detected. Then, the emotion estimation is performed on the basis of the electroencephalogram detection result and the biometric information, and a short-term change table is created. The long-term change table is updated depending on the short-term change table, the avatar changes on the basis of the information regarding the long-term change table and then is presented.

For this reason, the avatar changes every time the user repeatedly performs the reinforcement target behavior depending on the quest, so the consciousness of wanting to change the avatar is stimulated. As a result, it is possible to reinforce the reinforcement target behavior without making the user aware of the reinforcement target behavior.

Moreover, although the above description is given of the example in which the reinforcement target behavior reinforcing processing is started at the timing where the reinforcement target behavior is executed, it can be started at any other timings. Examples of the start thereof can include the start by the user, the start at a timing when the system detects a change in emotion, and the time limit method using the timing at which a predetermined time elapses from a predetermined timing.

Further, in a case where the avatar is likely to change, a display that allows a sign of the change to be recognized can be performed. The display such as "It will change upon taking subsequent n photos" or "It will change upon being impressed n subsequent times" is performed depending on the quest. Alternatively, the avatar can be displayed so that an aura appears. Such a display makes it possible to achieve a mechanism that urges the user to continue use, gives the user motivation, and does not make the user more bored.

<Long-Term Change Table Management Processing>

Figure 22:
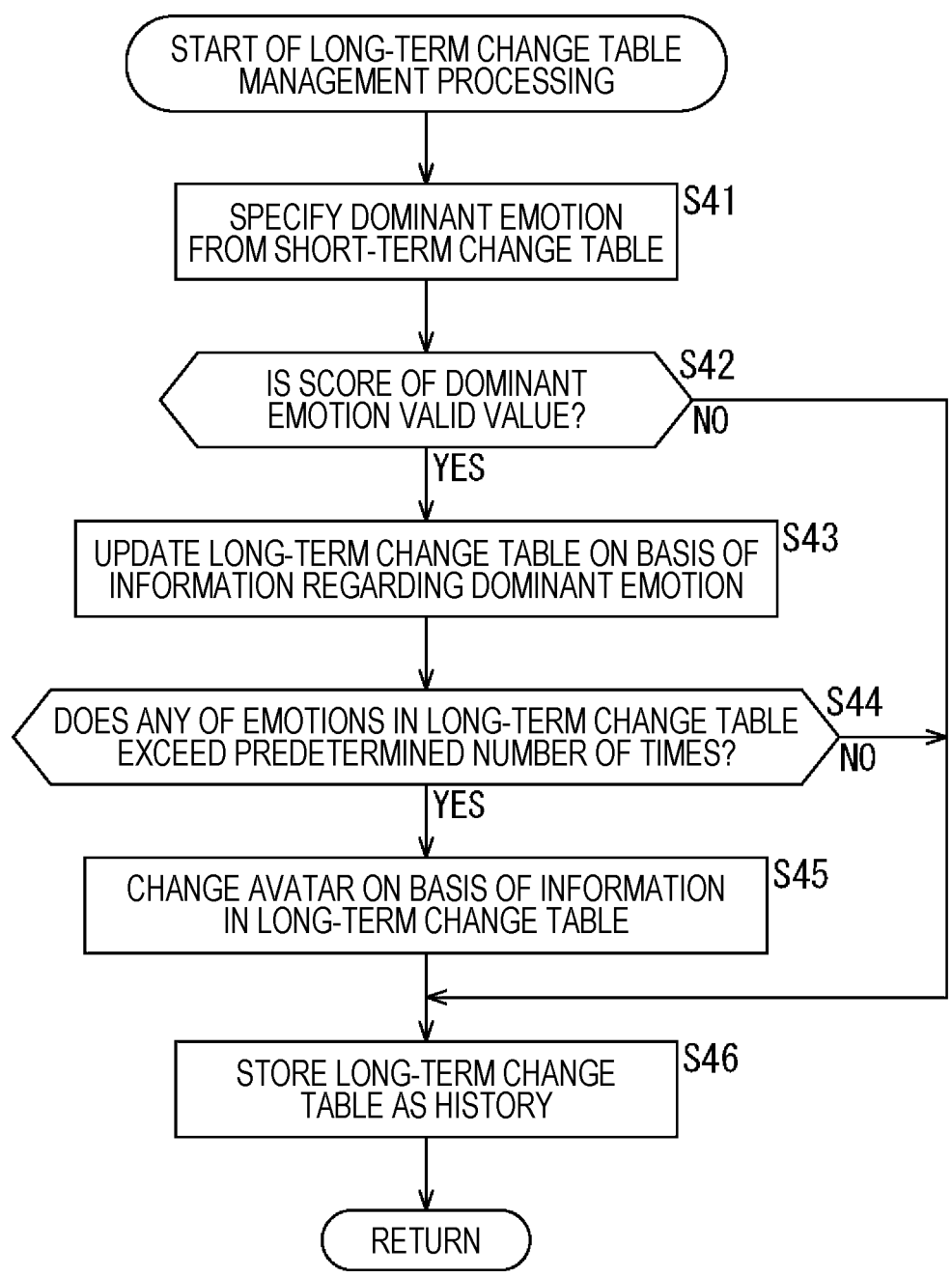
FIG. 22 is a flowchart illustrated to describe processing of managing a long-term change table.

The long-term change table management processing is now described with reference to the flowchart of FIG. 22.

In step S41, the information processing unit 93 determines the dominant emotion on the basis of the information regarding the short-term change table. In other words, in the case of the short-term change table as illustrated in FIG. 12, the scores of the emotions m1, m2, and m3 are 10, 60, and 30, respectively, so the information processing unit 93 determines the dominant emotion as the emotion m2.

In step S42, the information processing unit 93 determines whether or not the score that is the result of detecting the dominant emotion is a valid value. In other words, it is determined whether or not the highest score among the emotion scores of the emotion set included in the emotion estimation result is a valid value larger than a predetermined value. In one example, in a case where a score threshold for each emotion is 50, the score 60 of the emotion m2 that is the dominant emotion is larger than the threshold in the short-term change table of FIG. 12. Thus, in this case, in step S42, the score is regarded as a valid value, and the processing proceeds to step S43.

In step S43, the information processing unit 93 reflects the detection result of the dominant emotion in the long-term change table. In other words, as described with reference to FIG. 13, the information processing unit 93 counts up the number of times in the number-of-times column of emotions detected as the dominant emotion by incrementing it by one.

In step S44, the information processing unit 93 determines whether or not the number of times detected as the dominant emotion among the types of emotions managed as the long-term change table exceeds a predetermined number of times. If it is determined in step S44 that, the number of times detected as the dominant emotion among the types of emotions managed as the long-term change table exceeds a predetermined number of times that is a threshold, the processing proceeds to step S45.

In step S45, as described with reference to FIG. 11, the information processing unit 93 updates the information in the avatar type column of the long-term change table (to change the characteristics of the avatar) and resets the number-of-times column so that the current avatar changes to an avatar corresponding to the type of emotion in which the number of times detected as the dominant emotion exceeds the predetermined number.

In step S46, the information processing unit 93 stores the information of the current long-term change table in the storage unit 96 as a history in association with an image captured by photographing that is the reinforcement target behavior.

Moreover, if it is determined in step S42 that the score of the dominant emotion is not a valid value, the processing in steps S43 to S45 is skipped, the long-term change table is not substantially updated, and the processing proceeds to step S46.

In step S44, if there is no emotion in which the number of times of the number-of-times column in the long-term change table exceeds the predetermined number of times, the processing of step S45 is skipped. In other words, in this case, the number-of-times column of the emotion detected as the dominant emotion is updated, but the avatar does not change, and the processing proceeds to step S46.

The above processing allows, every time the emotion estimation result corresponding to the reinforcement specifying behavior repeated by the quest is supplied, the short-term change table to be supplied and the dominant emotion to be detected on the basis of the short-term change table and allows the number of times detected as the dominant emotion to be counted and, if the detected number of times exceeding the predetermined number of times is detected, the avatar to be changed in the case where the score is the valid value.

This allows the long-term change table to be repeatedly updated in the long term on the basis of the emotion estimation result corresponding to the reinforcement specifying behavior repeated by the presentation of the quest and the avatar to be changed depending on the update result. Thus, it is possible for the avatar to be changed by the reinforcement specifying behavior, resulting in stimulating the consciousness of wanting to change the avatar. Consequently, the consciousness of the desire to change the avatar makes it possible to reinforce the reinforcement target behavior without causing the user's consciousness.

Moreover, although the above description is given of the example in which the number of times of specification of the dominant emotion is stored in the long-term change table and the avatar is changed in association with the emotion exceeding the predetermined number of times as the dominant emotion stored in the long-term change table, it is also possible to integrate the scores for all emotions and change the avatar in association with the emotions having integrated value of the score exceeding the predetermined value. In addition, in a case where any emotion in the emotion estimation result is specified under some condition and the specified number of times exceeds a predetermined number, it is sufficient for the avatar to change depending on the emotion exceeding the predetermined number, so emotions other than the dominant emotion can be used. In one example, the avatar can be changed depending on whether or not the number of times of specification of an emotion continuously exceeding a predetermined score exceeds a predetermined number.

Furthermore, the avatar can be changed to an avatar corresponding to the dominant emotion that is recorded most frequently within a predetermined number of times of measurement. In addition, the avatar can be changed by integrating the elemental emotions in each measurement rather than the dominant emotion and by selecting the emotion having the highest integrated value when the predetermined number of measurements is reached. Furthermore, the next change of the avatar can be determined by the balance of emotions rather than one emotion.

In addition, the avatar can be changed on the basis of not only on the number of times of measurement, but also the frequency, of the dominant emotion, the intervals, the emotion strength (reliability of the analysis result), the contents of the quest, and whether or not it is moved a certain distance.

In addition, in a case where a particular emotion, such as a first emotion or a rare emotion, is detected, the detection of the particular emotion can be regarded as text display, reflection on the quest, change in avatars, change of avatar aura or facial expression to provide feedback.

Furthermore, a predetermined filter can be applied to the long-term change table. In one example, in integrating the scores of emotions, it is possible to generate an avatar having a personality opposite to the user's personality by multiplying the reciprocal number or using a filter that integrates the score of the emotion that is contrary to the detected emotion. Alternatively, it is possible to cancel or reinforce the measurement bias generated for each quest by preparing a filter that multiplies a coefficient that cancels the measurement bias assumed for each quest or reinforces it.

Furthermore, for the long-term change table, in one example, a male of blood type O and a female of blood type A can be combined with a filter having good compatibility such as good affinity.

In addition, for the emotion estimation result stored in the long-term change table, the bias value can be calculated using other emotions than the particular emotion. In one example, the set of five emotions of "excited", "mysterious", "impressed", "I found it" and "great" is exemplified, but, in addition to the five-emotion set, in a case where emotions of "uninterested" and "boring" are estimated and the emotions of "uninterested" and "boring" are obtained, the integration of the dominant emotions can be subtracted, so it is possible to change the influence of the accumulation on the photographing of the subject of interest or eliminate the influence without performing the integration. In addition, the long-term change table is not recalculated for each reinforcement target behavior, but it is possible to use the average, median, or representative value, or the like of emotion estimation results, or a time interval from the last detection, a difference in positions of the user, or the like, for a plurality pieces of reinforcement target behavior, and in this case, the recalculated timing can be synchronized with the quest.

Further, the avatar may not be necessarily displayed as an image and, in one example, can be hardware such as a robot. In addition, a category of avatars can be selected or it can be set or changed appropriately. Furthermore, in one example, it can be changed depending on the user's preference. In addition, in one example, it can be changed depending on the preference by performing the image analysis of a photographic subject and reflecting the result. Furthermore, the type of avatar corresponding to the reinforcement target behavior can be set, and in one example, in the case of a learning system, a student avatar can be set.

Further, the avatar can be an imitation of a creature such as a character plant or can be an inorganic material such as a castle, town, or vehicle.

Moreover, the avatar can be displayed not only as an image but also as a text format, voice, vibration, smell, sense of touch, sense of taste, and feedback from the motion of a robot or the like (e.g., in the case of a dog-shaped robot, how to dance, how to swing a tail, facial expression, etc.) to represent the characteristics of the avatar.

Furthermore, the avatar can reflect the user's personality, or it can be the opposite of personality by multiplying the score stored in the long-term change table, the number of times of specification of the dominant emotion, or the like by the reciprocal, or alternatively, it can be the personality having good compatibility.

In addition, the avatar can change its form or appearance, it can follow the route depending on the emotion estimation result among its changes in the predetermined dendrogram as illustrated in FIG. 11, or it includes a plurality of parts (hands, feet, eyes, mouth, etc.) constitutes the body and these parts can change individually depending on the emotion estimation results.

Furthermore, the avatar can change its adornments such as weapons, items, clothes, ornaments, or the like.

In addition, the avatar can have a profile so that various setting values such as the character's strength, defense power, and speed can be changed and then compared with others and ranked.

Furthermore, a new avatar can be presented or acquired for each emotion estimation result instead of changing one fixed avatar. In this event, the long-term feedback using the long-term change table is performed, so it is also possible to present the overall tendency such as arranging the avatars of frequent types arranged in time series.

The long-term change table can reflect, in the case where n types of emotions are defined, the dominant emotion, or can reflect it depending on the proportion, or alternatively reflect them as the absolute value.

Although the above description is given of the example in which the avatar changes when the number of times of specification of the dominant emotion exceeds the predetermined number, in one example, in the case where the score based on the reinforcement target behavior is accumulated, the timing at which the score is reflected in the avatar can be made selectable by the user. Specifically, in a case where the reinforcement target behavior is performed five times, instead of reflecting the score on the avatar each time, the accumulated scores or the amounts thereof are presented to the user and the user performs an operation of reflecting all or part of the accumulated scores in the avatar at the timing preferred by the user. This makes it possible for the user to concentrate on the reinforcement target behavior upon performing the reinforcement target behavior and to enjoy in other timings at which the score is reflected in the avatar and the accompanying it.

In addition, additional changes such as ornaments attached to the avatar can be selectively controlled by the user. In other words, a change in the avatar body that is incapable of being controlled by the user and a change in ornaments capable of being controlled by the user can be mixed.

In this event, in one example, the characteristics depending on the emotion estimation result can be given to the ornaments exchangeable with another player. In this event, the change based on the reinforcement target behavior can be taken into account. In one example, it can reflect color, texture, or the like of the taken photograph on the avatar or background, or alternatively it can reflect the position information and the camera settings at the time of the photographing.

In addition, the period during which the state change of the avatar occurs can be limited. In one example, it is possible to reset the next avatar depending on the change of the user's actual school grade, and such limitation can be applied to the place or space (field) or the limitation can be applied to the quest period or the like.

Furthermore, a plurality of avatars can be prepared so that different avatars are presented depending on environments. In addition, the avatar used as reflection target can be changed for every communication group. Furthermore, the avatar can be changed depending on the estimation result of the user's state (what kind of state or who with you). Alternatively, depending on the social graph analysis result, position, biometric sensing, surrounding environment (what is shown in the photograph), time zone, and place of the conversation opponent, the corresponding avatar can be changed.

In addition, a plurality of avatars used as the reflection target can be set and used separately. The avatar can be generated for each event. The reflection can be applied to a fixed target for each TPO every time.

Thus, the avatar's personality reflects the user as the reinforcement target behavior is performed, so it is possible to provide an incentive for the user to perform the reinforcement target behavior. In addition, with the change in appearance of the avatar, it is possible to provide an incentive for the user who desires to continue the reinforcement target behavior and to continue the electroencephalogram measurement.

Consequently, it is possible to reinforce the reinforcement target behavior without causing the user's consciousness. In addition, the reinforcement of the reinforcement target behavior makes it possible to continuously acquire useful electroencephalogram data.

<History Image Display Processing>

Figure 23:
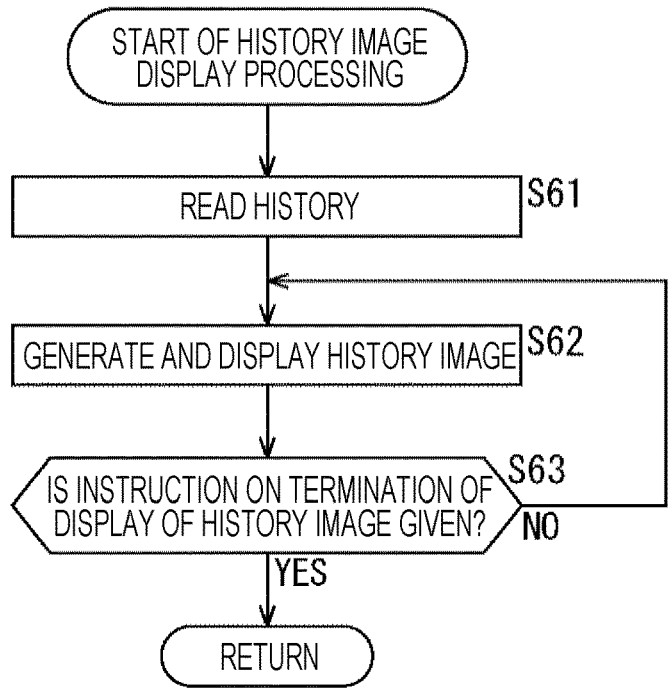
FIG. 23 is a flowchart illustrated to describe processing of displaying a history image.

With reference to the flowchart of FIG. 23, history image display processing is now described.

In step S61, the information processing unit 93 reads out to the storage unit 96, as historical information, an image captured by the photographing that is the reinforcement target behavior, information regarding the long-term change table stored in association with the image, and information of Emotion_information included in the Exif format.

In step S62, the information processing unit 93 generates, in one example, a history image, as illustrated in FIGS. 17 and 18, on the basis of the read history information and causes it to be displayed on the display unit 113 of the display apparatus 42.

In step S63, the information processing unit 93 determines whether or not, in one example, the end button 375 shown in FIG. 17 or the end button 402 shown in FIG. 18 is operated on the display unit 113 that functions as a touch panel and an instruction for terminating the history display is given. If the instruction of the termination is not given in step S63, the processing returns to step S62, the processing of steps S62 and S63 is repeated, and the history image continues to be displayed. On the other hand, if it is determined in step S63 that the instruction of the termination is given, the processing ends.

The processing in the steps mentioned above allows the history image as illustrated in FIG. 17 or 18 to be displayed, so the user is able to recognize how the avatar is changed in the photographing that is the past reinforcement specifying behavior, and further, it is also possible to stimulate the desire to change the avatar.

Consequently, it is possible to achieve reinforcement of the reinforcement target behavior without causing the user's consciousness.

<Predictive Image Display Processing>

Figure 24:
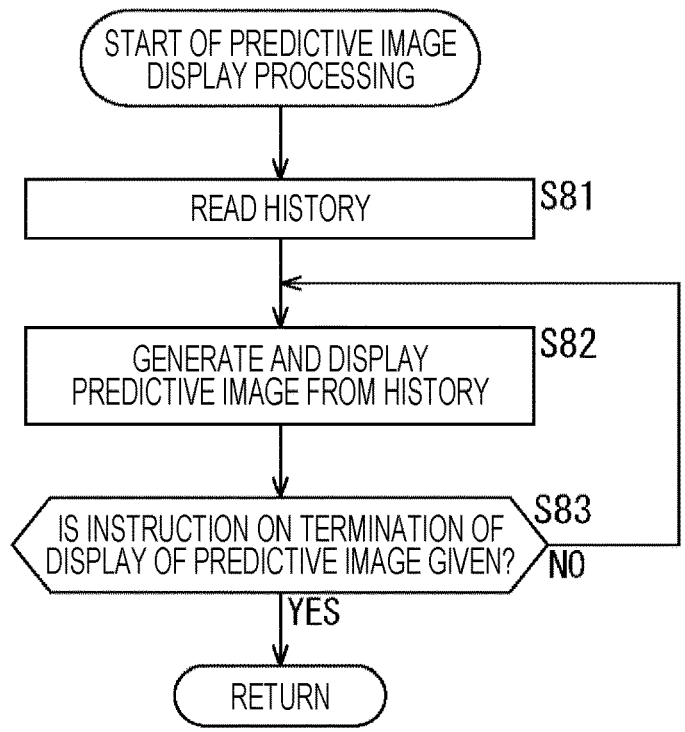
FIG. 24 is a flowchart illustrated to describe processing of displaying a predictive image.

With reference to the flowchart of FIG. 24, predictive image display processing is now described.

In step S81, the information processing unit 93 reads out to the storage unit 96, as historical information, an image captured by the photographing that is the reinforcement target behavior, information regarding the long-term change table stored in association with the image, and information of Emotion_information included in the Exif format.

In step S82, the information processing unit 93 generates, in one example, a history image, as illustrated in FIGS. 19 and 20, on the basis of the read history information and causes it to be displayed on the display unit 113 of the display apparatus 42.

In step S83, the information processing unit 93 determines whether or not, in one example, the end button 445 shown in FIG. 19 or the end button 473 shown in FIG. 20 is operated on the display unit 113 that functions as a touch panel and an instruction for terminating the history image display is given. If the instruction of the termination is not given in step S83, the processing returns to step S82, the processing of steps S82 and S83 is repeated, and the predictive image continues to be displayed. On the other hand, if it is determined in step S83 that the instruction of the termination is given, the processing ends.

Moreover, the termination of the history image display or the termination of the predictive image display can be performed not only by pressing the end button 375 or 445, respectively, but also by other triggers. Alternatively, it can be considered that the termination instruction is given when the user has come to a place where a good photograph is taken or when the emotion changes.

The processing in the steps mentioned above allows the predictive image as illustrated in FIG. 19 or 20 to be displayed, so the user is able to recognize how the avatar is changed in the photographing that is the past reinforcement specifying behavior, future change of the avatar can be predicted, and further, it is also possible to stimulate the desire to change the avatar.

Consequently, it is possible to achieve reinforcement of the reinforcement target behavior without causing the user's consciousness.

<<3. First Modification>>

<Example of Storing Electroencephalogram Detection Result and Biometric Information Obtained by Performing Reinforcement Target Behavior Plurality Number of Times for Image of Photographing as Identical Reinforcement Target Behavior> the above description is given of the example in which one piece of Emotion_information used to store electroencephalogram detection results and biometric information is provided for one image captured by single photographing that is the reinforcement target behavior. However, the electroencephalogram detection result and biometric information obtained by performing the reinforcement target behavior a plurality of number of times can be stored for an image of the photographing as the same reinforcement target behavior.

Figure 25:
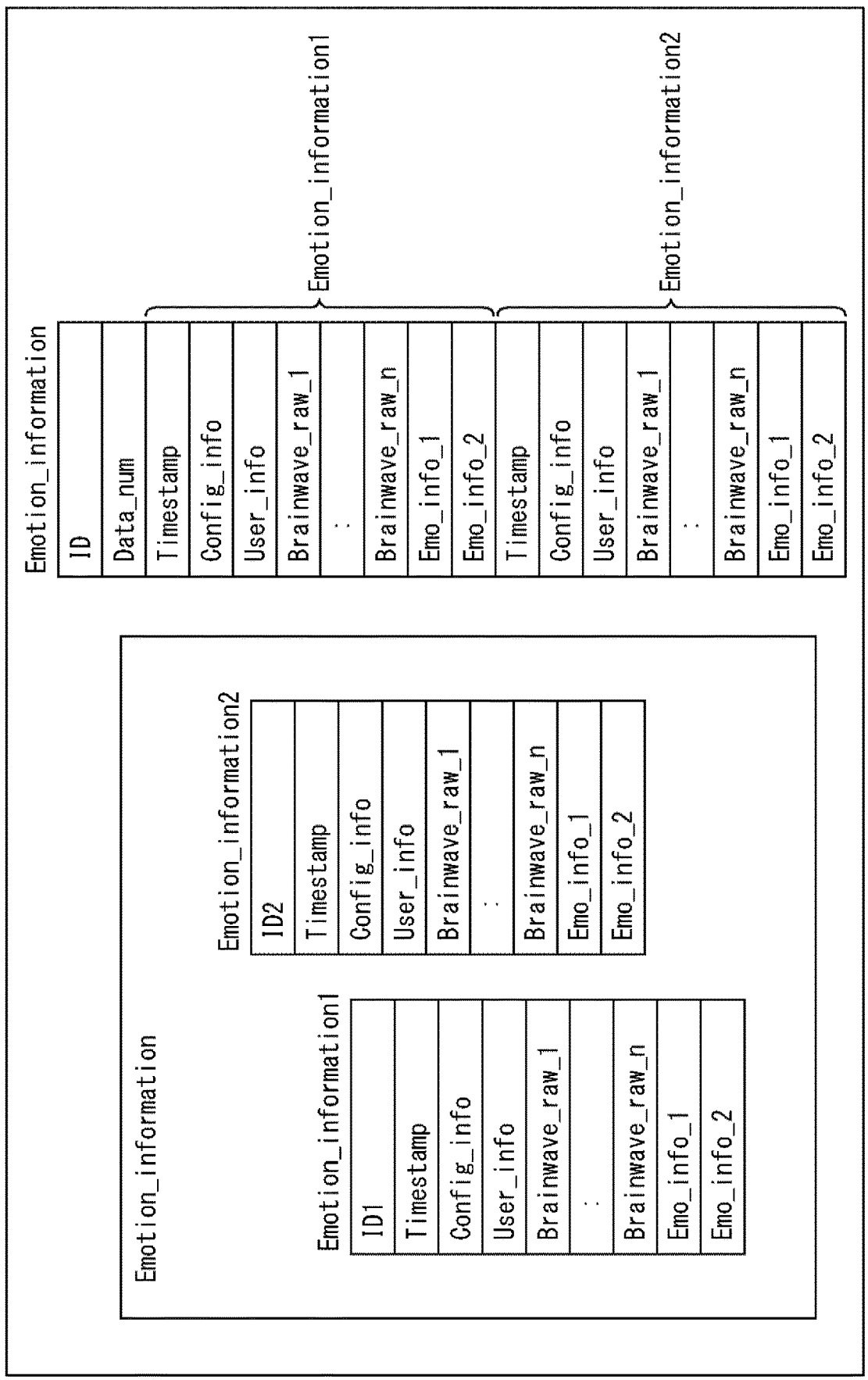
FIG. 25 is a diagram illustrated to describe a first modification.

In one example, as shown in the left part of FIG. 25, Emotion_information can include a plurality of files, that is, Emotion_information1 and Emotion_information2.

In addition, as shown in the right part of FIG. 25, a plurality of pieces of information of Emotion_information1 and Emotion_information2 can be stored in one piece of Emotion_information. However, in the case of the right part of FIG. 25, Data_num stores the number of a plurality of stored electroencephalogram detection results and biometric information. In addition, Emotion_information1 and Emotion_information2 have their respective IDs omitted.

In any case, on the basis of a plurality of electroencephalogram detection results and biometric information, it is possible to detect the electroencephalogram or perform the emotion estimation at a timing different from the timing at which the reinforcement target behavior is performed.

<<4. Second Modification>>
<Example of Storing Reference Electroencephalogram Detection Information Measured Upon Calibration and Reference Emotion Estimation Result in Emotion_Information>

The reference electroencephalogram detection information measured upon calibration and the reference emotion estimation result can be stored in Emotion_information in which the electroencephalogram detection result and biometric information are stored. This makes it possible to perform electroencephalogram detection and emotion estimation by an application program with higher accuracy.

In this description, calibration is adjustment processing for specifying personality for each user, eliminating measurement errors, and improving accuracy.

Specifically, in the calibration, for the first time or the first few times, the reinforcement target behavior common to each user is performed, electroencephalogram measurement in a resting environment is urged, and a questionnaire to the result of the reinforcement target behavior is presented. Then, processing for inputting subjective evaluation is executed, and various configurations and processing are adjusted on the basis of elemental electroencephalogram and biometric information acquired by these processing operations.

Figure 26:
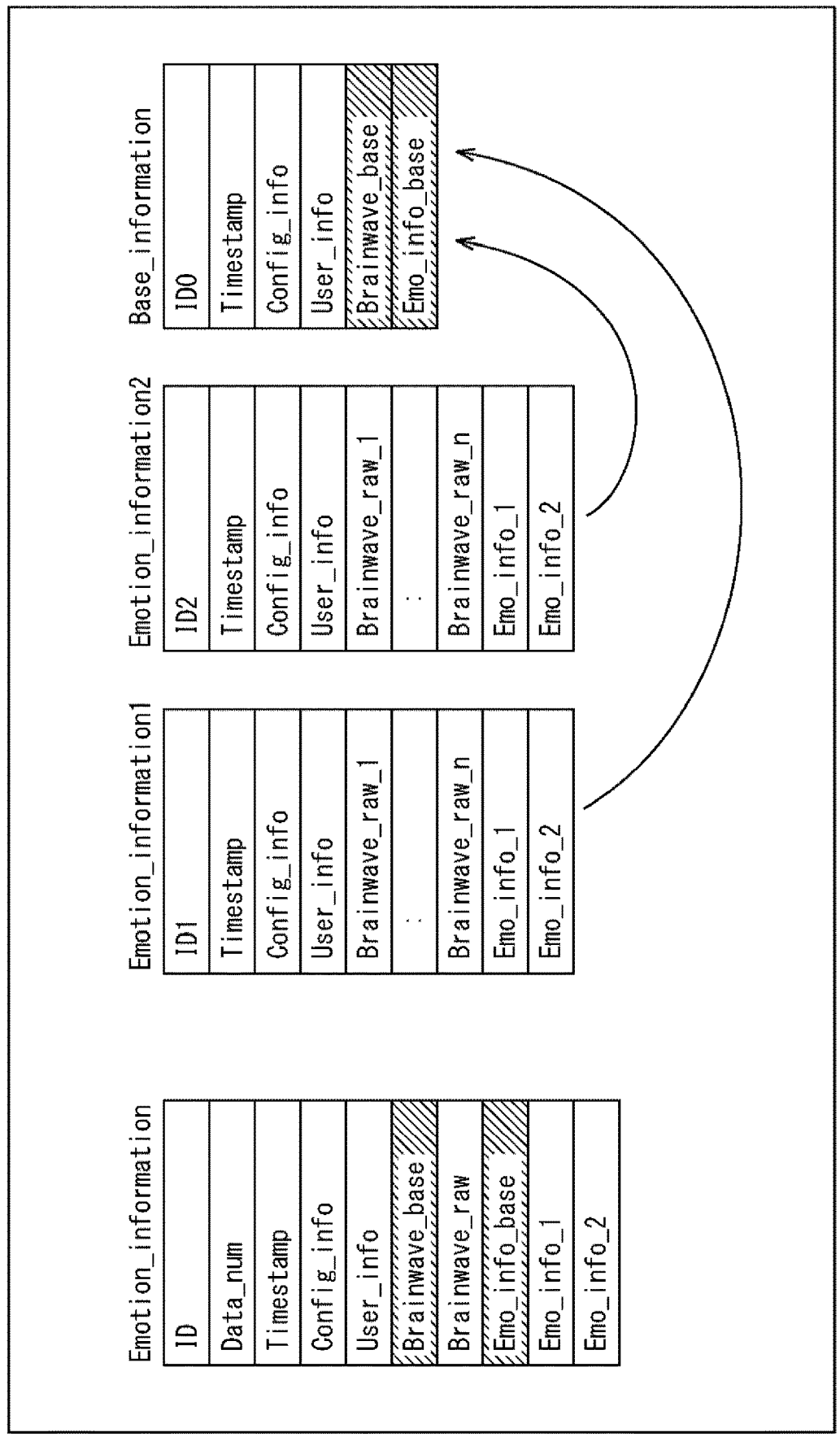
FIG. 26 is a diagram illustrated to describe a second modification.

More specifically, in Emotion_information at the leftmost part of FIG. 26, Brainwave_base is additionally stored as reference electroencephalogram detection information and Emotion_info_base is additionally stored as the reference emotion estimation result in the data structure of normal Emotion_information as indicated by the hatched portion.

Further, as shown in the rightmost part of FIG. 26, an independent metadata file including Brainwave_base that is reference electroencephalogram detection information and Emotion_info_base that is the reference emotion estimation result can be generated.

In this case, Emotion_information1 in which the first electroencephalogram detection result and biometric information is stored and Emotion_information2 in which the second electroencephalogram detection result and biometric information is stored can be independently used by referring to the metadata file.

<<5. Third Modification>>
<Example of Switching Parts of Avatar>

Although the above description is given of, as illustrated in FIG. 11, the example of changing the avatar in the dendrogram depending on the number of dominant emotions, parts of the avatar can be switched depending on a change in emotions for each of larva, sub-adult, and adult.

In other words, a case is conceivable in which the emotion estimation result is obtained from a score of a set of five types of emotions of "excited", "mysterious", "impressed", "I found it", and "great".

Figure 27:
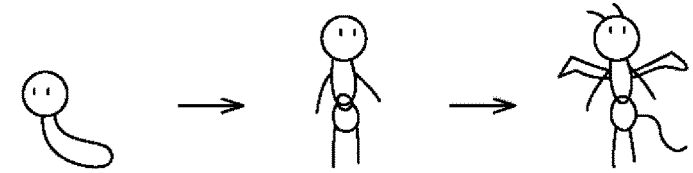
FIG. 27 is a diagram illustrated to describe a third modification.

As illustrated in FIG. 27, the larva is constituted by a "head" part and a "first body" part.

In each part, the materials corresponding to each of the five types of emotions that constitute the emotion set are set.

Then, on the basis of the proportion of the emotion estimation result or the dominant emotion, the type of material corresponding to the relevant emotion is selected.

In one example, in a case where the proportion of emotion of "excited" is 66% and the proportion of emotion of "mysterious" is 33%, if there are three types of parts, "head", "arm", and "body", scores corresponding to the emotion of "excited" are accumulated for two-thirds of the three types of parts, in one example, in two parts of "head" and "arm" of three parts of "head", "arm", and "body". In addition, for one-third of the three parts "head", "arm", and "body", in one example, scores corresponding to the emotion of "mysterious" are accumulated to one part of "body". Then, at the timing when the score exceeds a threshold, the material of the part corresponding to the emotion exceeding the threshold is changed.

In the case of dominant emotion rather than proportion, if the dominant emotion is "excited", the score of the emotion of "excited" is accumulated for any one randomly selected from "head", "arm", and "body".

In addition, as indicated by the circles in FIG. 27, in the larva, the "head" and "first body" parts are changed. Then, when the "head" and "first body" parts are changed, the avatar changes from the larva to the sub-adult.

In this example, although there are no parts in the larva, parts of "arm", "leg", and "second body" in the larva indicated by the triangle mark in FIG. 27 are also changed.

In other words, the part represented by the triangle mark not attached to the current avatar is a hidden part in which only the material information changes and does not appear as an avatar display. Then, when the avatar changes from the larva to the sub-adult, parts corresponding to the information of the material of "arm", "leg", and "second body" at that time are given.

Further, as indicated by the circles in FIG. 27, the sub-adult is constituted by "head", "arm", "leg", and "second body" parts.

Then, the "head", "arm", "leg", and "second body" parts indicated by the circles in FIG. 27 are changed.

In addition, in the sub-adult, it does not exist as a part, but only the information of the material is changed for the "horn", "wing", and "tail" parts in the sub-adult indicated by the triangle mark in FIG. 27.

In other words, only the information of the material is changed for the hidden parts represented by triangle marks not attached to the current avatar. Then, when the avatar changes from the sub-adult to the adult, parts of the type corresponding to the information of the material of "horn", "wing", and "tail" are given.

Furthermore, as illustrated in FIG. 27, the adult is constituted by "head", "arm", "leg", "second body", "horn", "wing", and "tail" parts.

Then, each of "head", "arm", "leg", "second body", "horn", "wing", and "tail" is changed to a part corresponding to the information of the material.

As described above, the avatar can be changed by changing the part of the avatar corresponding to each emotion on the basis of each of the emotion estimation results.

<<6. Fourth Modification>>
<Example of Reflecting Coefficient Depending on Type of Quest in Change of Avatar>

A coefficient depending on the type of quest can be reflected in the change of the avatar. In other words, depending on the contents of the quest, the score of a particular emotion tends to be high or low. Thus, a coefficient for each emotion can be set depending on the contents of the quest, so the score of a particular emotion can be set not too high or too low.

Figure 28:
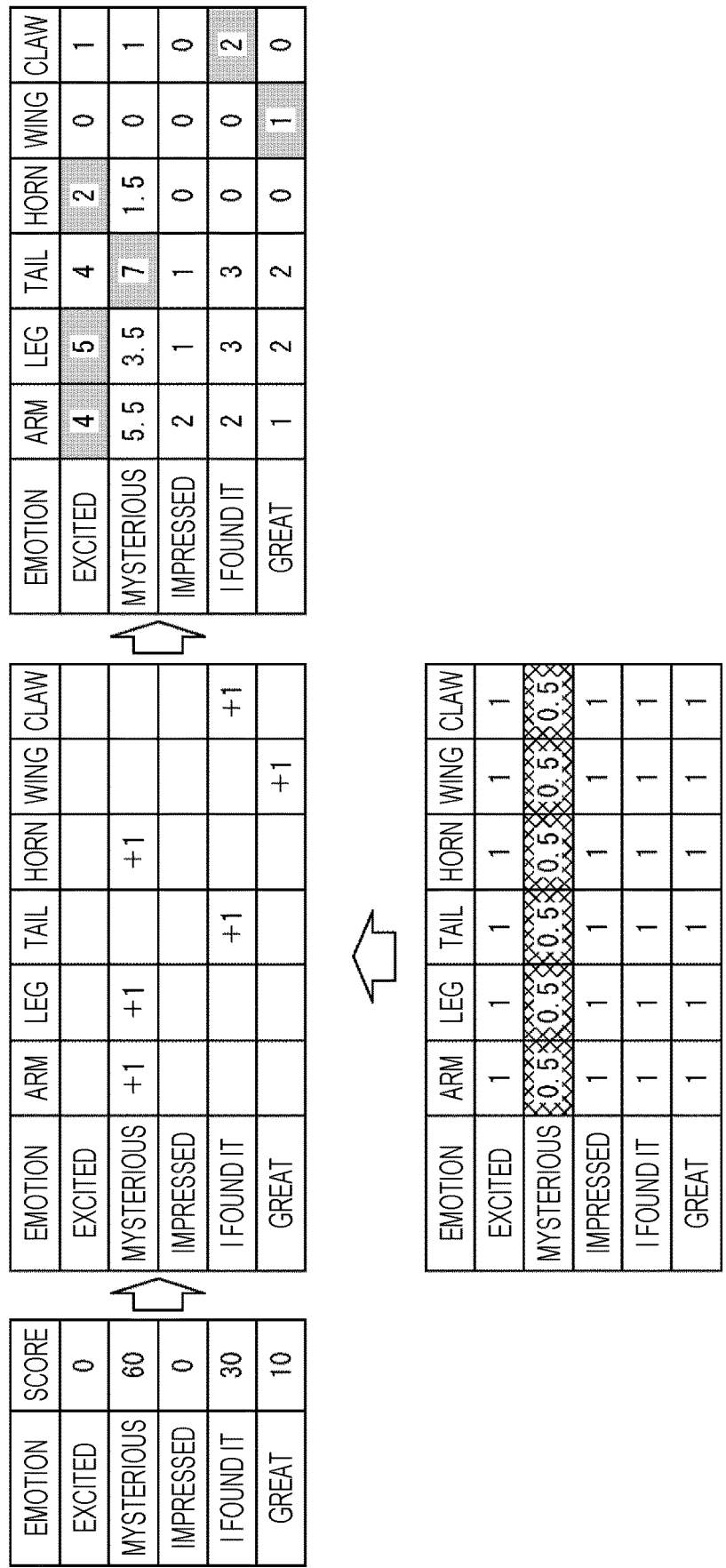
FIG. 28 is a diagram illustrated to describe a fourth modification.

More specifically, on the basis of the information in the short-term change table corresponding to the emotion estimation result shown in the upper left part of FIG. 28, an addition table in which an additional score to be added for each emotion are put together for each part is generated as shown in the upper center part of FIG. 28. Then, each additional score in the addition table is multiplied by a coefficient in the coefficient table in the lower center of FIG. 28, and the integration result of each score is put together in an integration table shown in the upper right part of FIG. 28.

Each part of the avatar is set for each of the five types of emotions of the emotion estimation result, and the part of the type having the highest score is selected and combined for each part in the integration table to determine the avatar.

In one example, in the short-term change table corresponding to the emotion estimation result, a case is conceivable in which there are "excited" of 0, "mysterious" of 60, "impressed" of 0, "I found it" of 30, and "great" of 10, and parts of the avatar are "arm", "leg", "tail", "horn", "wing", and "claw".

In this case, the short-term change table corresponding to the emotion estimation result is the short-term change table shown in the upper left part of FIG. 28.

The addition table is a table in which a score to be added for each emotion is recorded for each part of the avatar on the basis of the short-term change table. In other words, in the case of the addition table shown in the upper center part of FIG. 28, "arm", "leg", and "horn", which are the parts corresponding to the emotion of "mysterious", have a score of 60, and a point of "+1" is assigned. In addition, "tail" and "claw", which are parts corresponding to the emotion of "I found it", have a score of 30, so a point of "+1" is assigned. Furthermore, "wing" corresponding to the emotion of "great" has a score of 10, so a point of "+1" is assigned.

Moreover, in the addition table, the score of each emotion in the short-term change table can be set variously for which part and how many points are assigned. The example in the upper center of FIG. 28 is only an example. In addition, the point to be assigned can be negative or the sum of the points to be assigned can be zero.

The coefficient table in the lower center part of FIG. 28 is a table of coefficients to be multiplied by the score of the addition table, and a coefficient for each corresponding emotion is stored for each part. Each coefficient corresponds to the contents of the quest. In one example, in a case where a high score is likely to be assigned for the emotion of "mysterious" as the emotion estimation result by the contents of the quest, a score of 0.5 may be set as a coefficient corresponding to the emotion of "mysterious" in the addition table as shown in the coefficient table at the bottom center of FIG. 28, and a score of 1 can be set to other coefficients.

In other words, as shown in the coefficient table of FIG. 28, the points of "arm", "leg", and "corner" assigned by the emotion estimation result of "mysterious" in the value of the addition table are all multiplied by a coefficient of 0.5 to be "+0.5".

Furthermore, the integration table shown in the upper right part of FIG. 28 is a table in which points of the addition table are sequentially accumulated every time the reinforcement target behavior is performed. An example is shown in FIG. 28 in which, from the left, parts of the avatar are provided with columns of "arm", "leg", "tail", "horn", "wing", and "claw", and the results of integrating points given by the emotions of "excited", "mysterious", "impressed", "I found it", and "great" are recorded.

In other words, in the integration table in the upper right part of FIG. 28, as the score of each emotion of "arm", "excited" is 4, "mysterious" is 5.5, "impressed" is 2, "I found it" is "2" and "great" is 1.

As the score of each emotion of "leg", "excited" is 5, "mysterious" is 3.5, "impressed" is 1, "I found it" is 3 and "great" is 2.

As the score of each emotion of "tail", "excited" is 4, "mysterious" is 7, "impressed" is 1, "I found it" is 3 and "great" is 2.

As the score of each emotion of "horn", "excited" is 2, "mysterious" is 1.5, "impressed" is 0, "I found it" is 0 and "great" is 0.

As the score of each emotion of "wing", "excited" is 0, "mysterious" is 0, "impressed" is 0, "I found it" is 0 and "great" is 1.

As the score of each emotion of "claw", "excited" is 1, "mysterious" is 1, "impressed" is 0, "I found it" is 2 and "great" is 0.

The information processing unit 93 determines the avatar by selecting the type that is set in association with the emotion with the highest score among the parts in the integration table.

In other words, in the integration table shown in the upper right part of FIG. 28, the part of "arm" is determined as the type that is set in association with the emotion of "mysterious" whose score is "5.5".

The part of the "leg" is determined as the type that is set in association with the emotion of "excited" whose score is "5".

The part of the "tail" is determined as the type that is set in association with the emotion of "mysterious" whose score is "7".

The part of the "horn" is determined as the type that is set in association with the emotion of "excited" whose score is "2".

The part of the "wind" is determined as the type that is set in association with the emotion of "great" whose score is "1".

The part of the "claw" is determined as the type that is set in association with the emotion of "I found it" whose score is "2".

In the integration table shown in the right part of FIG. 28, the squares to which colors are assigned indicate the type of parts that are currently set. Accordingly, the integration table is updated as shown in the upper right part of FIG. 28, so the part of "arm" is changed from the type that is set in association with the current emotion of "excited" to the type that is set in association with the emotion of "mysterious".

As described above, every time the reinforcement target behavior is repeated depending on the quest and the short-term change table is supplied, the corresponding addition table is generated and a value multiplied by the coefficient of the coefficient table, which is set depending on the quest, is added, and then the integration table is updated sequentially. Then, for each part in the integration table, the avatar is changed by configuring the avatar by combining the parts of the type that is set in association with the emotion having the highest score.

This allows the coefficient corresponding to the quest to be reflected in the change of the avatar, so the avatar can be appropriately changed depending on the quest.

Consequently, it is possible to reinforce the reinforcement target behavior by stimulating the user's willingness to change the avatar without causing the user's consciousness.

Moreover, although the above description is given of the example of adjusting the score using the coefficient, in one example, the electroencephalogram measurement is performed in conjunction with the quest, so in a case where it is clear that the emotion of "mysterious" such as during an event is in a strong state by a quest such as "find mysterious thing", it can be added by subtracting the score relating to the emotion of "mysterious", or the strength can be added by paying attention to the emotion of "mysterious".

In addition, the integration table at the upper right in FIG. 28 corresponds to the long-term change table described with reference to FIGS. 13 and 14. In other words, in the long-term change table described with reference to FIGS. 13 and 14, the number of times of specification of the dominant emotion is accumulated for each emotion on the basis of the emotion estimation result, and the avatar changes depending on the number of times of specification of the dominant emotion. On the other hand, in the integration table of FIG. 28, the score itself is cumulatively accumulated for each part of the avatar for each emotion of the emotion estimation result, and the type that is set in association with the emotion with the highest score for each part is determined. Both are information regarding the short-term change table based on the emotion estimation result that is supplied every time the reinforcement target behavior is performed, and the long-term change table is updated, and the avatar changes on the basis of the number of times of specification of a dominant emotion that is cumulatively managed in the long-term change table or the score of each part.

Furthermore, the coefficient can be switched not only depending on the type of quest, but also, in one example, in a case where a special emotion such as a rare emotion is detected among the users having emotions detected for the first time, an unusual emotion in the same quest, or the same attribute (same grade, same race, or same gender) in the same users.

<<7. Fifth Modification>>

<Example of Sharing One Avatar by a Plurality of Users>

Although the above description is given of the example in which one user uses one avatar, one avatar can be shared by a plurality of users.

In other words, one avatar can be generated and changed by collecting emotions of a plurality of users.

Figure 29:
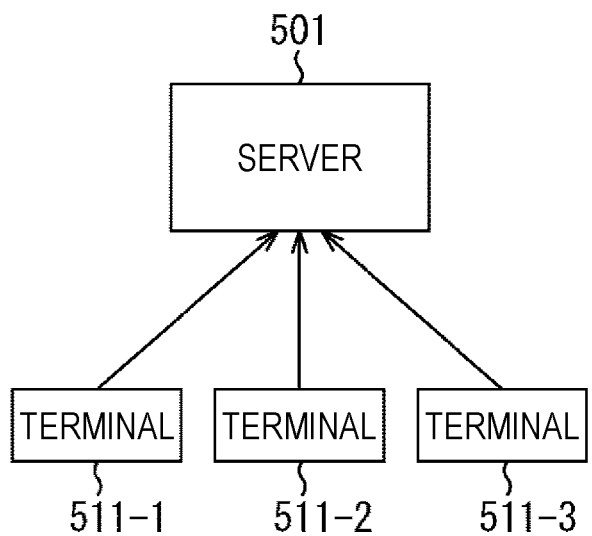
FIG. 29 is a diagram illustrated to describe a fifth modification.

FIG. 29 illustrates an exemplary configuration of an information processing system in which emotions of a plurality of users are collected to generate one avatar and change it.

The information processing system of FIG. 29 includes a server 501 and terminals 511-1 to 511-3 that are used by the respective users.

Each of the terminals 511-1 to 511-3 has a configuration corresponding to the information processing system 11 of FIG. 3 and transmits the electroencephalogram detection information and biometric information of each user to the server 501.

The server 501 has a function similar to the information processing unit 93 in the information processing apparatus 41, acquires electroencephalogram detection information and biometric information of a plurality of users, which are supplied from the terminals 511-1 to 511-3, creates the short-term change table on the basis of the electroencephalogram detection information and biometric information of a plurality of users, reflects it in the long-term change table, and transmits an image that presents an avatar by changing the avatar to the terminals 511-1 to 511-3. In addition, the server 501 transmits an image that presents a quest to the terminals 511-1 to 511-3.

The terminals 511-1 to 511-3 repeatedly urge to perform the reinforcement target behavior by displaying an image of the quest of FIG. 4 or a display image of the avatar of FIG. 15 as the quest transmitted from the server 501, and repeat the processing of displaying the avatar.

More specifically, the server 501 uses, in one example, an average value, a median value, a maximum value, a minimum value, or other statistical values of electroencephalogram detection information and biometric information of a plurality of users, so the server 501 executes the processing similar to the processing in a case where the electroencephalogram detection information and the biometric information of a plurality of users are performed as if the electroencephalogram detection information and the biometric information of substantially one user are performed. However, the electroencephalogram detection information and biometric information of a plurality of users that are statistically obtained can be reflected in the change of the avatar.

The processing described above makes it possible to create an avatar representing a class, for example, an avatar representing a plurality of fans who supports a certain idol, or an avatar for each idol support group. This makes it possible to prevent the user from getting bored, in one example, by connecting to a quest or the like of a support battle.

In addition, it is possible to reinforce the reinforcement target behavior with an incentive for feedback not to a user itself but to other persons than the user (belonging group or support target). In other words, the presentation of an avatar to another person can be an incentive for the user's reinforcement target behavior.

In addition, the personality of organization, corporation, and group is capable of being quantitatively expressed using an avatar.

Furthermore, it is possible to reinforce the reinforcement target behavior by setting a category, such as gender, age, and region, which defines a plurality of users.

In addition, a group of people with the same purpose can be formed, so it is possible to change and reinforce one avatar, in one example, for a group of a plurality of people with the same purpose. In addition, it is also possible to set a plurality of avatars for each group and to cause the groups to compete for the change, resulting in the achievement of reinforcing the reinforcement target behavior for the entire group.

Furthermore, in a region or the like, it is possible not to reinforce one person's behavior continuously but to reinforce the reinforcement target behavior by an unspecified number of users who visit the place. In other words, an avatar representing a region, a local avatar, an avatar for each event, an avatar representing art in a museum or the like can be set.

In other words, the avatar can be set and changed for each piece of art by accumulating the viewer's emotion for each piece of art in the museum using the position information.

Alternatively, an avatar that personifies the tendency of a viewer/listener of predetermined content can be set, so a character based on the avatar is created for each viewer/listener of the content.

<<8. Sixth Modification>>

<Example of Enabling Conversation Such as Chatting With Another Person's Avatar>

Although the above description is given of the example in which one avatar is used by one person or is shared by a plurality of persons, a conversation such as chatting can be performed with another person's avatar.

Figure 30:
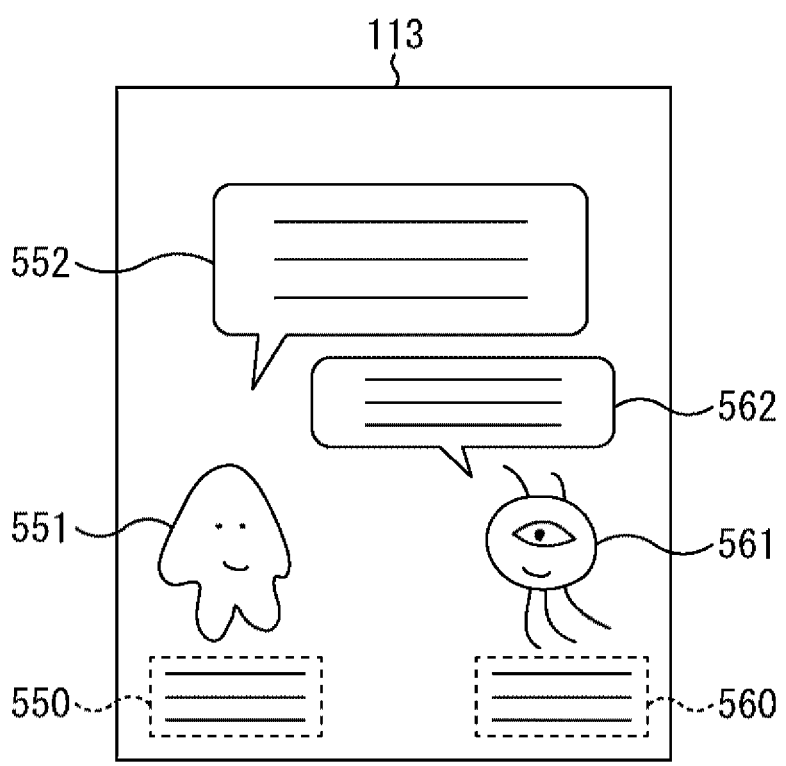
FIG. 30 is a diagram illustrated to describe a display example in a sixth modification.

In one example, as illustrated in FIG. 30, a plurality of avatars may be allowed to join a conversation.

In FIG. 30, avatars 551 and 561 are respectively displayed on the left and right in the middle of the display unit 113. The profiles or the like of the avatars 551 and 561 can be described in profile portions 550 and 560 respectively provided in the lower portions of the avatars 551 and 561. In addition, the avatars 551 and 561 are provided with markup balloons 552 and 562, respectively, and each user uses a function or the like of the touch panel of the display unit 113 of each display apparatus 42 and makes a chat with natural language.

The avatars 551 and 561 both can be avatars generated by repeating the user's reinforcement specifying behavior. Furthermore, one of the avatars can be an avatar that is changed by a positive score of the user's emotion estimation result, and the other avatar can be an avatar that is changed by a negative score of the user's emotion estimation result. In this way, in the case the user is caused to presents a plurality of avatars, in one example, using the chatting function, one avatar can ask the other avatar for advice on the user's own reinforcement target behavior.

In addition, the advice from the avatar can be advice that reflects results depending on the emotion estimation of the user.

Furthermore, the user can make an inquiry to the avatar so that the avatar presents advice. In this case, the user can objectively view the user oneself or can be urged to make a decision through communication with an avatar as "other self" reflecting the user's own personality.

In addition, an opponent to be communicated with another user is an avatar, so it is possible to achieve communication through real intention.

In addition, in a case where the user makes a chat or the like with another person's avatar, the user's avatar can be presented on the other person's device.

Furthermore, an avatar can be displayed to a child's parent or lover, and the emotion estimation result of the current user can be presented via the displayed avatar.

In addition, a user's avatar and another user's avatar can have a conversation and observe its situation.

Furthermore, compatibility fortune-telling can be performed using an avatar.

In addition, it can be possible to know the perspectives and values of friends by making it possible to select suitable avatars of friends for advice, and by applying this, in one example, it can also be used for searching marriage partners at marriage counselors and recruiting human resources in companies.

Furthermore, communication with another user's avatar can be performed as a mutual permission system or can be able to communicate on the basis of information regarding its location.

In addition, in one example, it is applicable to a battle game.

In other words, in a case where it is applied to a battle game between avatars, the parameters between avatars can be displayed. In addition, commands that are usable depending on the change in avatars can be changed so that the user can select an action (attack, defense, etc.) from among these commands. Furthermore, even when there is no command input from the user at the time of a game battle, the battle can be automatically performed by predicting an action based on information regarding accumulated emotion.

The attribute of the avatar can be distributed depending on the dominant emotion based on the emotion estimation result, and the distributed attribute of the avatar can be set in a three-way relationship. In this event, the attribute of the avatar main body fixed on the basis of the estimation result of the user's emotion and the attribute generated on the basis of the estimation result of the user's emotion can be combined with items that are exchangeable with other users. Furthermore, in a case where a plurality of avatars is generated, the user can select an avatar as appropriate so as to fight other avatars. In addition, a plurality of avatars can be collected or exchanged with avatars of other users.

<<9. Seventh Modification>>

<Example where Reinforcement Target Behavior is Education or Learning>

Although the above description is given of the example in which the reinforcement target behavior is the photographing, the reinforcement target behavior can be other behavior as long as it is behavior that the user wants to reinforce without causing the user's consciousness, in one example, it can be education or learning.

In one example, as illustrated in FIG. 31, an avatar is set for each curriculum, and by raising the willingness that wants to change the avatar depending on each curriculum, the behavior such as education and learning of each curriculum can be reinforced.

In FIG. 31, the national language, arithmetic, and science are set as curricula, and an avatar corresponding to each is set. In addition, it shows each avatar that changes depending on a parameter that is set, in one example, by the learning progress of each curriculum, and in FIG. 31, the parameter of the national language is Lv4, the parameter of arithmetic is Lv20, and the parameter of science is Lv12, so an avatar corresponding to each level is set. Moreover, although FIG. 31 shows an example in which different avatars are set for each curriculum, the avatar can be one type, and the display state can be changed depending on the curriculum being good at or the attitude to study.

In addition, in the case where the behavior of education or learning is the reinforcement target behavior, the learning timing can be controlled on the basis of the optimum learning method, learning time zone, and learning sensation depending on the quest.

In this case, the user can be urged to perform the reinforcement target behavior in the form that the avatar advises by a quest. In addition, in this event, the electroencephalogram and biometric information can be detected using the timing advised by the avatar as a reference.

In addition, the change in avatars or accumulation of emotion estimation results can be linked to the learning unit.

Furthermore, a curriculum depending on the user's mood can be set by the quest. In addition, a quest can be presented at the optimal timing for doing a weak curriculum. Furthermore, the quest can be presented at an optimal timing depending on the forgetting curve. It is known that learning depending on the forgetting curve is highly effective for memory retention in education. In addition, by expressing the emotion estimation result using an avatar, it is possible to present an objective evaluation of the learning result as a qualitative index indicating trying hard, not a quantitative index such as a test.

In addition, in the case where education or learning is set as the reinforcement target behavior, the emotion set to be estimated can include emotions relating to learning efficiencies such as concentration and immersion. Furthermore, the penalty can be given for no concentration rather than the incentive is given for concentration. In addition, the avatar can be changed on the basis of the negative emotion. Furthermore, the avatar can be changed so that a qualitative approach such as "tried hard" can be evaluated. In this case, in one example, the change in avatars can be checked by not only the user by regarding it as an evaluation for the reinforcement target behavior but also a third party such as the user's mentor by regarding it as the evaluation for the reinforcement target behavior. The mentor can decide the guidance contents for the reinforcement target behavior by evaluation of the avatar. In addition, even if the score relating to learning is not increased, the quest can be set so as to evaluate the trying hard and make the hard work harder. Then, the avatar can be changed depending on the learning contents.

The avatar can have an appearance that reflects the curriculum being good at. In addition, a curriculum being poor at is estimated, and the avatar changes so that the avatar becomes strong as the curriculum being poor at is overcame and its strength increases, and the fact that strong point increases or the fact that the weak point is overcome can be reflected in the form or parameter of the avatar.

Moreover, examples of the education used herein include study (cognitive education), school education, non-cognitive education, communication, morality, sensitivity, things not taught at school, martial arts spirit, club activities, sports training, Zen meditation, spiritual unity, mindfulness, training of hobbies such as yoga, and achievement of goal in a broad sense.

Moreover, the reinforcement target behavior can be, in one example, the behavior of taking communication.

In this case, the electroencephalogram can be measured before and after the start of a conversation with another person as a trigger. In addition, the electroencephalogram to be measured can be, rather than the user's own electroencephalogram, another user's electroencephalogram. The measurement of the electroencephalogram of another user makes it possible to quantify and visualize the emotion that the other user has with respect to the user or the evaluations with respect to the user.

Furthermore, the avatar can be changed on the basis of the reaction of the opponent depending on the user's own utterance.

Consequently, the user's own conversation characteristics can be recognized. In this event, by setting a conversation want to have or a user oneself want to be or recommending such an appearance, it is possible to perform the reinforcement of conversation, which is to obtain such appearance, want to have as short-term and long-term neurofeedback. In addition, the setting of the conversation that is to have makes it possible to have a conversation that is gentle, interesting, or ingenious.

In this case, the content of education of communication can be used for salespersons' sales talks, presentation exercises, and communication exercises with subordinates upon management jobs.

In addition, in this case, the avatar can give advice depending on the habit of conversation, and in this event, it is possible to provide guidance having the set "oneself want to be" as a goal.

Furthermore, the avatar can be changed so that the effect of coaching can be understood.

In addition, in the case where communication is the reinforcement target behavior, if the estimation result of the opponent's emotion is reflected without any modification, the emotion estimation result of another user is reflected in the user's avatar, so the user's own emotion estimation result that is estimated on the basis of the reaction of the opponent can be reflected instead of reflecting the emotion estimation result of the opponent without any modification.

Furthermore, different avatars can be changed depending on the opponents.

In addition, interest and concern can be estimated on the basis of the avatar obtained by accumulating emotion estimation results, so it is applicable, in one example, to advertisement and product recommendation.

In other words, product recommendations corresponding to tendency to be known from emotion estimation results and avatars, product and service recommendations corresponding to emotion estimation results, and product recommendations based on purchase logs of people with similar emotional trends from the same emotion estimation result, recommendations of content (movie or music) can be performed.

Furthermore, on the basis of emotion estimation results or avatars, it is applicable to dynamic changes in contents of content, product advertisement layout, changes in the web configuration, real-time changes depending on the current state, and changes depending on personality types.

In addition, the search result can be optimized on the basis of the emotion estimation result.

Furthermore, the emotion estimation result can be incorporated into the search algorithm.

In addition, the avatar reflects the potential awareness of the user, which is obtained by repetitive long-term measurement of the electroencephalogram detection result and biometric information when the user performs the reinforcement target behavior. Thus, a product or the like can be recommended with high accuracy, thereby performing an effective product recommendation.

Specifically, in a case where learning is the reinforcement target behavior, a product that assists learning can be recommended. In other words, the product relating to the reinforcement target behavior can be set as the product to be recommended.

<<10. Eighth Modification>>
<Example Using Virtual Reality (VR) Goggle-Type Electroencephalograph>

Although the above description is given of the information processing system 11 including the electroencephalograph 31, the biometric sensor 32, the information processing apparatus 41, and the display apparatus 42, in one example, an electroencephalograph and a display apparatus can be integrated by employing a virtual reality (VR) goggle-type electroencephalograph.

Figure 32:
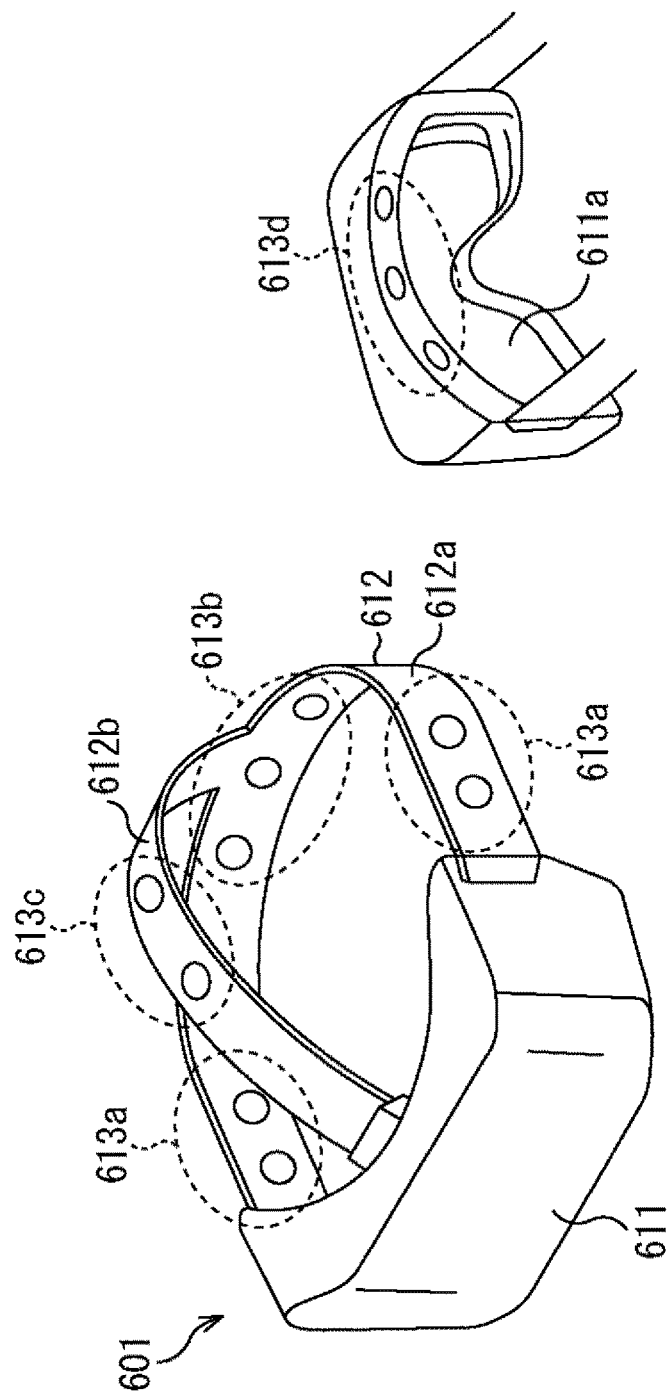
FIG. 32 is a diagram illustrated to describe an eighth modification.

FIG. 32 illustrates an exemplary configuration of a VR goggle-type electroencephalograph 601 in which the electroencephalograph 31 and the display unit 113 of the display apparatus 42 are integrated. The left part of FIG. 32 is a bird's eye view and the right part of FIG. 32 is a perspective view of a goggle part 611 from behind.

The VR goggle-type electroencephalograph 601 includes the goggle part 611 and a belt 612, and is fixed to the head of a user 21 by the belt 612 with the goggle part 611 in contact with the eyes of the user 21.

The goggle part 611 is provided with a display unit corresponding to the display unit 113 of the display apparatus 42 on a back surface portion 611a in the figure for displaying a display image on the display unit 113.

Further, the belt 612 includes a portion 612a wound around the side surface of the head and a portion 612b wound around the top of the head.

Two electrodes 613b that are in contact with the head of the user 21 are provided on the left and right sides, respectively, of the side surface at the portion 612a of the belt 612. In addition, three electrodes 613c that are in contact with the head of the user 21 are provided on the back of the head of the portion 612a. Furthermore, two electrodes 613a that are in contact with the head of the user 21 are provided on the top of the portion 612b of the belt 612. In addition, three electrodes 613d are provided on the upper portion that is in contact with the forehead of the back surface portion 611a of the goggle part 611. The electrodes 613a to 613d correspond to the electrodes 31a to 31c in FIG. 2.

The VR goggle-type electroencephalograph 601 measures the electroencephalogram by the 12 electrodes 613a to 613d.

In addition, the user is able to reinforce the reinforcement target behavior while viewing the image displayed by the goggles part 611.

Moreover, although the number of electrodes is 12 in this example, the number of electrodes can be a number other than 12, and even if the number of electrodes is 12, some electrodes selected from these electrodes can be used.

Figure 33:
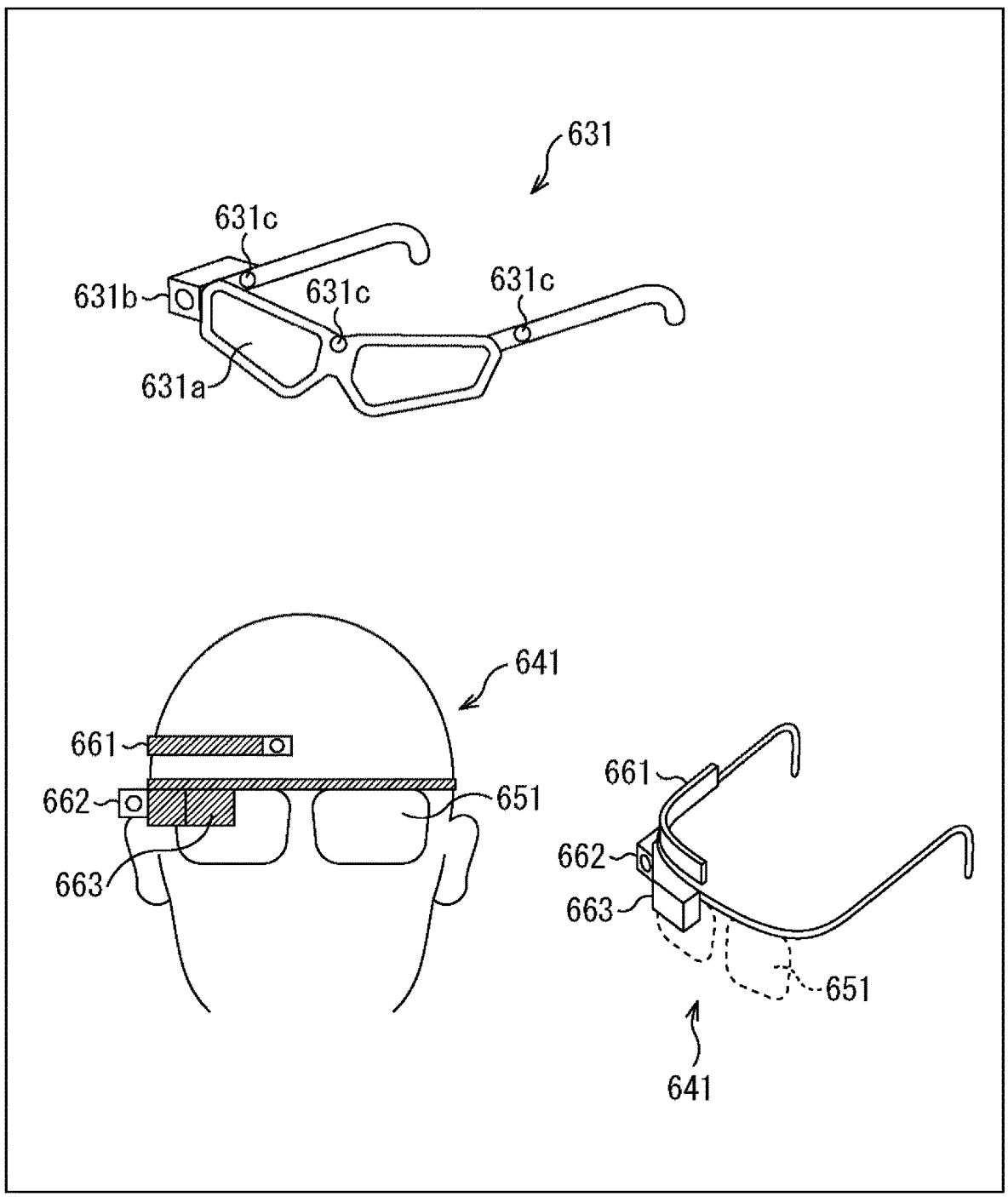
FIG. 33 is a diagram illustrated to describe a ninth modification.

In addition, the VR goggle-type electroencephalograph can have a configuration to be arranged on the back of the head, the top of the head, the side of the head, or the like in addition to the configuration as illustrated in FIG. 33. In addition, the VR goggle-type electroencephalograph can measure individual electroencephalogram depending on the position of the head where it is placed, so the design considering which position of the head to be placed or which electrode to be used can be performed depending its application or use.

<<11. Ninth Modification>>

<Example Using Augmented Reality (AR) Glass-Type Electroencephalograph>

Although the above description is given of the VR goggle-type electroencephalograph, an augmented reality (AR) glass-type electroencephalograph can be used.

FIG. 33 illustrates an exemplary configuration of the AR glass-type electroencephalograph. The upper part of FIG. 33 shows an exemplary configuration of an integrated AR glass-type electroencephalograph and the lower part of FIG. 33 shows an exemplary configuration in which the function of the AR glass-type electroencephalograph is added to existing glasses.

An AR glass-type electroencephalograph 631 shown on the left side of FIG. 33 includes a transparent display 631*a*, an imaging unit 631*b*, and an electrode 631*c*.

The transparent display 631*a* is a display that is viewable in a state in which the outside world is transmitted from the user's eyes and that is viewable in a state in which an AR display image is superimposed, and has a configuration corresponding to the display unit 113 of the display apparatus 42.

The imaging unit 631*b* has a configuration corresponding to the imaging unit 94 in the information processing apparatus 41.

The electrode 613*c* is an electrode that is in contact with the scalp between the middle of the forehead and the left and right temples and corresponds to the electrodes 31*a* to 31*c* in FIG. 2.

In addition, an AR glass-type electroencephalograph 641 attached to existing glasses 651 shown in the lower part of FIG. 33 includes an electrode 661, an imaging unit 662, and a projector 663.

The electrode 661 is an electrode in contact with the head of the user 21 and corresponds to the electrodes 31*a* to 31*c* in FIG. 2.

The imaging unit 662 has a configuration corresponding to the imaging unit 94 in the information processing apparatus 41.

The projector 663 projects an image directly on the eyes of the user 21 so that the image on which the AR image is superimposed to be viewed, and has a configuration corresponding to the display unit 113 of the display apparatus 42.

The electroencephalograph 631 or 641 is attached to the user so that the user is able to simultaneously view the real world and information superimposed in an augmentation form on the real world.

Figure 34:
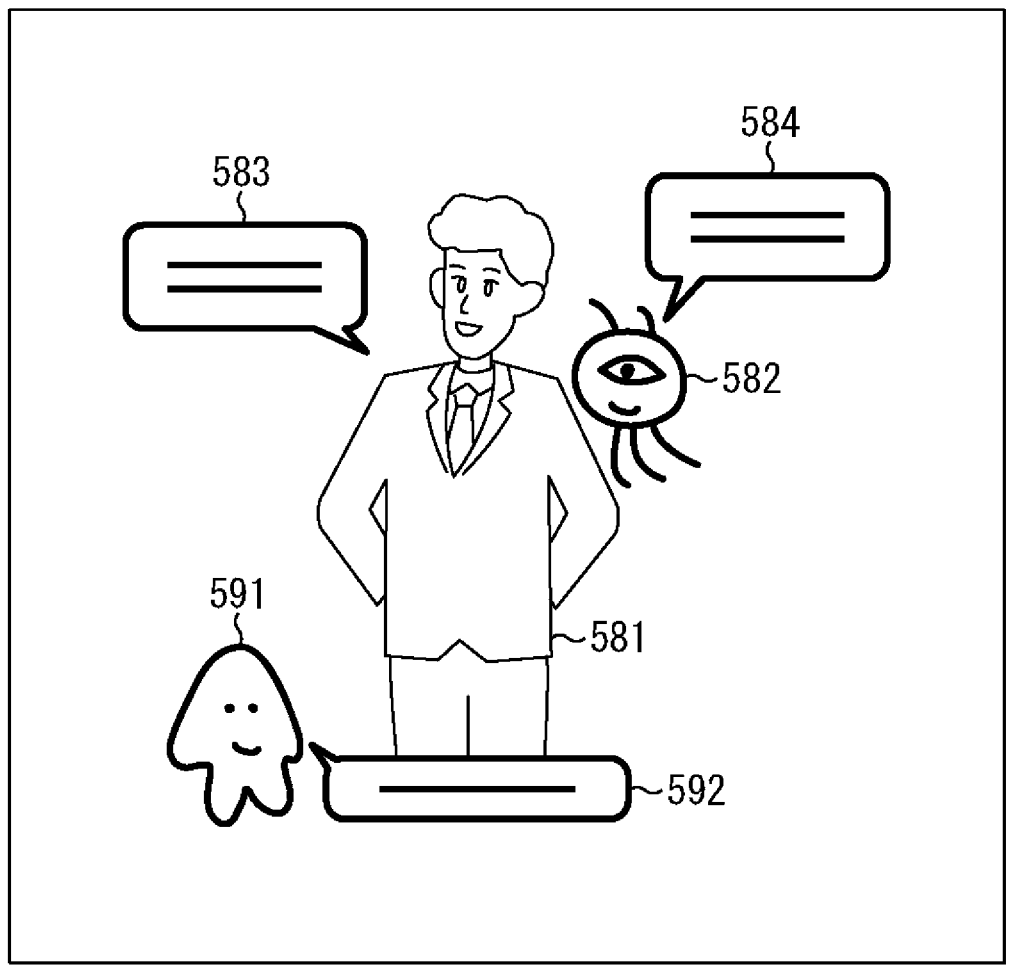
FIG. 34 is a diagram illustrated to describe a display example in the ninth modification.

For this reason, in one example, it is possible to achieve a display image as illustrated in FIG. 34.

FIG. 34 illustrates an example of an image viewed by wearing the AR glass-type electroencephalograph 631 or 641. In FIG. 34, in a state in which another user 581 in the real world is able to directly view, an image in which a user's own avatar 591, a markup balloon 592 of the user's own avatar 591, an opponent avatar 582, a markup balloon 583 of another user, and a markup balloon 584 of the opponent avatar 582 are superimposed on the real world is shown.

Figure 35:
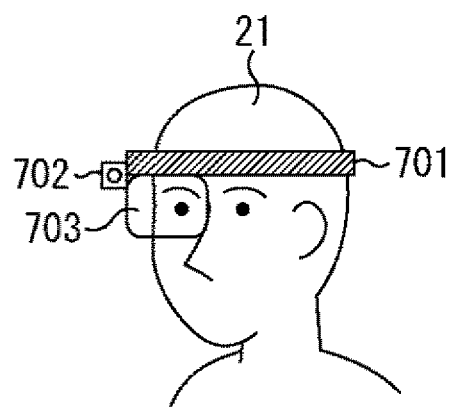
FIG. 35 is a diagram illustrated to describe a tenth modification.

In addition, the AR glass-type electroencephalograph can have a configuration to be arranged on the back of the head, the top of the head, the side of the head, or the like in addition to the configuration as illustrated in FIG. 35. In addition, the AR glass-type electroencephalograph can measure individual electroencephalogram depending on the position of the head where it is placed, so the design considering which position of the head to be placed or which electrode to be used can be performed depending its application or use.

<<12. Tenth Modification>>

<Example of Electroencephalograph Integrated with Configuration of Information Processing System>

Although the above description is given of the example of using the AR glass-type electroencephalograph, the configuration of the information processing system 11 can be integrated with the electroencephalograph.

FIG. 35 illustrates an exemplary configuration in a case where the configuration of the information processing system 11 and the electroencephalograph are integrated.

In other words, an information processing apparatus 701 in which the configuration of the information processing system 11 and the electroencephalograph are integrated is wound around the head of the user 21 in a belt shape, is provided with an imaging unit 702 on the right head, and is provided with a see-through display unit 703 on the right eye.

Figure 36:
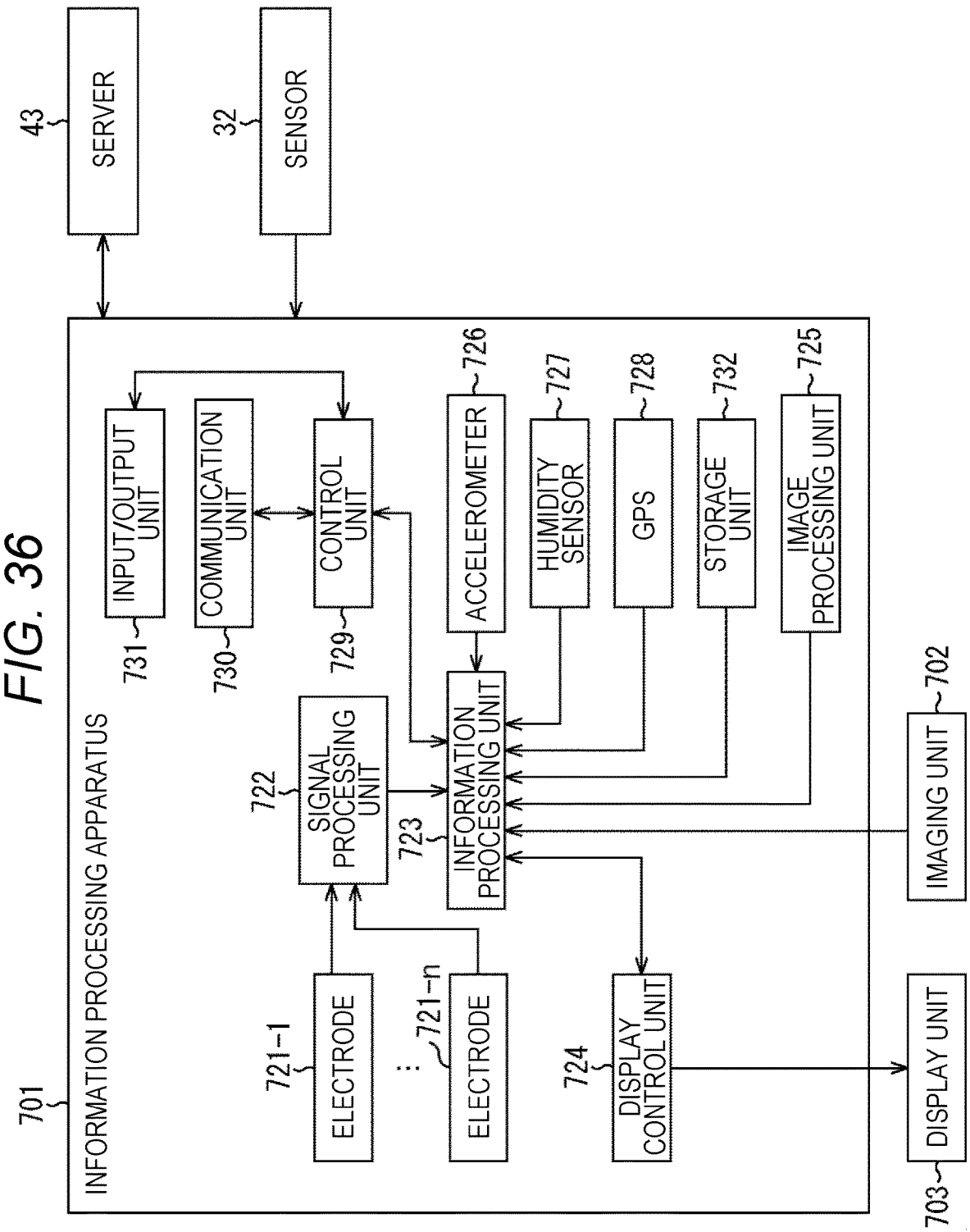
FIG. 36 is a diagram illustrated to describe the tenth modification.

As illustrated in FIG. 36, the information processing apparatus 701 includes electrodes 721-1 and 721-2, a signal processing unit 722, an information processing unit 723, a display control unit 724, an image processing unit 725, an accelerometer 726, and a temperature sensor 727, a GPS 728, a control unit 729, a communication unit 730, an input/output unit 731, and a storage unit 732.

As described above, the integral configuration enables real-time analysis and it makes communication unnecessary, so it can be used offline and power consumption is small, resulting in enabling long-term driving with battery.

Moreover, the electrodes 721-1 and 721-2 correspond to the electrodes 71-1 and 71-2 in FIG. 3 and the signal processing unit 722 corresponds to the signal processing unit 72 in FIG. 3. The information processing unit 723 and the image processing unit 725 correspond to the information processing unit 93 and the image processing unit 95, respectively. The control unit 729, the communication unit 730, the input/output unit 731, and the storage unit 732 correspond to the control unit 91, the communication unit 92, the input/output unit 112, and the storage unit 96, respectively. Thus, the description thereof will be omitted. In addition, the operation thereof is basically similar to that of the information processing system of FIG. 3, so the description will be omitted.

<<13. Example of Execution by Software>>

In this description, the series of the processing described above is executable by hardware but is also executable by software. In a case in which the series of the processing is executed by software, a program included in the software is installed from a recording medium, in one example, to a computer built into dedicated hardware or a general-purpose personal computer capable of executing various functions by installing various programs, or the like.

Figure 37:
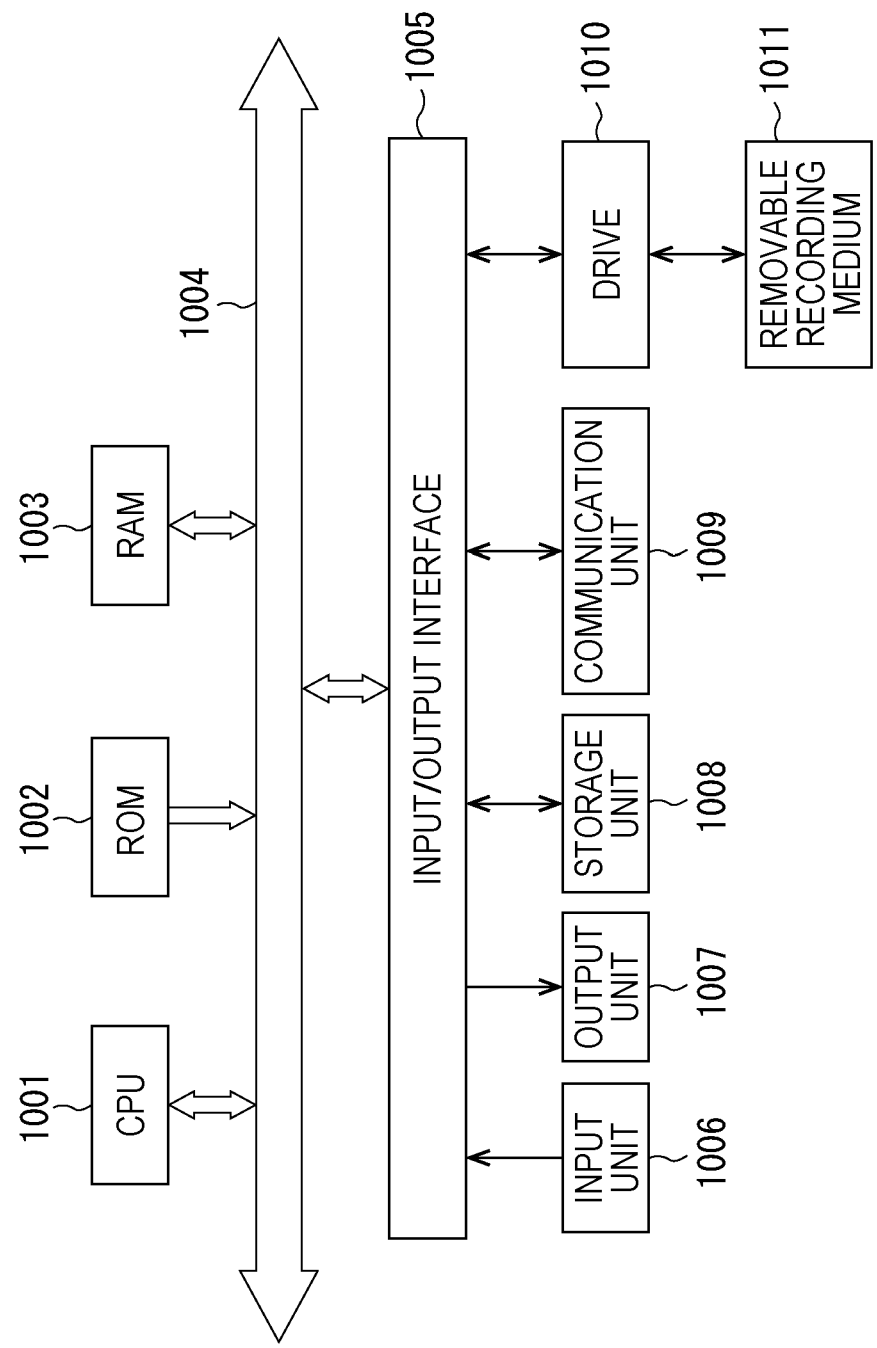
FIG. 37 is a diagram illustrated to describe an exemplary configuration of a general-purpose personal computer.

FIG. 37 shows a configuration example of a general-purpose personal computer. This personal computer has a central processing unit (CPU) 1001 built therein. An input/output interface 1005 is connected to the CPU 1001 via a bus 1004. A read-only memory (ROM) 1002 and a random-access memory (RAM) 1003 are connected to the bus 1004.

An input unit 1006 including an input device such as a keyboard and a mouse through which the user inputs an operation command, an output unit 1007 that outputs a processing operation screen or an image of a processing result to a display device, a storage unit 1008 that includes a hard disk drive or the like storing a program or various data, and a communication unit 1009 that includes a local area network (LAN) adapter or the like and executes communication processing through a network represented by the Internet are connected to the input/output interface 1005. In addition, a magnetic disk (including a flexible disk), an optical disk (including a compact disc-read only memory (CD-ROM) and a digital versatile disc (DVD)), a magneto-optical disk (including a mini disc (MD)), or a drive 1010 that reads and writes data from and to a removable recording medium 1011 such as a semiconductor memory is connected to the input/output interface 1005.

The CPU 1001 executes various processing in accordance with the program stored in the ROM 1002 or the program that is read from the magnetic disk, the optical disk, the magneto-optical disk, or the removable recording medium 1011 such as a semiconductor memory, installed in the storage unit 1008, and loaded to the RAM 1003 from the storage unit 1008. The RAM 1003 also appropriately stores data necessary for the CPU 1001 to execute various processing.

In the computer configured as described above, the CPU 1001 loads a program that is stored, for example, in the storage unit 1008 onto the RAM 1003 via the input/output interface 1005 and the bus 1004, and executes the program, thereby performing the above-described series of processing.

For example, programs to be executed by the computer (CPU 1001) can be recorded and provided in the removable recording medium 1011, which is a packaged medium or the like. In addition, programs can be provided via a wired or wireless transmission medium such as a local area network, the Internet, and digital satellite broadcasting.

In the computer, by mounting the removable recording medium 1011 onto the drive 1010, programs can be installed into the storage unit 1008 via the input/output interface 1005. Programs can also be received by the communication unit 1009 via a wired or wireless transmission medium and installed into the storage unit 1008. In addition, programs can be installed in advance into the ROM 1002 or the storage unit 1008.

Note that a program executed by the computer may be a program in which processing is chronologically carried out in a time series in the order described herein or may be a program in which processing is carried out in parallel or at necessary timing, such as when the processing is called.

Moreover, the information processing apparatus 41 in FIG. 3 corresponds to the personal computer in FIG. 37.

Further, in this specification, a system has the meaning of a set of a plurality of structural elements (such as an apparatus or a module (part)), and does not take into account whether or not all the structural elements are in the same casing. Accordingly, a plurality of devices that is contained in different housings and connected via a network and one device in which a plurality of modules is contained in one housing are both systems.

Note that an embodiment of the present disclosure is not limited to the embodiments described above, and various changes and modifications may be made without departing from the scope of the present disclosure.

For example, the present disclosure can adopt a configuration of cloud computing, in which a plurality of devices shares a single function via a network and perform processing in collaboration.

Furthermore, each step in the above-described flowcharts can be executed by a single device or shared and executed by a plurality of devices.

Furthermore, in the case where a plurality of processes is included in one step, the plurality of processes included in this one step can be executed by one device or executed by being allocated to a plurality of devices.

Further, the present disclosure may include the following configuration.

<1> An information processing apparatus including:
an information processing unit configured to change characteristics of an avatar determined by a previous emotion estimation result to other characteristics on the basis of an emotion estimation result estimated on the basis of an electroencephalogram detected in response to reinforcement target behavior and present the characteristics.

<2> The information processing apparatus according to <1>,
in which the information processing unit presents information used to urge the reinforcement target behavior, and
the information processing apparatus further includes an electroencephalogram detection unit configured to detect the electroencephalogram at a predetermined timing based on a timing of executing the reinforcement target behavior.

<3> The information processing apparatus according to <2>,
in which the electroencephalogram detection unit detects the electroencephalogram at the timing of executing the reinforcement target behavior, during a period from timing before a predetermined time of the timing of executing the reinforcement target behavior to timing after a predetermined time of the timing of executing the reinforcement target behavior, or during a predetermined period from a timing of a predetermined time before the timing of executing the reinforcement target behavior.

<4> The information processing apparatus according to any one of <1> to <3>,
in which the avatar is a form of representation for causing a user to recognize the emotion estimation result.

<5> The information processing apparatus according to any one of <1> to <4>,
in which the characteristics are an appearance of the avatar, displayed contents of a text format, voice, vibration, smell, a sense of touch, a sense of taste, and a movement or an attitude in a case of using a robot.

<6> The information processing apparatus according to <2>,
in which the reinforcement target behavior is photographing.

<7> The information processing apparatus according to <6>, further including:
an imaging control unit configured to control imaging of a photograph captured in the photographing; and
a display control unit configured to cause the photograph and the avatar to be displayed.

<8> The information processing apparatus according to <2>, in which the information processing unit presents the information used to urge the reinforcement target behavior as a task.

<9> The information processing apparatus according to any one of <1> to <8>, further including:

an emotion estimation unit configured to analyze the detected electroencephalogram, determine a score indicating a degree of intensity or a ratio for each of a plurality of elemental emotions, and output the score as the emotion estimation result.

<10> The information processing apparatus according to <9>, in which the information processing unit specifies a predetermined emotion on the basis of the score for each of the plurality of elemental emotions every time the emotion estimation result is output and stores a number of times of specification of the predetermined emotion in a long-term change table for each of the plurality of elemental emotions.

<11> The information processing apparatus according to <10>, in which the information processing unit changes and presents a form of the avatar on the basis of the number of times of specification of the predetermined emotion for each of the emotions, the number of times being stored in the long-term change table.

<12> The information processing apparatus according to <10>, in which the predetermined emotion is a dominant emotion having a highest intensity or ratio in the plurality of elemental emotions, and the information processing unit changes and presents the characteristics of the avatar depending on an emotion having a number of times of specification of the dominant emotion larger than a predetermined number of times, the number of times being stored in the long-term change table.

<13> The information processing apparatus according to <1>, in which the reinforcement target behavior is photographing, and the information processing unit stores an image captured by the photographing as a history in association with information regarding the characteristics of the avatar.

<14> The information processing apparatus according to <13>, in which the information processing unit further records information relating to an emotion based on the emotion estimation result in association with the image captured by the photographing.

<15> The information processing apparatus according to any one of <1> to <14>, in which the information processing unit causes a display unit to display a history image indicating a history of a change in the characteristics of the avatar.

<16> The information processing apparatus according to <1>, in which the information processing unit causes a display unit to display a predictive image used to predict a change in the characteristics of the avatar on the basis of the emotion estimation results obtained a plurality of times.

<17> An information processing method including:

information processing of changing characteristics of an avatar determined by a previous emotion estimation result to other characteristics on the basis of an emotion estimation result estimated on the basis of an electroencephalogram detected in response to reinforcement target behavior and presenting the characteristics.

<18> A program causing a computer to function as:

an information processing unit configured to change characteristics of an avatar determined by a previous emotion estimation result to other characteristics on the basis of an emotion estimation result estimated on the basis of an electroencephalogram detected in response to reinforcement target behavior and present the characteristics.

<19> An information processing system including:

an electroencephalograph; and
an information processing apparatus,
in which the electroencephalograph includes
an electroencephalogram detection unit configured to detect an electroencephalogram in response to reinforcement target behavior by a user, and
the information processing apparatus includes
an information processing unit configured to change characteristics of an avatar determined by a previous emotion estimation result to other characteristics on the basis of an emotion estimation result estimated on the basis of the detected electroencephalogram and present the characteristics.

REFERENCE SIGNS LIST

11 Information processing system
21 User
31 Electroencephalograph
32 Sensor
41 Information processing apparatus
42 Display apparatus
43 Server
71-1 to 71-n Electrode
72 Signal processing unit
73 Control unit
74 Communication unit
91 Control unit
92 Communication unit
93 Information processing unit
94 Imaging unit
95 Image processing unit
96 Storage unit
111 Control unit
112 Input/output unit
113 Display unit
114 Communication unit
501 Server
511-1 to 511-3 Terminal
601 VR goggle-type electroencephalograph
631, 641 ARg lass-type electroencephalograph

The invention claimed is:

1. An information processing apparatus comprising:
an information processing unit configured to
change a form of an avatar, which includes at least three forms occurring in series, from a previous form of the at least three forms determined by a previous emotion estimation result to a current form of the at least three forms on a basis of a current emotion estimation result estimated on a basis of an electroencephalogram detected in response to reinforcement target behavior, and
present the form of the avatar,
wherein the changing of the form to the current form occurs only after the form of the avatar changed to each form of the at least three forms preceding the current form, wherein each form of the at least three forms represents a stage of growth of the avatar, wherein the information processing unit is further configured to change the form of the avatar based on a predetermined emotion being repeated a predetermined number of times, and wherein the information processing unit is implemented via at least one processor.

2. The information processing apparatus according to claim 1, wherein the information processing unit is further configured to present information used to urge the reinforcement target behavior, the information processing apparatus further comprises an electroencephalogram detection unit configured to detect the electroencephalogram at a predetermined timing based on a timing of executing the reinforcement target behavior, and the electroencephalogram detection unit is implemented via at least one processor.

3. The information processing apparatus according to claim 2, wherein the electroencephalogram detection unit is further configured to detect the electroencephalogram at the timing of executing the reinforcement target behavior, during a period from timing before a predetermined time of the timing of executing the reinforcement target behavior to timing after a predetermined time of the timing of executing the reinforcement target behavior, or during a predetermined period from a timing of a predetermined time before the timing of executing the reinforcement target behavior.

4. The information processing apparatus according to claim 2, wherein the reinforcement target behavior includes photographing.

5. The information processing apparatus according to claim 4, further comprising:

an imaging control unit configured to control imaging of a photograph captured in the photographing; and a display control unit configured to cause the photograph and the avatar to be displayed, wherein the imaging control unit and the display control unit are each implemented via at least one processor.

6. The information processing apparatus according to claim 2, wherein the information processing unit is further configured to present the information used to urge the reinforcement target behavior as a task.

7. The information processing apparatus according to claim 1, wherein the avatar is a form of representation for causing a user to recognize the current emotion estimation result.

8. The information processing apparatus according to claim 1, wherein the form of the avatar includes at least one of an appearance of the avatar, displayed contents of a text format, voice, vibration, smell, a sense of touch, a sense of taste, or a movement or an attitude in a case of using a robot.

9. The information processing apparatus according to claim 1, further comprising:

an emotion estimation unit configured to analyze the detected electroencephalogram, determine a score indicating a degree of intensity or a ratio for each of a plurality of elemental emotions, and output the score as the current emotion estimation result, wherein the emotion estimation unit is implemented via at least one processor.

10. The information processing apparatus according to claim 9, wherein the information processing unit is further configured to specify the predetermined emotion on a basis of the score for each of the plurality of elemental emotions every time the current emotion estimation result is output, and store a number of times of specification of the predetermined emotion in a long-term change table for each of the plurality of elemental emotions.

11. The information processing apparatus according to claim 10, wherein the information processing unit is further configured to change and present a form of the avatar on a basis of the number of times of specification of the predetermined emotion for each of the emotions, the number of times being stored in the long-term change table.

12. The information processing apparatus according to claim 10, wherein the predetermined emotion is a dominant emotion having a highest intensity or ratio in the plurality of elemental emotions, and the information processing unit is further configured to change and present the form of the avatar depending on an emotion having a number of times of specification of the dominant emotion larger than the predetermined number of times, the number of times being stored in the long-term change table.

13. The information processing apparatus according to claim 1, wherein the reinforcement target behavior includes photographing, and the information processing unit is further configured to store an image captured by the photographing as a history in association with information regarding the form of the avatar.

14. The information processing apparatus according to claim 13, wherein the information processing unit is further configured to record information relating to an emotion based on the current emotion estimation result in association with the image captured by the photographing.

15. The information processing apparatus according to claim 1, wherein the information processing unit is further configured to cause a display unit to display a history image indicating a history of a change in the form of the avatar.

16. The information processing apparatus according to claim 1, wherein the information processing unit is further configured to cause a display unit to display a predictive image used to predict a change in the form of the avatar on a basis of the emotion estimation results obtained a plurality of times.

17. The information processing apparatus according to claim 1, wherein the information processing unit is further configured to present information used to change a current behavior to the reinforcement target behavior different than the current behavior.

18. The information processing apparatus according to claim 1, wherein the previous emotion estimation result is same as the current emotion estimation result.

19. An information processing method comprising:

changing a form of an avatar, which includes at least three forms occurring in series, from a previous form of the at least three forms determined by a previous emotion estimation result to a current form of the at least three forms on a basis of a current emotion estimation result estimated on a basis of an electroencephalogram detected in response to reinforcement target behavior; and presenting the form of the avatar, wherein the changing of the form to the current form occurs only after the form of the avatar changed to each form of the at least three forms preceding the current form, wherein each form of the at least three forms represents a stage of growth of the avatar, and wherein the information processing unit is further configured to change the form of the avatar based on a predetermined emotion being repeated a predetermined number of times.

20. A non-transitory recording medium having embodied thereon a program, which when executed by a computer causes the computer to execute an information processing method, the method comprising:

changing a form of an avatar, which includes at least three forms occurring in series, from a previous form of the at least three forms determined by a previous emotion estimation result to a current form of the at least three forms on a basis of a current emotion estimation result estimated on a basis of an electroencephalogram detected in response to reinforcement target behavior; and presenting the form of the avatar, wherein the changing of the form to the current form occurs only after the form of the avatar changed to each form of the at least three forms preceding the current form, wherein each form of the at least three forms represents a stage of growth of the avatar, and wherein the information processing unit is further configured to change the form of the avatar based on a predetermined emotion being repeated a predetermined number of times.

21. An information processing system comprising:

an electroencephalograph; and an information processing apparatus, wherein the electroencephalograph includes an electroencephalogram detection unit configured to detect an electroencephalogram in response to reinforcement target behavior by a user, and the information processing apparatus includes an information processing unit configured to change a form of an avatar, which includes at least three forms occurring in series, from a previous form of the at least three forms determined by a previous emotion estimation result to a current form of the at least three forms on a basis of a current emotion estimation result estimated on a basis of the detected electroencephalogram, and present the form of the avatar, wherein the changing of the form to the current form occurs only after the form of the avatar changed to each form of the at least three forms preceding the current form, wherein each form of the at least three forms represents a stage of growth of the avatar, wherein the electroencephalogram detection unit and the information processing unit are each implemented via at least one processor, and wherein the information processing unit is further configured to change the form of the avatar based on a predetermined emotion being repeated a predetermined number of times.

* * * * *